US009788809B2

(12) United States Patent
Hiroike et al.

(10) Patent No.: US 9,788,809 B2
(45) Date of Patent: Oct. 17, 2017

(54) APPARATUS, METHOD AND COMPUTER-READABLE MEDIUM STORING PROGRAM FOR RADIOGRAPHIC IMAGING WITH ELAPSED TIME CONTROL OF RADIATION SENSOR APPARATUS

(71) Applicant: CANON KABUSHIKI KAISHA, Tokyo (JP)

(72) Inventors: Taro Hiroike, Yamato (JP); Norihiko Miyachi, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 615 days.

(21) Appl. No.: 14/198,273

(22) Filed: Mar. 5, 2014

(65) Prior Publication Data

US 2014/0254760 A1 Sep. 11, 2014

(30) Foreign Application Priority Data

Mar. 6, 2013 (JP) .................................. 2013-044404
Mar. 6, 2013 (JP) .................................. 2013-044405
Mar. 6, 2013 (JP) .................................. 2013-044722

(51) Int. Cl.
*A61B 6/00* (2006.01)

(52) U.S. Cl.
CPC .............. *A61B 6/54* (2013.01); *A61B 6/4233* (2013.01)

(58) Field of Classification Search
CPC ......... A61B 6/548; A61B 6/563; A61B 6/542; A61B 6/56; A61B 6/54; A61B 6/545; A61B 6/566; A61B 6/586; H04N 5/232; H04N 5/23245; H04N 5/343; G01N 2223/304; H05G 1/30; H05G 1/56; H05G 1/58; G01T 1/246; G01T 1/171; G06F 19/3406

See application file for complete search history.

(56) References Cited

U.S. PATENT DOCUMENTS 6,127,684 A * 10/2000 Kaifu ........................ H04N 5/32
                                                     250/208.1
6,448,561 B1 * 9/2002 Kaifu ...................... H04N 5/235
                                                     250/370.09
7,592,577 B1 * 9/2009 Liu .................... H01L 27/14643
                                                     250/208.1
(Continued)

FOREIGN PATENT DOCUMENTS

JP          11-155847 A      6/1999
JP        2000-347330 A     12/2000
(Continued)

*Primary Examiner* — Brooke Purinton

(74) *Attorney, Agent, or Firm* — Canon USA Inc., IP Division

(57) ABSTRACT

A radiographic imaging control apparatus includes a control unit, a setting unit, and an obtaining unit. The control unit performs a first control to cause a radiation sensor to transit into a state where electric charges can be stored if it is determined that a predetermined standby time elapses and performs a second control to cause the radiation sensor to transit into the state where electric charges can be stored in response to a signal received from a detection unit configured to detect start of a generation of radioactive rays. The setting unit designates either the first control or the second control as a control to be performed. The obtaining unit acquires radiation image data from the radiation sensor.

25 Claims, 19 Drawing Sheets

PREPARATION FOR PHOTOGRAPHING OPERATION IS IN PROGRESS.
TIME LEFT BEFORE STARTING PHOTOGRAPHING OPERATION IS

5 SECONDS.

PRESS ONLY FIRST SWITCH OF IRRADIATION SWITCH.

(56) References Cited

U.S. PATENT DOCUMENTS

| | | | |
|---|---|---|---|
| 2003/0086523 A1* | 5/2003 | Tashiro | A61B 6/00 378/19 |
| 2004/0258204 A1* | 12/2004 | Nokita | A61B 6/00 378/91 |
| 2009/0108311 A1* | 4/2009 | Liu | H01L 27/14663 257/294 |
| 2009/0109313 A1* | 4/2009 | Liu | H04N 3/155 348/308 |
| 2010/0102241 A1* | 4/2010 | Zeller | G01T 1/17 250/370.09 |
| 2010/0207032 A1* | 8/2010 | Tsubota | G01T 1/17 250/370.09 |
| 2011/0111703 A1* | 5/2011 | Claverie | H04N 5/32 455/66.1 |
| 2012/0018641 A1* | 1/2012 | Watanabe | A61B 6/4233 250/354.1 |
| 2012/0134474 A1* | 5/2012 | Duca | A61B 6/4233 378/96 |
| 2013/0136234 A1* | 5/2013 | Noma | H05G 1/64 378/91 |
| 2013/0208860 A1* | 8/2013 | Sugizaki | G01T 1/2928 378/62 |
| 2014/0072103 A1* | 3/2014 | Kitano | A61B 6/4233 378/62 |

FOREIGN PATENT DOCUMENTS

| | | |
|---|---|---|
| JP | 2005-013272 A | 1/2005 |
| JP | 2006-247138 A | 9/2006 |
| JP | 2006-305106 A | 11/2006 |
| JP | 2010-104398 A | 5/2010 |
| JP | 2010-200929 A | 9/2010 |
| JP | 2010-214095 A | 9/2010 |
| JP | 4684747 B2 | 5/2011 |
| JP | 2012-100797 A | 5/2012 |
| JP | 2012-125309 A | 7/2012 |
| NO | 2013/015266 A1 | 1/2013 |

* cited by examiner

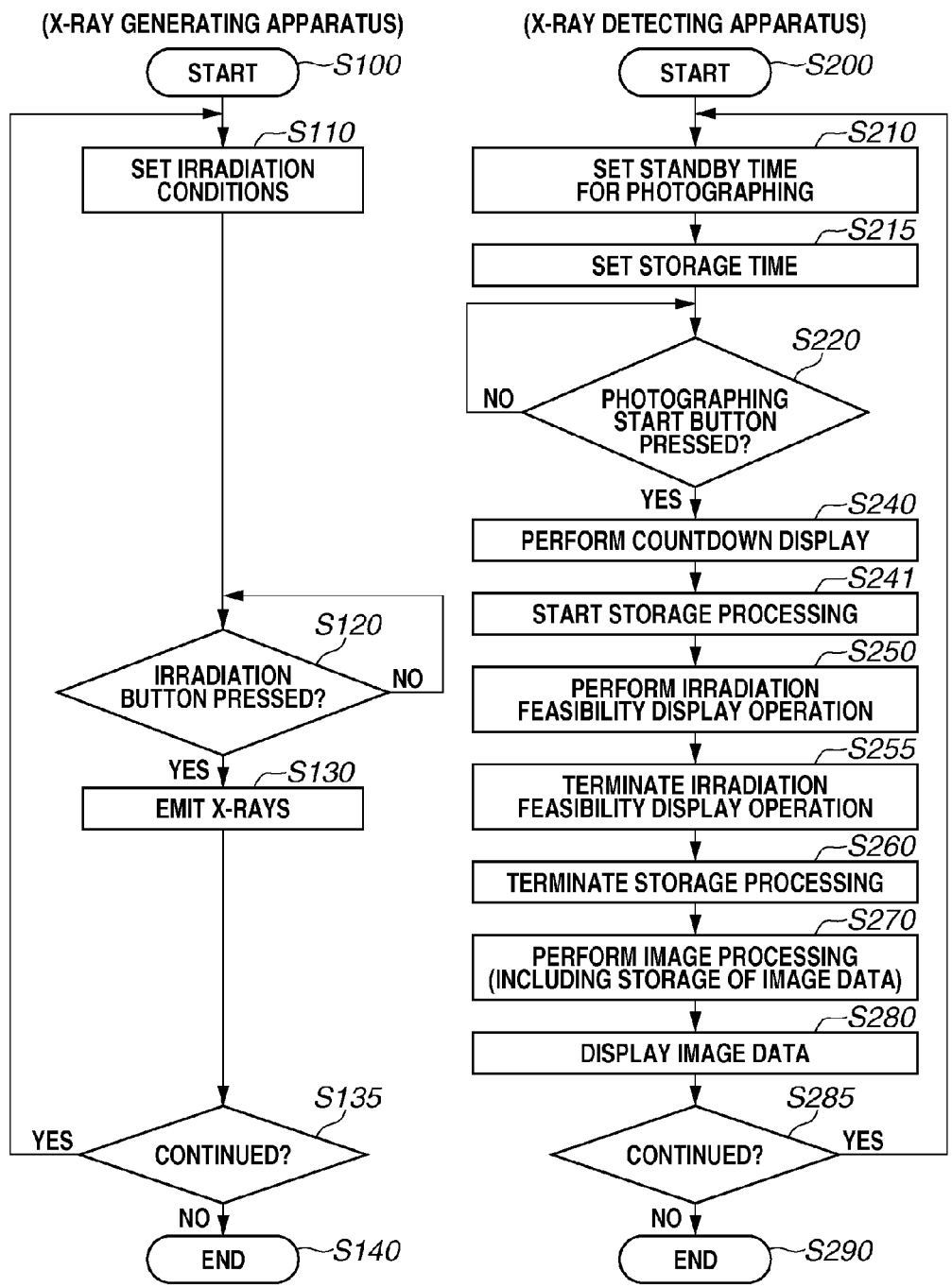

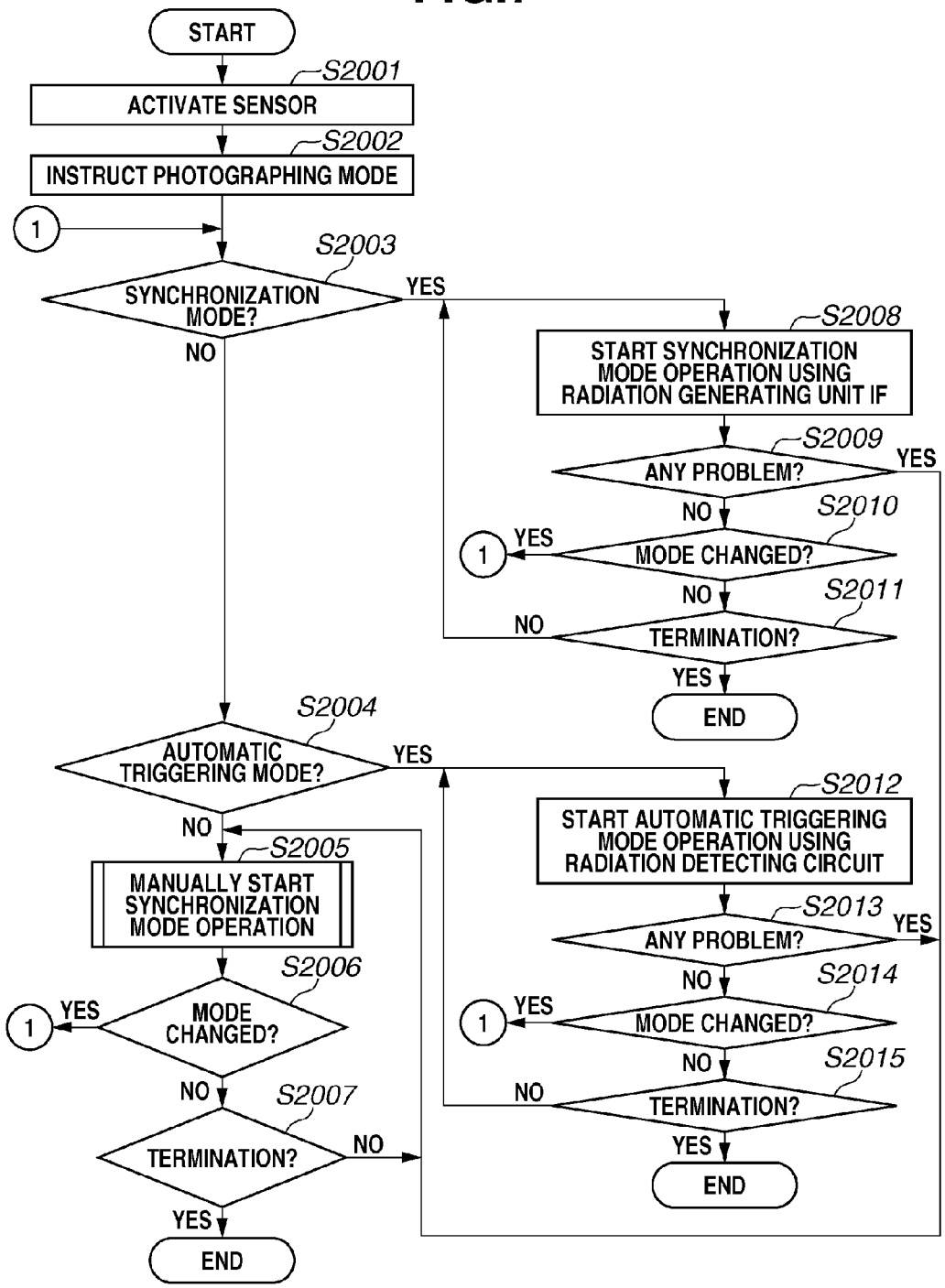

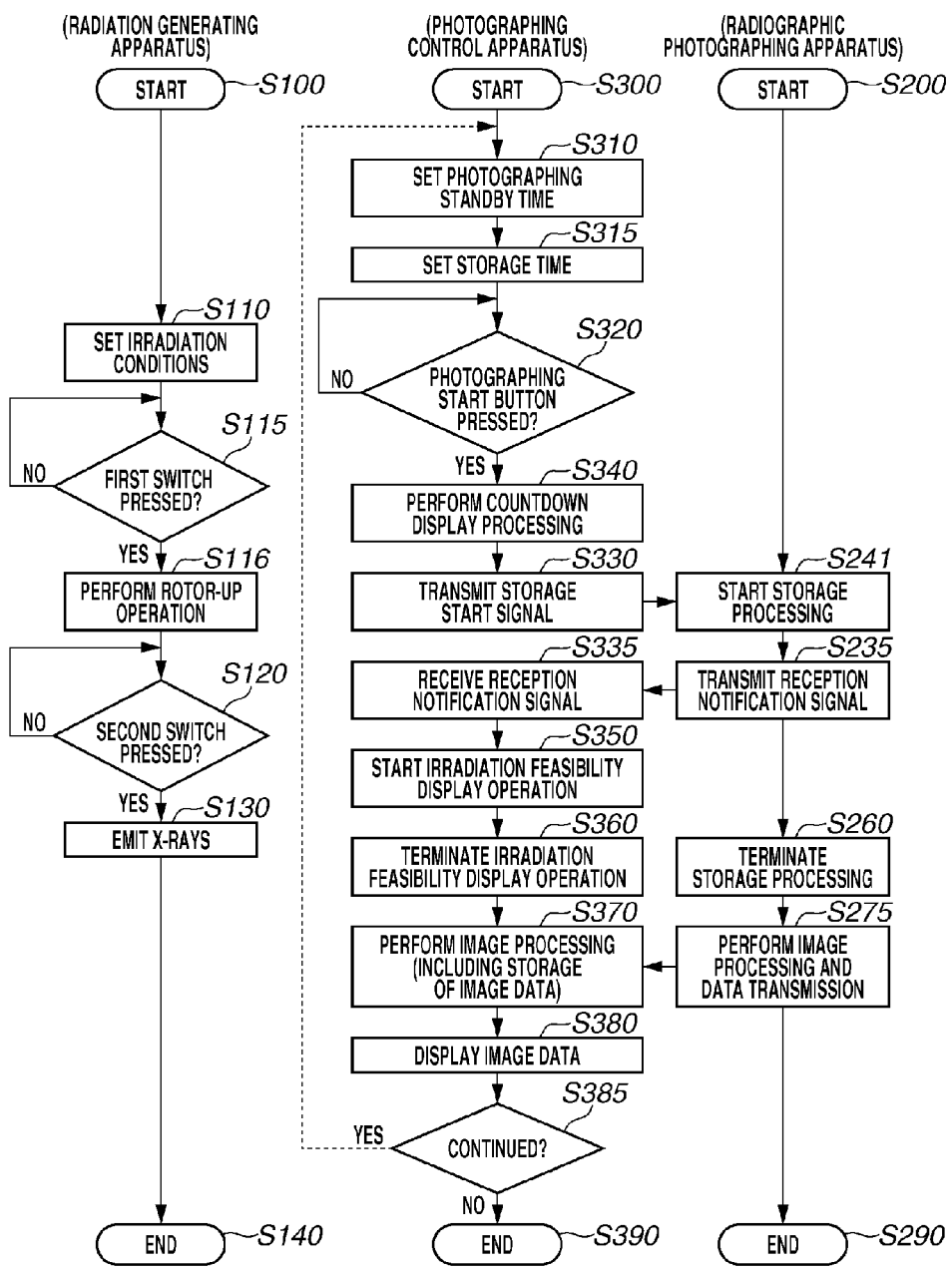

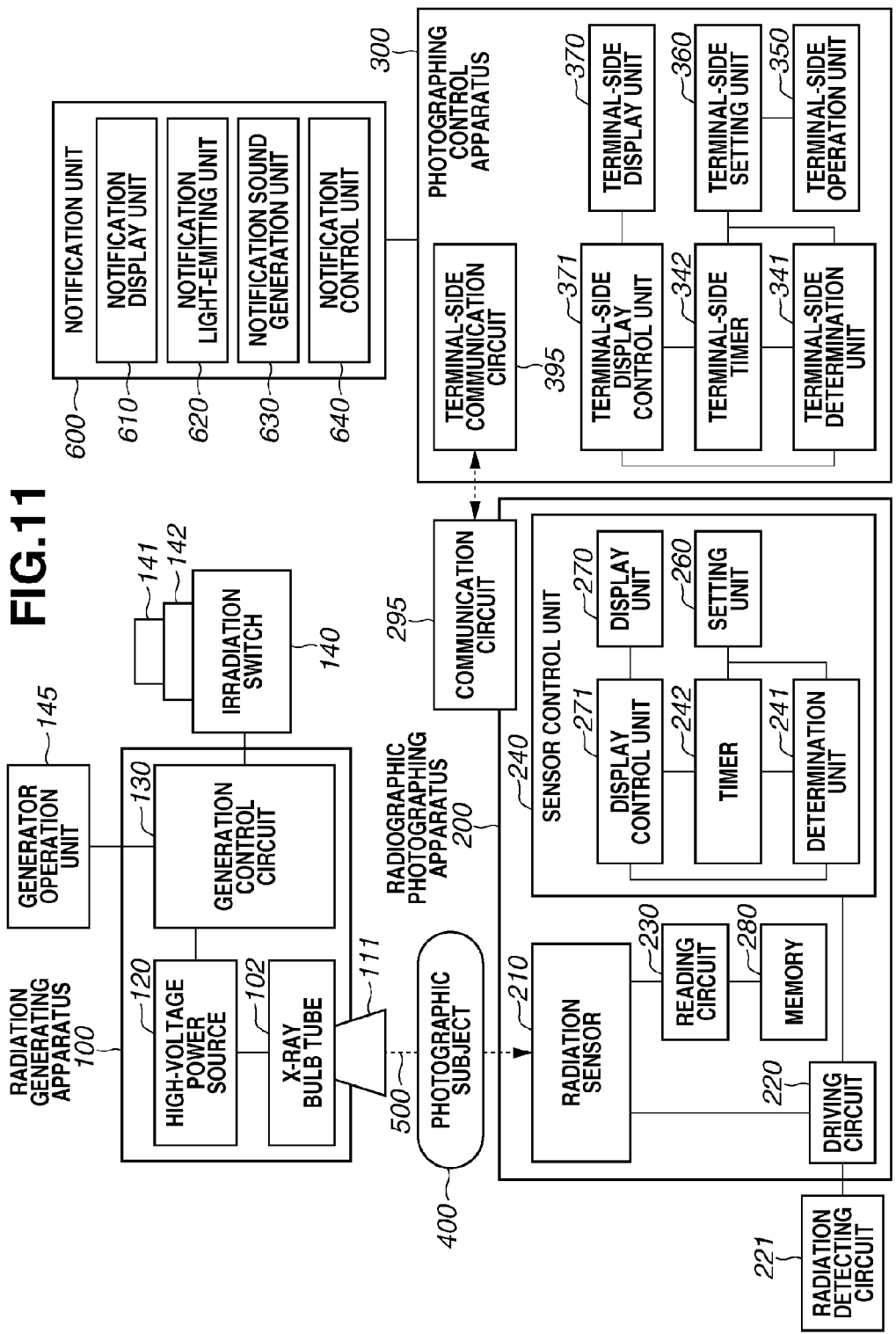

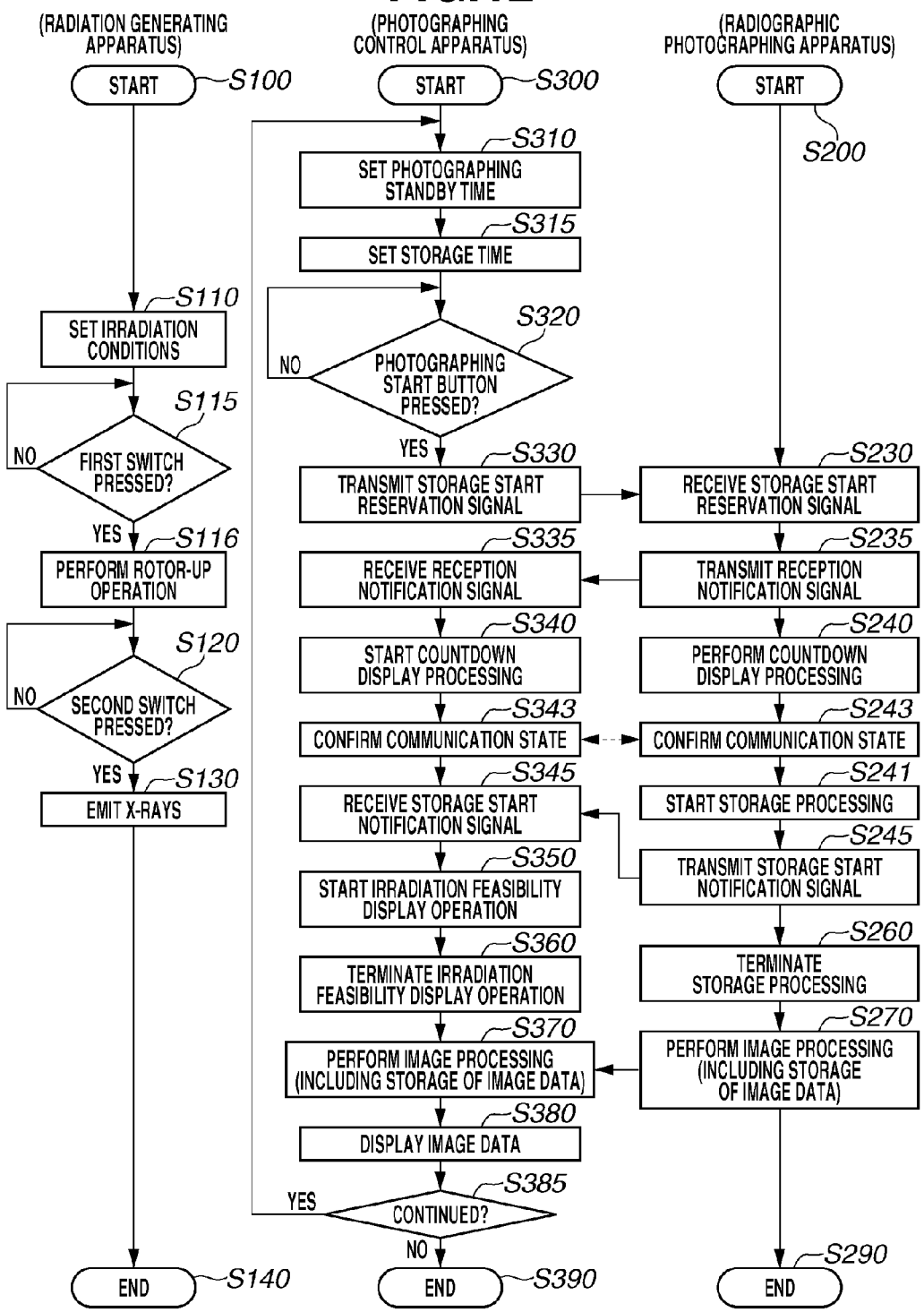

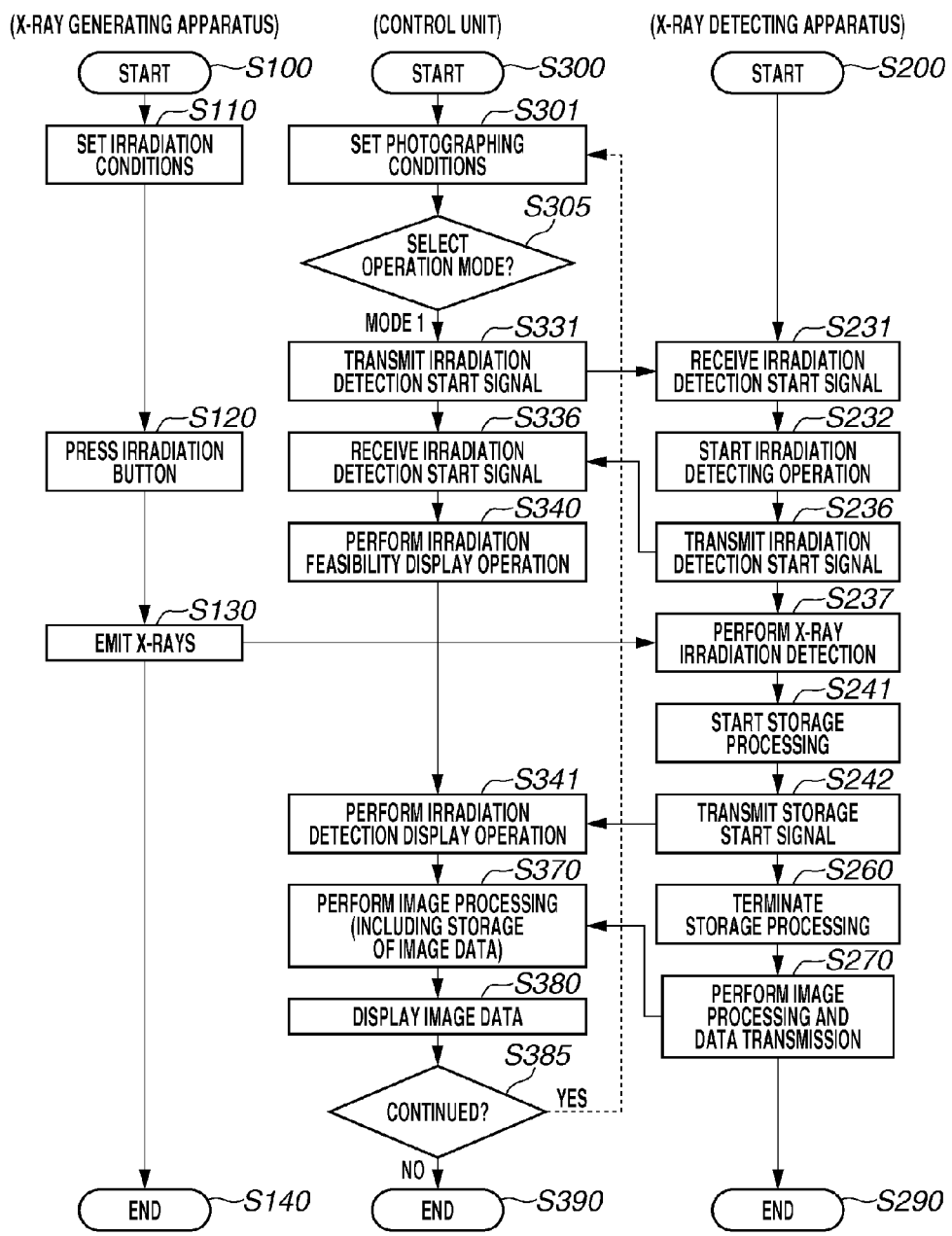

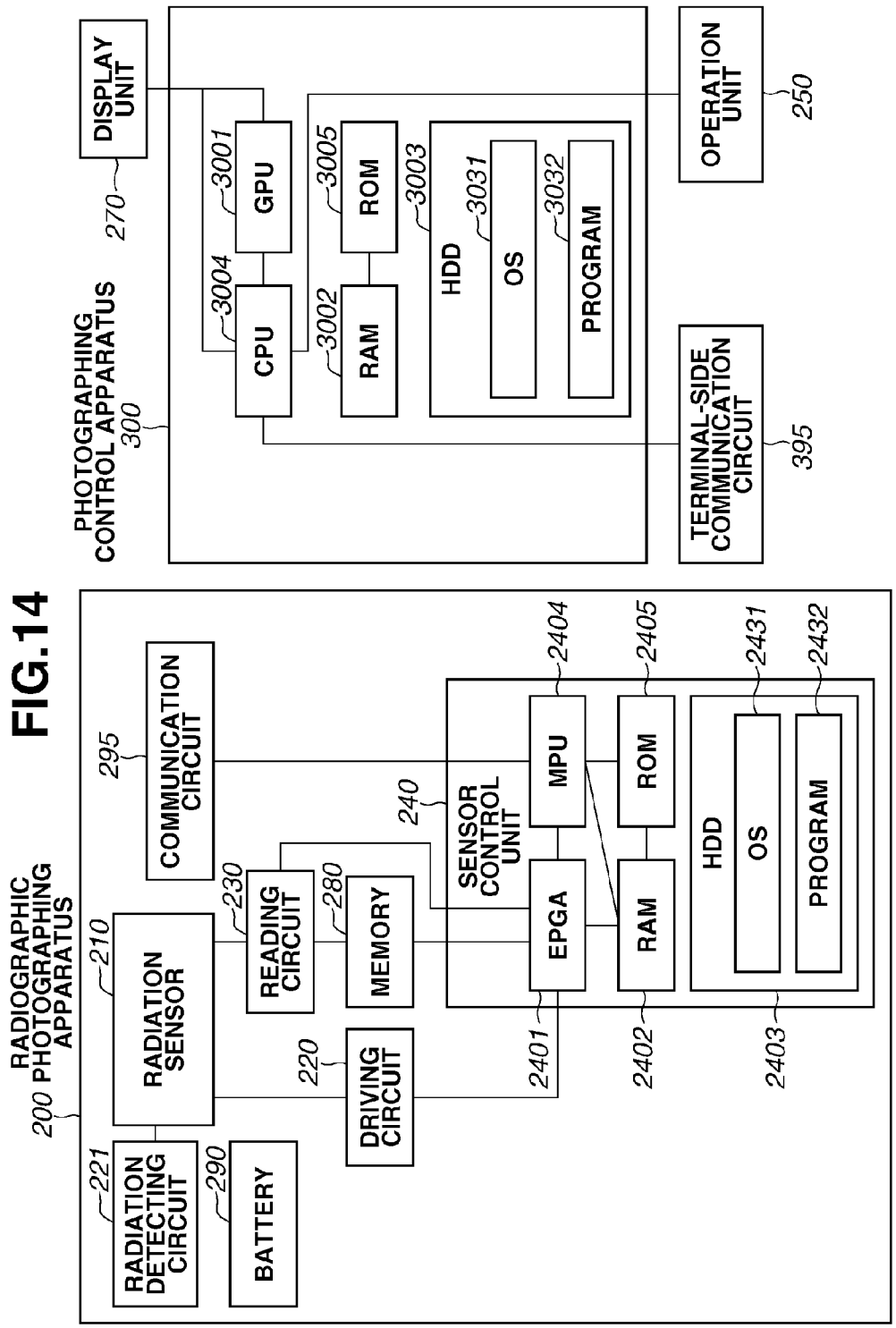

FIG.19

| | POWER OFF | PHOTOGRAPHING INFEASIBLE | PHOTOGRAPHING PREPARATION | PHOTOGRAPHING PERMISSIBLE | PHOTOGRAPHING IN PROGRESS |
|---|---|---|---|---|---|
| FIRST PHOTOGRAPHING MODE | — | LIGHT-OFF | FIRST NOTIFICATION LIGHT | FIRST NOTIFICATION LIGHT | LIGHT-OFF |
| SECOND PHOTOGRAPHING MODE | — | LIGHT-OFF | LIGHT-OFF | SECOND NOTIFICATION LIGHT / FIRST TO FOURTH NOTIFICATION SOUNDS | LIGHT-OFF |
| THIRD PHOTOGRAPHING MODE | — | LIGHT-OFF | — | — | THIRD NOTIFICATION LIGHT / FIFTH NOTIFICATION SOUND |

APPARATUS, METHOD AND COMPUTER-READABLE MEDIUM STORING PROGRAM FOR RADIOGRAPHIC IMAGING WITH ELAPSED TIME CONTROL OF RADIATION SENSOR APPARATUS

BACKGROUND OF THE INVENTION

Field of the Invention

The present invention relates to a radiographic imaging control apparatus, a radiographic imaging apparatus, a radiographic imaging system, a method for controlling the same, and a program causing a computer to execute the control method.

Description of the Related Art

Digital radiation images (e.g., X-ray images) are widely used in the medical fields, recently. As a practical method, instead of using a film, a digital radiographic imaging apparatus associated with a radiation sensor is usable to acquire digital radiation images. The radiation sensor includes a plurality of radiation detection elements disposed in a two-dimensional matrix pattern to form an image by converting radioactive rays into electric signals.

For example, when an operator uses the above-mentioned radiographic imaging apparatus in medical diagnosis, the efficiency of the diagnosis can be improved greatly because the operator can immediately confirm a captured image on a display apparatus thereof.

In a case where the digital radiographic imaging apparatus is used to perform an X-ray imaging operation, the characteristics of a used solid-state detection element should be taken into consideration. In this respect, it is desired to equalize the timing to generate X-rays with the timing to cause a detector to start storing electric charges (i.e., an imaging operation).

In the X-ray imaging system discussed in the Japanese Patent No. 4684747, an X-ray generation apparatus and a flat panel detector (FPD) mutually transmit and receive synchronizing signals to synchronize the X-ray irradiation with the imaging timing. The X-ray imaging system discussed in Japanese Patent Application Laid-Open No. 11-155847 detects X-ray generation timing by detecting a change in the current flowing in the FPD when the FPD is irradiated with X-rays and starts an imaging operation in response to the detection of the X-ray generation timing.

A system discussed in Japanese Patent Application Laid-Open No. 2005-13272 includes a notification device that can notify a non-storage state and a storage state of a detector. Providing such a notification device is useful to enable an operator to instruct the system to start generating X-rays at appropriate timing to obtain an X-ray image.

The timing adjusting method is variable depending on system configuration or imaging conditions. Therefore, it is desired to provide a system that can select an optimum timing adjusting method taking a momentary situation into consideration.

SUMMARY OF THE INVENTION

According to an aspect of the present invention, a radiographic imaging control apparatus includes a control unit, a setting unit, and an obtaining unit. The control unit is configured to perform a first control to cause a radiation sensor to transit into a state where electric charges can be stored if it is determined that a predetermined standby time elapses, and to perform a second control to cause the radiation sensor to transit into the state where electric charges can be stored in response to a signal received from a detection unit configured to detect a start of generation of radioactive rays. The setting unit is configured to designate either the first control or the second control as a control to be performed. The obtaining unit is configured to acquire radiation image data from the radiation sensor that has transited into a storage state based on the designated control.

Further features of the present invention will become apparent from the following description of exemplary embodiments with reference to the attached drawings.

BRIEF DESCRIPTION OF THE DRAWINGS

FIG. 5 is a flowchart illustrating an imaging operation that can be performed by the radiographic imaging system.

FIG. 7 is a flowchart illustrating an imaging mode switching operation that can be performed by the radiographic imaging system.

FIG. 9 is a flowchart illustrating an imaging operation that can be performed by the radiographic imaging system that includes the imaging control apparatus.

FIGS. 10A to 10C illustrate example display screens that can be displayed by the display unit, in which FIG. 10A illustrates a standby time setting screen, FIG. 10B illustrates a countdown display screen, and FIG. 10C illustrates an irradiation feasibility display screen.

FIG. 11 illustrates a configuration example of a radiographic imaging system that includes a portable radiographic imaging apparatus and an independent imaging control apparatus according to an exemplary embodiment.

FIG. 12 is a flowchart illustrating an imaging operation that can be performed by the radiographic imaging system that includes the portable radiographic imaging apparatus and the independent imaging control apparatus.

FIG. 13 is a flowchart illustrating an imaging operation that can be realized by using a radiation detecting circuit.

FIG. 14 illustrates a hardware configuration example of the portable radiographic imaging apparatus and the imaging control apparatus.

FIG. 19 is a table illustrating example transitions of notification state according to the imaging mode and each operational state of the X-ray detector.

DESCRIPTION OF THE EMBODIMENTS

Various exemplary embodiments, features, and aspects of the invention will be described in detail below with reference to the drawings.

Figure 1:
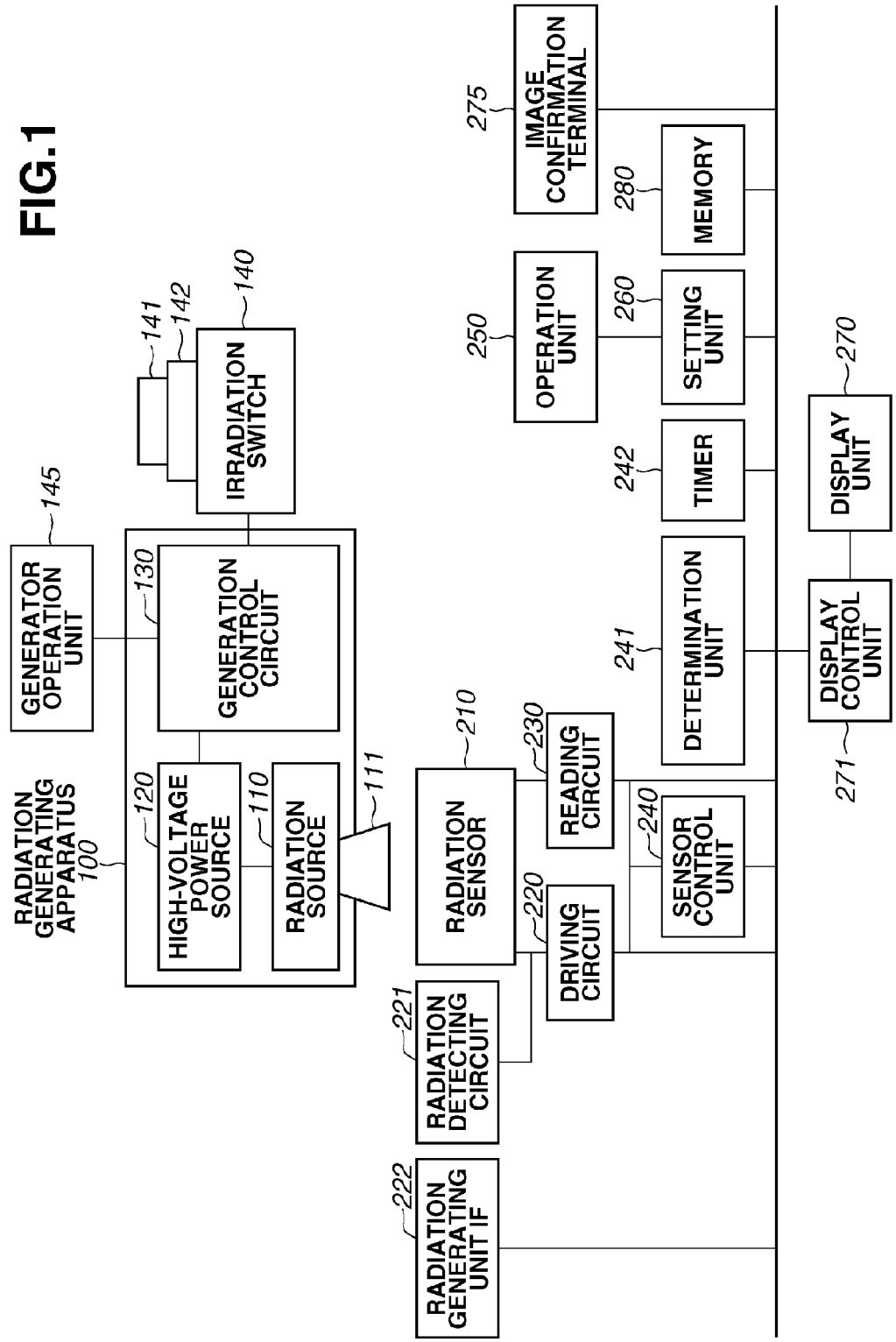
FIG. 1 illustrates a configuration example of a radiographic imaging system according to an exemplary embodiment of the present invention.

A configuration example of a radiographic imaging system according to an exemplary embodiment is described in detail below with reference to FIG. 1.

The radiographic imaging system includes a radiation generating apparatus 100. The radiation generating apparatus 100 includes a radiation source 110, a radiation throttle 111, a high-voltage power source 120, a generation control circuit 130, a generator operation unit 145, and an irradiation switch 140. For example, the radiation source 110 includes a reflection-type or transmission-type target and an electron source that generates electrons. The radiation source 110 is configured to generate radioactive rays by causing the generated electrons to collide with the target.

The radiation throttle 111 includes a plurality of radiation shielding members, which is appropriately arranged to form a radiation flux having a desired shape. For example, the radiation flux can be shaped to have a cross section perpendicular to the radiation direction, which has a rectangular or circular shape. The high-voltage power source 120 can generate a higher voltage to accelerate electrons when the electrons are generated by the electron source. The generation control circuit 130 is configured to control generation of radioactive rays.

The generator operation unit 145 is operable to set generation conditions for generating radioactive rays. The generation control circuit 130 is configured to control an operation according to the generation conditions (e.g., tube current, tube voltage, and mAs value). The irradiation switch 140 is a two-stage switch operable to control radiation generation timing. The irradiation switch 140 includes a first (first-stage) switch 141 and a second (second-stage) switch 142. When the first switch 141 is pressed, the irradiation switch 140 sends a rotor-up signal to the generation control circuit 130. The generation control circuit 130 causes the radiation source 110 to start rotating an anode thereof.

Then, if the second switch 142 is pressed in a state where a rotor-up operation has been completed, the irradiation switch 140 sends an exposure signal to the generation control circuit 130. The generation control circuit 130 starts controlling the generation of radioactive rays. The rotor-up operation is unnecessary when the target is a transmission-type. However, it is unnecessary to change the flow of control that includes the above-mentioned preparatory operation triggered by the first switch 141 and the startup of exposure triggered by the second switch 142. Alternatively, the irradiation switch 140 can be configured as a single-stage switch in a case where the target is a transmission-type.

A radiation sensor 210 is appropriately positioned to detect radioactive rays to be generated by the above-mentioned radiation generating apparatus 100. The radiographic imaging system is described in detail below.

The radiographic imaging system includes a driving circuit 220, a reading circuit 230, a sensor control unit 240, a determination unit 241, a timer 242, an operation unit 250, a setting unit 260 (i.e., time setting unit), a display unit 270, a display control unit 271, and a memory 280, in addition to the radiation sensor 210. The components constituting the radiographic imaging system can mutually transmit and receive signals via a wired or wireless network or via an electric connection.

The sensor control unit 240, the determination unit 241, the timer 242, the operation unit 250, the setting unit 260, and the display control unit 271 are cooperative to control the radiographic imaging system. The radiation sensor 210, the driving circuit 220, the sensor control unit 240, and the memory 280 are included in a radiographic imaging unit. The sensor control unit 240, the determination unit 241, the setting unit 260, and the display control unit 271 can be packaged, for example, as a field programmable gate array (FPGA). To realize functions and processing of each of the above-mentioned units, configuration data of a logic circuit formed on the FPGA can be generated using hardware description languages and the configuration setting of the FPGA can be performed using the configuration data.

The radiation sensor 210 includes a plurality of pixels disposed in a two-dimensional matrix pattern. Each pixel can store electric charges according to reception of radioactive rays. The operating mode of the radiation sensor 210 is selectable between a storage mode and a reading mode. In the storage mode, the radiation sensor 210 is operable to store electric charges. In the reading mode, the radiation sensor 210 is operable to read an electric signal based on the stored electric charges. For example, the radiation sensor 210 includes a plurality of row selection lines, which is provided for respective rows and connected to the driving circuit 220. The radiation sensor 210 further includes a plurality of column signal lines, which is provided for respective columns and connected to the reading circuit 230.

Each pixel includes a PIN or MIS-type photoelectric conversion element and a thin film transistor (TFT) that connects the photoelectric conversion element to the column signal line. The TFT has a base electrode to which the column signal line is connected. The TFT can be ON/OFF controlled by the driving circuit 220. When the TFT is turned on, the pixel is brought into a storage state (or the storage mode) in which electric charges are stored. When the TFT is turned off, the pixel is brought into a reading state (or the reading mode) in which the stored electric charges are read.

The operation unit 250, the setting unit 260, the timer 242, the determination unit 241, and the sensor control unit 240 cooperatively control the timing when the operation mode of the radiation sensor 210 transits from the reading mode to the storage mode. The operation unit 250 includes hard buttons and soft buttons displayable on a display screen of the display unit 270. The operation unit 250 can receive time information input by a user to perform standby time setting and an instruction to start an imaging operation. The setting unit 260 stores the input time information, as standby time information, in a memory. Further, in response to the instruction input via the operation unit 250, the radiographic imaging system starts clocking the standby time.

The timer 242 includes, for example, a clock pulse generator and a counter circuit. The counter circuit outputs a count value by repeating counting the number of clock pulses at predetermined intervals. The determination unit 241 monitors the timer 242 and repetitively performs determination processing to determine whether the standby time elapses since the time setting determined by the user. Through the above-mentioned processing, the timer 242 and the determination unit 241 can determine whether the standby time (i.e., time information having been input by a user) has elapsed.

After the standby time elapses, the sensor control unit 240 transmits a control signal (i.e., a mode change instruction) to the driving circuit 220. The driving circuit 220 shifts the operation mode of the radiation sensor 210 to the storage mode. Thus, the radiation sensor 210 can be brought into the storage state upon passage of the desired time input by a user.

As mentioned above, in this mode, an operator can instruct radiating X-rays to perform an imaging operation in synchronization with timing when the radiation sensor 210 starts a storage operation. It is useful to inform a user of the timing when X-rays can be radiated to enable the user to input a radiation start instruction with reference to the notification. Thus, the X-ray irradiation timing can be synchronized with the imaging timing in the imaging operation.

Providing the standby time (i.e., the time arbitrarily changed by a user) before shifting the operation mode to the storage mode is useful in that the user can adequately set the start timing of the storage mode. For example, in a case where no problem occurs even when the radiation generating apparatus 100 immediately starts a radiographic imaging operation, it is feasible to set the standby time to be equal to or less than three seconds (or one second) so that the radiation sensor 210 can immediately transit into the storage state and the radiation generating apparatus 100 can start the imaging operation.

In this case, it is feasible to set the standby time to 0 so that the radiation sensor 210 can immediately transit into the storage state according to the instruction without any delay. On the other hand, the standby time can be set to be 10 seconds or more when it is necessary to adjust the timing for a subject person or it is desired to provide a sufficient time before starting the storage operation.

At the time when the radiation sensor 210 transits into the storage state, if the user presses the irradiation switch 140 to cause the radiation generating apparatus 100 to generate radioactive rays, the radiation sensor 210 (in the storage state) can store electric charges according to the intensity of the radioactive rays. Subsequently, for example, after a predetermined accumulation time (i.e., a fixed time determined beforehand) has elapsed, the sensor control unit 240 outputs an instruction to the driving circuit 220 in response to the termination of the storage period to cause the radiation sensor 210 to transit into the reading mode.

The reading circuit 230 amplifies an electric signal having been read and generates digital radiation image data through A/D conversion. The memory 280 stores the generated digital radiation image data. The memory 280 can store various imaging conditions and setting values in addition to the radiation image data.

An image confirmation terminal 275 includes a communication unit, a display control unit, and a display unit. The communication unit is configured to perform, for example, wired or wireless communications to receive the above-mentioned digital radiation image data. The display control unit is configured to cause the display unit to display an image based on the received radiation image data. Further, the communication unit can transmit image data to an external server through wired or wireless communications, so that the external server can store the image data.

The radiographic imaging system can include the display unit 270 and the display control unit 271. For example, the display control unit 271 is configured to cause the display unit 270 to display a display content indicating that radio-active rays should not be generated in this period, if the standby time has not yet elapsed since the instruction input. Thus, the user can confirm the period during which no storage should be performed based on the display content of the display unit 270. Further, for example, the display control unit 271 causes the display unit 270 to display a display content indicating that the radiation should be started in response to the passage of the standby time or the transition into the storage mode. Thus, the user can confirm the imaging timing with reference to the display content of the display unit 270.

In addition, the display control unit 271 causes the display unit 270 to display a display content that is variable depending on the time left before the timing to generate radioactive rays, so that it becomes easy for the user to confirm the time to press the radiation switch. The display to be performed according to the time left before the standby time elapses is, for example, countdown display of the remaining time that can be performed by the display unit 270 or flicker display of a light-emitting diode (LED) whose interval is shortened stepwise.

Further, the radiographic imaging system according to the present exemplary embodiment can include a radiation generating unit interface (IF) 222 that electrically connects the radiographic imaging system to the radiation generating apparatus 100. The radiation generating unit IF 222 is functionally operable as a unit configured to transmit or receive a synchronizing signal to or from the radiation generating apparatus 100 to synchronize the radiation generation with the storage mode.

If the radiation generating apparatus 100 includes an interface that can output radiation generation timing, it is useful to connect their interfaces for synchronization. The synchronizing signal can be transmitted or received in the following manner. When the first switch 141 is pressed, the generation control circuit 130 completes the rotor-up operation. When the second switch 142 is pressed, the generation control circuit 130 outputs a radiation exposure permission request signal. The radiation generating unit IF 222 receives the radiation exposure permission request signal. In response to the received signal, the sensor control unit 240 shifts the operation mode of the radiation sensor 210 to the storage mode. In this case, the sensor control unit 240 can perform control to read electric charges stored in the radiation sensor 210 and can perform predetermined initialization processing.

In response to the transition into the storage mode, the sensor control unit 240 transmits an exposure permission signal via the radiation generating unit IF 222. In response to the exposure permission signal, the generation control circuit 130 causes the radiation source 110 to generate radioactive rays. Through the above-mentioned synchronizing control, a radiographic imaging operation using the radiation sensor 210 can be surely performed with an operation similar to that required for a conventional analog film (i.e., pressing of the radiation switch).

However, the radiation generating apparatus 100 may not include an appropriate interface if the type thereof is different or when a manufacturer of the radiation generating apparatus 100 is different from a manufacturer of the radiographic imaging system. In such a case, though the above-mentioned timer control and display control, a user can adjust the irradiation timing to perform the radiographic imaging operation using the radiation sensor 210.

Further, the radiographic imaging system according to the present exemplary embodiment can include a radiation detecting circuit 221. The radiation detecting circuit 221 can be used to detect radioactive rays generated from the radiation generating apparatus 100 to obtain an image in a case where the radiographic imaging system cannot synchronize with the radiation generating apparatus 100. For example, to detect the generation of radioactive rays, the radiation detecting circuit 221 monitors an output current of each pixel constituting the radiation sensor 210.

It is useful to provide a dedicated sensor having a semiconductor element sensitive to radioactive rays on a front face, a reverse face, or an external periphery of the radiation sensor 210, in addition to the radiation sensor 210. In this case, an output of the dedicated sensor is usable to detect generation of radioactive rays.

For example, the radiation sensor 210 can be held in the reading mode before it detects generation of radioactive rays and its operation mode can be shifted into the storage mode in response to the detection of radioactive rays to obtain a radiation image. Further, according to another example, the radiation sensor 210 can repetitively perform the storage and reading operations before it detects generation of radioactive rays and can generate a radiation image based on data having been read in the generation period of radioactive rays.

Although controlling the radiation sensor 210 with the radiation detecting circuit 221 is feasible as mentioned above, the detection of radioactive rays may be delayed when a special imaging operation is performed. For example, the imaging operation cannot be appropriately performed when the radiation dose is extremely low. Further, when the radiation detecting circuit is used, it is necessary to drive the radiation sensor to perform a predetermined operation before starting the detection of radioactive rays.

Each user can select one of the above-mentioned three imaging modes, i.e., the first control to perform a imaging operation using the timer, the second control to perform a imaging control using the radiation irradiation detecting circuit, and the third control to perform a synchronized imaging operation using the radiation generating unit IF 222, considering various conditions (e.g., system configuration, imaging environment, and imaging conditions).

The setting unit 260 switches the setting of the imaging mode in accordance with an operational instruction input via the operation unit 250 or in accordance with an external signal. For example, the setting unit 260 sets a setting value of the imaging mode to 0 when a synchronized imaging operation is performed, 1 when the radiation irradiation detecting circuit is used, and 2 when a timer based imaging operation is performed, respectively. The setting value of the imaging mode is stored in the memory. The setting value can be appropriately referred to in performing the imaging operation according to the mode having been set.

Figure 2:
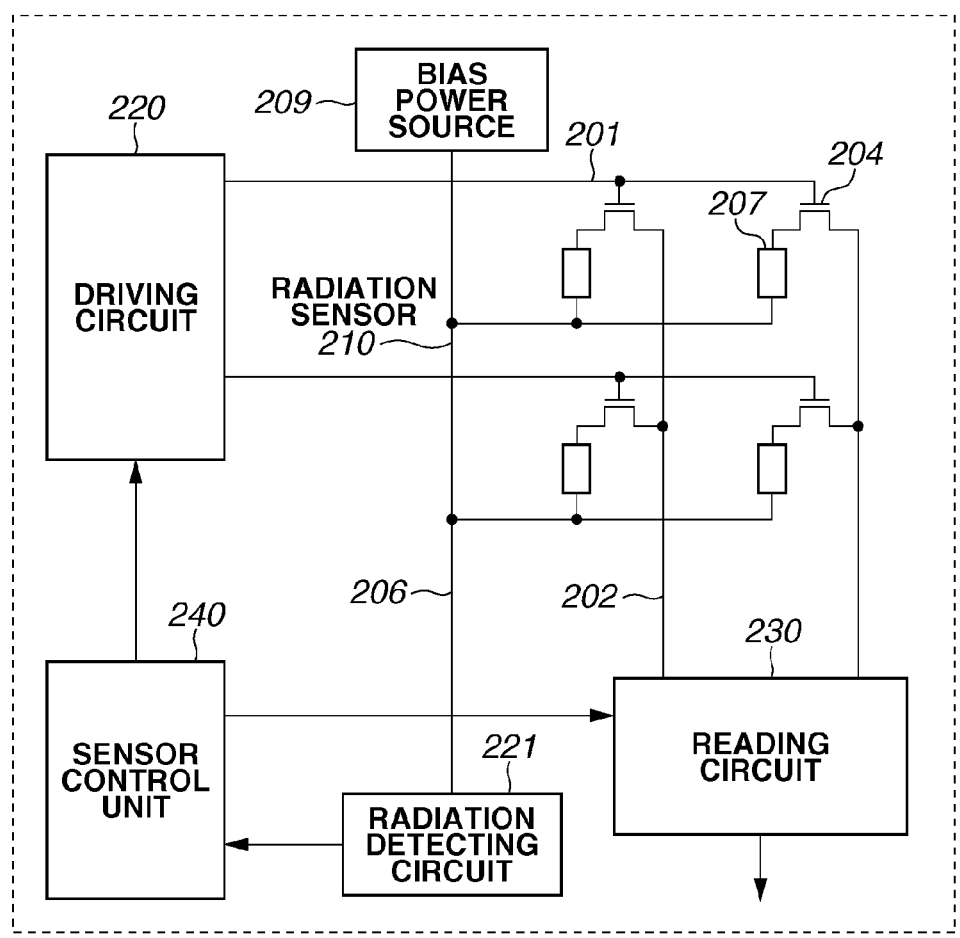
FIG. 2 illustrates a configuration example of a radiation sensor and a peripheral circuit thereof according to an exemplary embodiment.

FIG. 2 illustrates a configuration example of the radiation sensor 210 and a peripheral circuit thereof. To simplify the description, FIG. 2 illustrates a two-dimensional sensor including a plurality of pixels disposed in a two-dimensional matrix pattern of 2 rows×2 columns, as a part of a solid-state image sensor of the radiation sensor 210. An actual X-ray sensor includes numerous pixels disposed in such a way as to constitute a matrix pattern of several thousands of rows× several thousands of columns. In this case, the number of rows and the number of columns are not limited to specific numbers. The number of pixels can be arbitrarily determined. Further, as another exemplary embodiment, a phosphor capable of converting radioactive rays into visible light can be laminated on the solid-state image sensor. In another example, the solid-state image sensor itself has the capability of converting radioactive rays into an electric signal.

Each pixel of the radiation sensor 210 includes a photoelectric conversion element 207 and a thin film transistor (TFT) 204 connected to one end of the photoelectric conversion element 207. A bias power source 209 is connected to the other end of the photoelectric conversion element 207 via a bias line 206. The TFT 204 is functionally operable as a switch element capable of selectively connecting or disconnecting the photoelectric conversion element 207 to or from a column signal line 202. The TFT 204 has a base electrode connected to a common row selection line 201. The driving circuit 220 can control the TFT 204 via the common row selection line 201.

For example, the driving circuit 220 includes a shift register that can sequentially output signals in one direction so that a voltage can be applied to each row selection line 201 in synchronization with an input clock pulse and the TFT 204, connected to the row selection line 201, turns on in response to the applied voltage. The operation for applying a voltage to turn on the TFT 204 is referred to as "row selection." Sequentially performing the row selection is referred to as scanning of the radiation sensor 210. According to the example illustrated in FIG. 2, the above-mentioned reading mode (or the reading state) is the state where the scanning is sequentially performed. Further, according to the example illustrated in FIG. 2, the above-mentioned storage mode (or the storage state) is the state where each TFT 204 to be used in the generation of an image is held in an OFF state.

The photoelectric conversion element 207 is, for example, a charge coupled device (CCD) or an appropriate element made of amorphous silicon or polysilicon. In the above-described element, it is generally known that storage of electric charges occurs due to dark current even in a non-irradiation state, irrespective of photoelectric conversion method thereof. The electric charges if stored due to the dark current cause noises especially in an imaging operation performed with a small signal.

The electric charges if derived from the dark current not only deteriorate the image quality but also reduce the sensitivity of the photoelectric conversion element 207. Therefore, even in a non-signal state, periodically performing a reset operation for the element is required to remove the electric charges derived from the dark current. However, a desired image cannot be obtained by performing generation of X-rays while the reset operation is performed because no electric charge can be stored. The reset operation is feasible, for example, in the reading mode using the TFT 204. Further, as another example, it is feasible to connect both the TFT 204 and a reset TFT to the photoelectric conversion element.

An electric signal, if it is read via the column signal line from the radiation sensor 210, is input to the reading circuit 230. The reading circuit 230, for example, includes an amplifier and an AD converter. The reading circuit 230 amplifies an analog electric signal having been read and converts the amplified signal into a digital value to obtain digital radiation image data. An actual digital radiation image data includes data corresponding to dark electric charges that may be generated even when the photoelectric conversion element 207 receives no radiation in addition to data corresponding to electric charges obtained by the photoelectric conversion element 207 according to the generation of radioactive rays. Therefore, the reading circuit 230 includes a dark current correction circuit that can correct a dark current data component corresponding to the dark electric charges. Further, the reading circuit 230 can include a gain correction circuit that can correct the dispersion in sensitivity of each pixel and a defective pixel correction circuit that can correct defective pixels.

A driving operation that can be realized with the radiation detecting circuit 221 is described in detail below. The sensor control unit 240 controls the driving circuit 220 to perform a scanning operation for turning on TFTs 204 of each row or every predetermined number of rows for a predetermined period. When the driving circuit 220 supplies a pulse signal to the TFT 204, the TFT 204 turns on for a predetermined period of time. The scanning order of respective TFTs 204 and the number of rows of TFTs 204 to be turned on simultaneously can be arbitrarily determined.

The driving circuit 220 continuously performs scanning processing under the control of the sensor control unit 240, until the generation of X-rays can be detected. When the driving operation has been completed for all scanning lines, an X-ray imaging apparatus 101 restarts the driving operation from the scanning line driven initially.

While the X-ray imaging apparatus 101 performs the driving operation for respective scanning lines, the radiation detecting circuit 221 converts the current flowing through the bias line 206 connected to the bias power source 209 into a digital value via a current-voltage conversion circuit, an amplifier, an AD converter, and a signal processing circuit. Then, a comparator compares the digital value with a predetermined threshold value and outputs a signal indicating the comparison result, as an X-ray irradiation detection signal, to the sensor control unit 240. If the digital value exceeds the predetermined threshold value, the sensor control unit 240 can determine that there is a change in the current flowing through the bias line 206 and can identify the generation of X-rays. Further, the radiation detecting circuit 221 sequentially stores the converted digital value in a storage circuit. A state in which the X-ray imaging apparatus performs the above-mentioned operation corresponds to an X-ray irradiation detection state. The bias power source 209 supplies a bias voltage to the photoelectric conversion element 207.

The frequency of sampling to be performed by the AD converter can be arbitrarily set. For example, it is feasible to perform sampling operations a plurality of times when the TFTs 204 belonging to the same scanning line are turned on. However, in data processing, it is desirable to finally obtain one digital value for each row through averaging or comparable processing. Further, to enhance the robustness against extrinsic noises, it is desired to perform a correlated double sampling operation to calculate a difference between a digital value acquired in a turned-on state of the TFTs 204 belonging to the same scanning line and a digital value acquired in a turned-off state of the same TFTs 204. In this case, the digital value is sequentially updated in synchronization with the scanning processing. Therefore, the storage circuit is required to sequentially overwrite the digital value and have a storage capacity sufficient to store one digital value for each scanning line.

When an X-ray bulb tube 102 generates X-rays, the photoelectric conversion element 207 causes electric charges due to light emission from a phosphor layer (not illustrated). The generated electric charges flow into the bias line 206 and cause a change in the current flowing through the bias line 206. The radiation detecting circuit 221 detects the change in the current value via the above-mentioned circuit (i.e., the current-voltage conversion circuit, the amplifier, the AD converter, and the signal processing circuit) and outputs an instruction to stop the above-mentioned scanning processing to the sensor control unit 240.

Thus, the X-ray sensor unit 201 transits into a state where electric charges caused by the generation of X-rays are stored. Upon termination of the scanning processing, the storage circuit stops updating the digital value and holds the latest digital value. The sensor control unit 240 stores scanning line position information (e.g., a scanning line number identifying the scanning line at which the scanning processing has been stopped) in a register (not illustrated). The scanning line position information is not limited to the scanning line number and any other information is usable if it is possible to identify the scanning stop position.

The driving circuit 220 controls various operational states (including reset, radiation detection driving, electric charge storage, and reading states) of the sensor based on an instruction from the sensor control unit 240. The operation for storing electric charges is equivalent to an imaging operation for capturing an X-ray image of a photographic subject and may be referred to as "imaging operation" in the following description.

In the present exemplary embodiment, the current flowing through the bias line 206 is used to detect the generation of X-rays. However, it is unnecessary to use the current flowing through the bias line 206 if the current flowing through an internal component of the X-ray imaging apparatus 101 is usable to detect a change in the current value occurring due to the generation of X-rays.

A configuration example of the radiographic imaging system is described in detail below with reference to FIG. 3. According to the example illustrated in FIG. 3, a portable radiographic imaging apparatus 200 includes the radiation sensor 210, the driving circuit 220, the reading circuit 230, the sensor control unit 240, the memory 280, and a battery 290, which are accommodated in a casing. The sensor control unit 240 includes the display control unit 271, the timer 242, the determination unit 241, and the setting unit 260 to perform predetermined functions in addition to the above-mentioned imaging control functions. The sensor control unit 240 can be, for example, packaged as a single FPGA or a plurality of FPGAs. The battery 290 is a power source that can supply electric power to each component provided in the radiographic imaging apparatus 200.

According to an exemplary embodiment, a separate notification unit 600 is connected via a cable or wirelessly to the radiographic imaging apparatus 200. The notification unit 600 is an example of an indicator relating to the radiographic imaging operation using the radiation sensor 210. The notification unit 600 is provided in such a way as to enable an operator to confirm the operational state of the radiographic imaging apparatus 200 even when the display unit 270 is disposed on a side surface of the casing of the radiographic imaging apparatus 200 and is concealed by a subject person, for example, when the subject person lies on a bed and the radiographic imaging apparatus 200 is disposed on the back side of the subject person.

The notification unit 600 includes a notification display unit 610, a notification light-emitting unit 620, a notification sound generation unit 630, and a notification control unit 640. The notification display unit 610 is configured to cause a liquid crystal display device to display information (including character strings and icons). The notification light-emitting unit 620 is configured to control a light-emitting pattern of an LED to notify an operational state of the radiographic imaging apparatus 200. The notification sound generation unit 630 is configured to cause a speaker to generate various sounds. The notification control unit 640 is configured to control the above-mentioned units.

More specifically, the notification control unit 640 can receive, via a wired or wireless connection, a first signal indicating the commencement of a standby time clocking operation and a second signal indicating the passage of the clocked standby time. Further, the notification control unit 640 causes the notification unit 600 to output a predetermined notification according to the time left before the standby time having been set by the setting unit 260 elapses. In addition, the notification control unit 640 causes the notification unit to output another notification instructing the operator to start an irradiation operation in response to the passage of the standby time. As mentioned above, providing the separate notification apparatus is useful in that the operator can confirm the irradiation timing at an arbitrary position distant from an X-ray detection apparatus.

Figure 4:
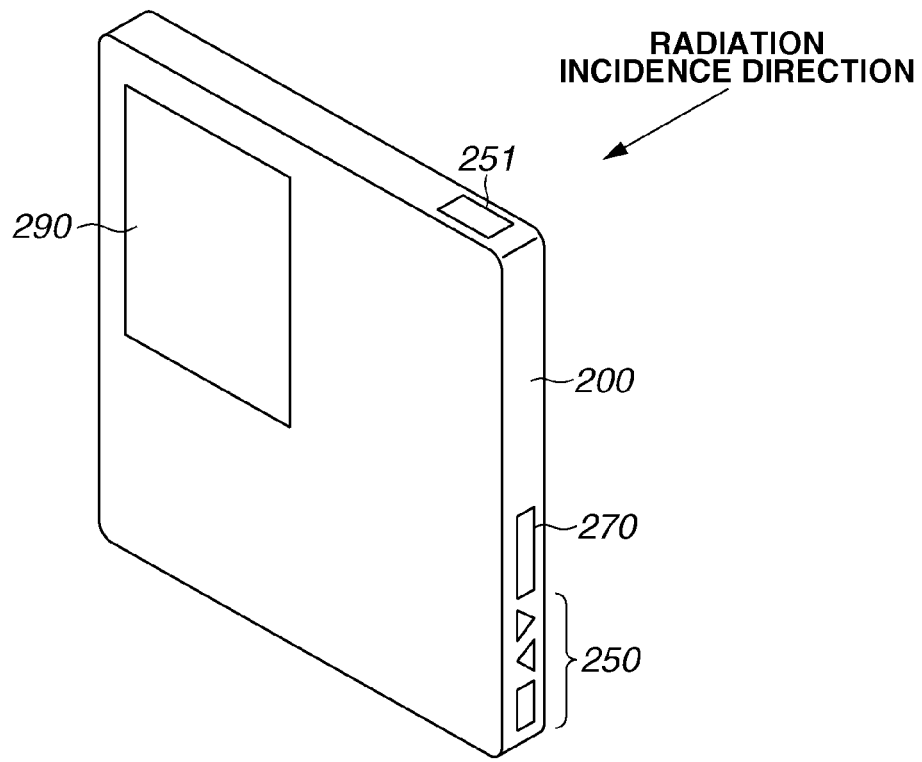
FIG. 4 illustrates an appearance of the portable radiographic imaging apparatus according to an exemplary embodiment.

FIG. 4 illustrates an appearance of the portable radiographic imaging apparatus 200 according to the present exemplary embodiment. A planar casing has a first side surface on which the operation unit 250 and the display unit 270 are disposed. The operation unit 250 includes two selection buttons and a confirmation button for confirmation of input information. Further, the operation unit 250 includes a power source button 251 that is operable to turn on or off the power source of the radiographic imaging apparatus 200. The power source button 251 is provided on a side surface that is different from the first side surface on which the operation unit 250 is provided. The battery 290 is detachably provided on a reverse face of the casing, which is opposed to a radiation incidence face in a radiation incidence direction.

The setup position of the operation unit 250 (or any other member) is not limited to the example illustrated in FIG. 4 and can be arbitrarily changed within a range in which no adverse influence is given to the imaging operation.

Further, according to another example, the operation unit 250 and the display unit 270 can be provided on a remote controller apparatus that is separated from the radiographic imaging apparatus 200. In this case, the remote controller apparatus is configured to output an infrared signal that can be received by an infrared communication unit provided on the radiographic imaging apparatus 200. Thus, an operator can easily perform operation settings even after the radiographic imaging apparatus 200 is positioned at an appropriate place.

Further, according to another example, a remote controller can be configured to include the operation unit 250, the display unit 270, a wireless communication circuit, the battery 290, and a casing accommodating these members. When the remote controller is detached from the radiographic imaging apparatus 200, the wireless communication circuit of the remote controller communicates with a wireless communication circuit of the radiographic imaging apparatus 200 to transmit and receive operation signals via the wireless communication circuits thereof to enable a user of the remote controller to operate the radiographic imaging apparatus 200.

Further, in a case where the remote controller is attached to the radiographic imaging apparatus 200, electric power can be supplied to the battery 290 of the remote controller via metal terminals so that the remote controller can be easily handled. The usability of the detachable remote controller can be further improved if the remote controller is configured to have the above-mentioned functions of the notification unit 600.

An example of the imaging operation that can be performed by the radiographic imaging system having the above-mentioned configuration is described in detail below with reference to FIG. 5. The following example is an operation to be performed in an imaging mode in which an operator checks the timer and the display content of the display unit to synchronize the radiation generation timing with the radiographic imaging timing obtained by the radiation sensor 210.

First, in step S100, the radiation generating apparatus 100 starts an operation. Next, in step S110, the generation control circuit 130 of the radiation generating apparatus 100 sets X-ray irradiation conditions according to an operational input signal from the generator operation unit 145 that is connected to the radiation generating apparatus 100. For example, the X-ray irradiation conditions include various parameters relating to the X rays to be generated (e.g., tube current, tube voltage, and irradiation time) and an irradiation range that is dependent on the distance between the radiation throttle 111 and the radiation sensor 210 or a subject.

The radiation throttle 111 can be configured to operate together with the generator operation unit 145 or can be configured to be manually adjustable. If the generation control circuit 130 completes the setting of X-ray irradiation conditions, then in step S120, the generation control circuit 130 repetitively performs processing for determining whether the irradiation switch 140 has been pressed. If it is determined that the irradiation switch 140 has been pressed (YES in step S120), the operation proceeds to step S130. The generation control circuit 130 controls the high-voltage power source 120 to cause the radiation source 110 to generate radioactive rays. Then, in step S135, the generation control circuit 130 repetitively performs processing for determining whether the next imaging operation to be continuously performed is scheduled.

If it is determined that the next imaging operation is not performed (NO in step S135), the generation control circuit 130 terminates the processing of the left part of the flowchart illustrated in FIG. 5. If it is determined that the next imaging operation to be continuously performed is scheduled (YES in step S135), the operation returns to step S110 in which the generation control circuit 130 newly sets irradiation conditions.

While the radiation generating apparatus 100 performs the above-mentioned operation, the imaging system including the radiation sensor 210 is activated and starts an operation. In step S200, the imaging system selects an imaging mode based on an external signal or an operational instruction input via the operation unit 250, or based on default setting information. According to the example illustrated in FIG. 5, the imaging mode selected in step S200 is the timer based imaging mode.

Next, in step S210, the setting unit 260 sets a standby time for imaging based on the operational instruction input via the operation unit 250. The standby time to be set in step S210 is the amount of time left before the imaging operation actually starts after an imaging start button is pressed (see step S220). For example, the irradiation switch 140 may be located at a position distant from the imaging system. In such a case, if the standby time is appropriately set, the operator can manipulate the irradiation switch 140 in good time after completing the positioning of the imaging system and the subject. On the other hand, if a short standby time is set, it may be relatively easy for the operator to control the irradiation timing. In this manner, the operator can set optimum imaging timing for the imaging operation to be performed considering momentary situation. The setting value of the standby time is input to the timer 242 that clocks the standby time and to the determination unit 241 and further input to the display control unit 271 to display the remaining standby time.

In step S215, the setting unit 260 sets a accumulation time in addition to the standby time. The accumulation time is the amount of time that determines the period of time during which the TFT 204 of the radiation sensor 210 is brought into OFF state after the standby time elapses. If a long accumulation time is set, the imaging system can perform a radiographic imaging operation even when the irradiation time is long. Further, if the imaging operation using the timer 242 is performed, it may be easy for the operator to set timing.

On the other hand, if a short accumulation time is set, the dynamic range and the image quality can be improved because the accumulation time of dark current becomes shorter. The setting unit 260 sets the accumulation time according to an operational instruction input via the operation unit 250 considering momentary situation. The setting value of the accumulation time is input to the sensor control unit 240 and is usable in the driving control of the driving circuit 220.

After completing the above-mentioned setting operations, in step S220, the determination unit 241 repetitively performs processing for determining whether the imaging start button has been pressed. The imaging start button is, for example, provided on the operation unit 250. When the imaging start button is pressed, the operation unit 250 outputs an instruction signal to the determination unit 241 to cause the timer 242 to start the standby time clocking operation.

In another imaging mode, for example, when the radiation detecting circuit 221 detects the generation of radioactive rays, the detection circuit 221 starts irradiation start determination processing according to a imaging start instruction. If the imaging apparatus performs an imaging operation using the radiation generating unit IF 222, the imaging apparatus causes the sensor to perform standby driving processing while repeating the storage mode and the reading mode. Further, the imaging apparatus waits for an irradiation permission request signal via the radiation generating unit IF 222. The imaging apparatus performs the above-mentioned operation when the standby time is set to be a positive value. When the standby time is set to 0, the imaging apparatus skips the standby time clocking processing (i.e., the processing to be performed in step S240) and instructs the sensor control unit 240 to start a storage operation.

In step S240, in response to the input instruction signal, the determination unit 241 and the timer 242 start clocking the standby time. Meanwhile, the display control unit 271 causes the display unit 270 to display the remaining standby time and sequentially update the display content. In this case, the timer 242 can be activated in response to an imaging instruction or can start sampling the clocks output from the clock pulse generator currently operating. The timer 242 sequentially outputs counter values. The determination unit 241 continuously performs processing for determining whether the standby time elapses since the reception of the imaging start instruction signal based on the counter value.

The display control unit 271 appropriately calculates the remaining time with reference to the counter value output from the timer 242 and causes the display unit 270 to display the remaining time. Alternatively, in addition to the above-mentioned standby time passage determination, the determination unit 241 can compare the standby time with the elapsed time to determine the remaining time. In this case, for example, the display control unit 271 receives the remaining time information from the determination unit 241 and causes the display unit 270 to display the remaining time. For example, the time left before starting the imaging operation can be displayed on the display unit 270 as illustrated in FIG. 6D while the timer 242 performs a countdown operation. In this case, the countdown display can be realized, for example, by using an appropriate LED lighting pattern and sounds.

If the standby time elapses, then in step S241, the sensor control unit 240 brings the radiation sensor 210 into the storage state via the driving circuit 220. In a case where the sensor control unit 240 performs predetermined initialization processing (for example, for stabilizing the radiation sensor 210 by repeating the reading mode and the storage mode predetermined number of times) before bringing the radiation sensor 210 into the storage state, the sensor control unit 240 performs the initialization processing while countdown display processing is performed in step S240 so that the storage operation can be immediately started upon termination of the standby time.

In step S250, the display control unit 271 causes the display unit 270 to display a message "the generation of X-rays is feasible" according to the passage of the standby time and the starting of the storage processing. The display content displayed in step S250 indicates that the radiation sensor 210 can detect radioactive rays and the imaging apparatus can obtain a radiation image while the radiation generating apparatus 100 generates the radioactive rays.

Further, the display content indicates that the storage period of the radiation sensor 210 can include a radioactive ray irradiation period if it is less than a predetermined irradiation time. In this case, in addition to or instead of the display of the display unit 270, the separate notification unit 600 illustrated in FIG. 3 can perform a similar display operation, for example, in a case where the portable radiographic imaging apparatus 200 is located on the behind side of a recumbent subject. The operator can easily determine the imaging timing because the driving status of the radiation sensor 210 can be known.

In step S255, the display control unit 271 continuously perform an irradiation feasibility display during the accumulation time having been set and terminates the display before the storage processing terminates.

For example, the display unit 270 is controlled to terminate the display prior to termination of the storage period so that the generation of radioactive rays terminates within the storage period even when the radiation generating apparatus 100 starts generating radioactive rays immediately before the display unit 270 terminates the display indicating the permissibility of generating radioactive rays. For example, if a permissible radioactive ray irradiation time is 300 milliseconds when the accumulation time is 3000 milliseconds, the display control unit 271 performs a display control in such a way as to cause the display unit 270 to terminate the display at the time when 2700 milliseconds has elapsed since the commencement of the storage processing.

As mentioned above, the display control unit 271 and the sensor control unit 240 operate cooperatively in such a way as to set the period of time during which the display unit 270 performs a display indicating the permissibility of radiographic imaging operation to be longer than the period of time during which the storage operation using the radiation sensor 210 is performed. The above-mentioned setting is useful to reduce the possibility of causing an ineffective exposure that may occur when the period of time during which the radiation generating apparatus 100 generates radioactive rays exceeds the storage period.

In this case, for example, the setting unit 260 can be configured to set a period of time during which the display unit 270 continuously displays the permissibility of radiographic imaging operation, instead of setting the accumulation time. In this case, the usability of the system can be improved for the operator because starting of the generation of radioactive rays can be permitted by the period of time having been set via the operation unit 250.

Alternatively, the setting unit 260 can be configured to acquire the accumulation time and the generation time of radioactive rays according to an operational instruction input via the operation unit 250 and calculate the period of time during which starting of the generation of radioactive rays can be permitted. The display control unit 271 can be configured to cause the display unit 270 to display the calculated information. In this case, it becomes easy for the operator to determine the imaging timing.

The operator confirms the display content and presses the irradiation switch 140 while the display unit 270 continuously display the information. The radiation generating apparatus 100 generate X-rays (see steps S120 and S130). Subsequently, in step S260, the sensor control unit 240 causes the radiation sensor 210 to terminate the storage operation and activates the reading circuit 230 to obtain radiation image data. In step S270, an image processing circuit performs sensor characteristics correction processing (e.g., dark current correction, gain correction, and defective correction) on radiation image data. The image processing circuit is, for example, packaged together with the sensor control unit 240 on the FPGA.

Further, the image processing circuit can perform quality enhancing processing (e.g., gradation conversion, dynamic range compression processing, and noise reduction processing). Subsequently, in step S280, the display unit 270 or the image confirmation terminal 275 displays the processed radiation image data. Subsequently, in step S285, the sensor control unit 240 determines whether the next imaging operation to be continuously performed is scheduled. If it is determined that the next imaging operation to be continuously performed is scheduled (YES in step S285), the operation returns to step S210 to perform the standby time setting processing again. If it is determined that the next imaging operation is not performed (NO in step S285), the sensor control unit 240 terminates the processing of the right part of the flowchart illustrated in FIG. 5. For example, it is useful that the sensor control unit 240 checks whether the button of the operation unit 250 has been pressed in determining the continuation of the imaging operation.

As mentioned above in the present exemplary embodiment, in a system where the X-ray irradiation timing and the imaging timing are not electrically synchronized, it is important to explicitly notify a user of the period of time during which the irradiation using X rays is feasible, more specifically, the period of time during which the storage operation is performed. If the notification timing deviates from the actual storage timing, the generation of X-rays may be performed inappropriately and a imaged patient may be unnecessary exposed to X-rays. To solve such a problem, it is useful to start an irradiation feasibility display operation after commencing the storage and terminate the irradiation feasibility display before terminating the storage operation, so that the storage operation can be surely performed within the irradiation feasibility display period.

By employing the above-mentioned configuration, the X-ray generation timing can be surely synchronized with the X-ray imaging timing when an imaging operation is performed to obtain an X-ray image.

A configuration example of the operation unit 250 and the notification unit 270 is described in detail below with reference to FIG. 6. When an operational instruction is input via the operation unit 250, the setting unit 260 sets the input operational instruction as an operation condition of the radiographic imaging apparatus 200. According to the example illustrated in FIG. 6, the operation unit 250 includes three types of buttons. Two of these buttons are operable to select a numerical value or a character. The user can press these buttons to select a numerical value or a character to be input. The setting unit 260 stores information about the selected numerical value or the selected character in a temporary memory and appropriately updates the stored information. Further, in response to an input, the display control unit 271 causes the display unit 270 to display the presently selected numerical value or character with reference to the temporary memory.

The remaining button of the operation unit 250 is operable to finalize the input numerical value. In response to the finalized determination, the setting unit 260 sets the presently selected numerical value or the character as an operation condition. Therefore, the user operates the operation unit 250 to select a desired numerical value or character, confirms the display content of the display unit 270, and presses the operation unit 250 to determine setting values.

Figure 6A:
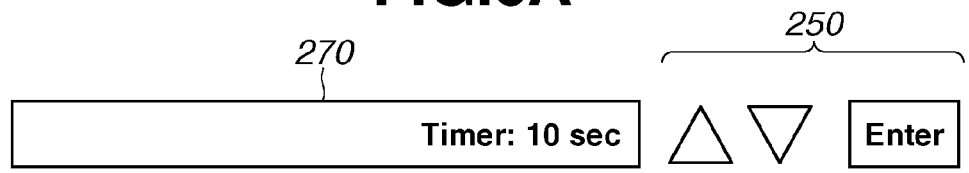
FIGS. 6A to 6E illustrate example screen displays that can be performed by an operation unit and a display unit according to an exemplary embodiment.

FIG. 6A is a setting screen that enables the user to input an operational instruction relating to a waiting time for the imaging operation, which corresponds to the setting processing to be performed in step S210. When the user presses an Enter button of the operation unit 250, the setting unit 260 finalizes the setting value about the standby time.

Figure 6B:
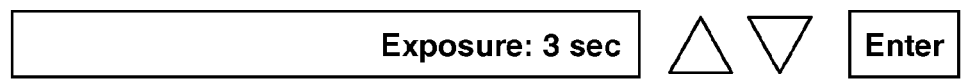

FIG. 6B is a screen that enables the user to input an operational instruction, which corresponds to the accumulation time setting processing to be performed in step S215. When the user presses the Enter button of the operation unit 250, the setting unit 260 finalizes the setting value about the accumulation time.

Figure 6C:
Figure 6D:

FIG. 6C is a screen that enables the user to input an operational instruction, which corresponds to the imaging start instruction to be input in step S220. When the user presses the Enter button of the operation unit 250, the operation unit 250 outputs an instruction signal to the determination unit 241. The instruction signal instructs the determination unit 241 to start the standby time clocking operation.

Figure 6E:

FIG. 6D illustrates a countdown display to be displayed on the display unit 270 in step 240. FIG. 6E illustrates a display content indicating that starting the generation of radioactive rays is permissible, which can be displayed in step S250.

The display unit 270 is not limited to a display example illustrated in FIG. 6. For example, controlling a lighting pattern using a plurality of LEDs is employable. Alternatively, the above-mentioned display device can be replaced by a speaker. Further, the operation unit 260 can include a scroll wheel, a dial, a barcode reader, and a microphone (i.e., a speech sound input unit). Further, the operation unit 260 can include a push button and a touch panel sensor. Further, each of the display unit 270 and the operation unit 250 can be configured as a touch panel display device so that the user can operate GUI buttons displayed on the display unit 270.

FIG. 7 is a flowchart illustrating operation mode setting processing, which is pre-processing to be performed before starting the processing of step S210 in the flowchart illustrated in FIG. 5.

In step S2001, the sensor control unit 240 activates the operation unit 250, the setting unit 260, the display control unit 271, and the display unit 270. Further, the sensor control unit 240 causes the bias power source 209 to supply electric power to the radiation sensor 210. Further, the sensor control unit 240 causes the bias power source 209 to supply electric power to the driving circuit 220. Alternatively, the sensor control unit 240 can be configured to cause the bias power source 209 to supply no electric power to the radiation sensor 210 at this timing.

In step S2002, the operation unit 250 receives an operational input instructing the imaging mode from the operator. For example, the operation unit 250 includes a plurality of buttons dedicated to respective imaging modes so that the operator can instruct a desired operation mode by pressing the dedicated button. In step S2003, the setting unit 260 determines whether the instructed operation mode is a synchronization mode. If it is determined that the instructed operation mode is not the synchronization mode (NO in step S2003), then in step S2004, the setting unit 260 determines whether the instructed operation mode is an automatic triggering mode. If it is determined that the instructed operation mode is not the automatic triggering mode (NO in step S2004), then in step S2005, the setting unit 260 determines that the instructed operation mode is a manual synchronization mode, i.e., an imaging mode using the timer 242.

Thus, in step S2005, the sensor control unit 240 starts an operation in the manual synchronization mode. The processing to be performed in step S2005 is, for example, similar to the processing described with reference to the flowchart illustrated in FIG. 5. In step S2006, the setting unit 260 repetitively performs processing for determining whether a mode change instruction has been input. If it is determined that the change instruction has been input (YES in step S2006), the operation returns to step S2003. If it is determined that the change instruction has not been input (NO in step S2006), then in step S2007, the setting unit 260 determines whether to terminate the imaging operation, for example, based on an operational instruction input via the operation unit 250. If it is determined that the imaging operation does not terminate (NO in step S2007), the operation returns to step S2005 to continue the operation in the manual synchronization mode.

On the other hand, if it is determined that the instructed operation mode is the synchronization mode (YES in step S2003), then in step S2008, the sensor control unit 240 starts a imaging mode operation using the radiation generating unit IF 222. In this case, for example, the setting unit 260 or the sensor control unit 240 transmits a Ping signal to the radiation generating unit IF 222 to confirm connection of the radiation generating unit IF 222 and activation of the power source, and further confirm the connection to the radiation generating apparatus 100 via the radiation generating unit IF 222. If the connection has been confirmed, the radiographic imaging system performs an operation in the synchronization mode via the radiation generating unit IF 222.

In step S2009, the setting unit 260 determines whether there is any problem (or error) in the synchronization mode operation. For example, the connection between the radiation generating unit IF 222 and the sensor control unit 240 may not be confirmed. If it is determined that there is not any problem (NO in step S2009), the radiographic imaging system continues the operation. If there is a problem (YES in step S2009), the radiographic imaging system determines that the operation in the synchronization mode is impossible. The setting unit 260 sets the manual synchronization mode.

Even when the imaging operation cannot be performed in the synchronization mode, by employing the above-mentioned configuration, the radiographic imaging system can perform the radiographic imaging operation without waiting until the repair is completed or the problem is solved. Therefore, the above-mentioned configuration is useful in a case where the radiographic imaging operation needs to be urgently accomplished.

For example, the radiographic imaging system determines that continuing the synchronization mode operation is impossible if the connection between the radiation generating unit IF 222 and the radiation generating apparatus 100 cannot be confirmed. For example, in a case where the radiation generating unit does not include any interface that can communicate with the radiation generating unit IF 222, it is believed that these apparatuses are simply disconnected or electrically disconnected although they are physically connected.

In this case, if the display control unit 271 causes the display unit 270 to display the content of a problem according to the type of the problem, the operator can confirm the system configuration and solve the problem. Further, if the radiographic imaging system is configured to change the operation mode from the synchronization mode to the manual synchronization mode in response to a mode change acknowledgment signal input from the operation unit 260, it is feasible to prevent the system from operating in an unintended imaging mode and reduce the possibility of causing an erroneous imaging operation.

Mode change determination processing to be performed in step S2010 and termination determination processing to be performed in step S2011 are similar to those in step S2006 and S2007. Therefore, redundant description thereof will be avoided.

If it is determined that the instructed operation mode is the automatic triggering mode (YES in step S2004), then in step S2012, the radiographic imaging system starts a imaging mode operation using the radiation detecting circuit 221. The sensor control unit 240 starts supplying electric power to the radiation detecting circuit 221 and, if necessary, causes the radiation sensor 210 to start driving. In step S2013, the setting unit 260 determines whether there is any problem in the automatic triggering mode operation. For example, the radiation detecting circuit 221 may malfunction. If it is determined that there is not any problem (NO in step S2013), the radiographic imaging system continues the operation. If there is a problem (YES in step S2013), the radiographic imaging system determines that the operation in the automatic triggering mode is impossible. The setting unit 260 sets the manual synchronization mode.

Even when the imaging operation cannot be performed in the automatic triggering mode, by employing the above-mentioned configuration, the radiographic imaging system can perform the radiographic imaging operation without waiting until the repair is completed or the problem is solved. Therefore, the above-mentioned configuration is useful in a case where the radiographic imaging operation needs to be urgently accomplished.

For example, the radiographic imaging system determines that continuing the automatic triggering mode operation is impossible if the radiation detecting circuit 221 cannot detect the start of the irradiation. If the dose of radiation to be generated is extremely low, or when the irradiation time is extremely short, it may be difficult for the radiation detecting circuit 221 to detect the start of the generation of radioactive rays at appropriate timing. In such a case, it is desired that the radiographic imaging system operates in the synchronization mode or in the manual synchronization mode.

For example, the setting unit 260 checks the compatibility between the imaging mode and irradiation conditions input via the operation unit 260 by determining whether the irradiation conditions are suitable for the operation in the automatic triggering mode. Further, if the remaining power amount of the battery 290 is equal to or less than a predetermined threshold value, it is feasible to prohibit the automatic triggering mode that requires a large amount of electric power consumption and shift the operation mode to the manual synchronization mode to perform many imaging operations even when the remaining power amount is small.

Mode change determination processing to be performed in step S2014 and termination determination processing to be performed in step S2015 are similar to those in step S2006 and S2007. Therefore, redundant description thereof will be avoided.

In this case, after the imaging operation is performed in the manual synchronization mode, if there is information about the next imaging operation reserved, the setting unit 260 determines whether the operation mode is switchable to the automatic triggering mode or the synchronization mode. The mode switching determination can be performed by checking if there is any problem in the synchronization mode operation or in the automatic triggering mode operation, similarly to the above-mentioned processing. In this case, if it is determined that the synchronization mode operation is feasible without any problem, the setting unit 260 switches the mode setting from the manual synchronization mode to the synchronization mode. If it is determined that the automatic triggering mode operation is feasible without any problem, the setting unit 260 switches the mode setting from the manual synchronization mode to the automatic triggering mode. By employing the above-mentioned arrangement, the operator is not required to determine the timing and therefore the burden of the operator can be reduced.

According to another example, the manual synchronization mode is exclusively used as an emergency evacuation mode. For example, the manual synchronization mode is settable only when a user instruction is input via the operation unit 250. If the automatic triggering mode operation is feasible, the setting unit 260 automatically sets operation mode to the automatic triggering mode. Then, if the manual synchronization mode is instructed and the imaging operation is performed in the manual synchronization mode, the setting unit 260 switches the mode setting from the manual synchronization mode to the automatic triggering mode in response to completion of the imaging operation.

For example, in a case where there is a plurality of portions to be imaged in a single inspection, at the time when a first radiographic imaging operation is completed for the first portion to be imaged, the setting unit 260 switches the imaging mode from the manual synchronization mode to the automatic triggering mode to perform a second radiographic imaging operation for the second portion to be imaged. Performing the above-mentioned control is useful because the work to be performed by the user can be reduced and the imaging operation can be efficiently performed.

Setting information about the above-mentioned imaging mode having been set by the setting unit 260 is stored, for example, as a setting value in the memory 280. The setting value is stored in the memory 280 according to an operational instruction input via the operation unit 250. If it is determined that there is a problem and the operation according to the imaging mode having been set is infeasible, the setting unit 260 changes the setting value. It is unnecessary to immediately start the imaging operation according to each imaging mode after the mode has been set. For example, it is useful to start the imaging operation according to an operational instruction input via the operation unit 250.

In this case, the sensor control unit 240 refers to imaging mode setting value information and adds the imaging mode setting information to radiation image data obtained each time the imaging operation is performed. The radiation image data is associated with the setting information and stored in the memory 280. If the above-mentioned data set is transmitted to the external image confirmation terminal 275 or to an external apparatus, such as Picture Archiving and Communication Systems (PACS), it is feasible to confirm the imaging mode after completing the imaging operation. Alternatively, the image confirmation terminal 275 can be configured to give imaging mode setting value information.

As mentioned above, the operator can appropriately select one of a plurality of imaging modes for the imaging operation so that the radiographic imaging operation can be performed considering the situation.

Another exemplary embodiment of the present invention is described in detail below with reference to FIG. 8. The radiographic imaging system illustrated in FIG. 8 includes an imaging control apparatus 300, which is independent of the portable radiographic imaging apparatus 200. The timer 242 is provided in the imaging control apparatus 300. The imaging control apparatus 300 is functionally operable as a control apparatus of the radiographic imaging system serving as a modality. The imaging control apparatus 300 is an apparatus accommodated in a casing independent of the radiographic imaging apparatus 200. The imaging control apparatus 300 communicates with the radiographic imaging apparatus 200 via a physical or wireless connection.

Figure 8:
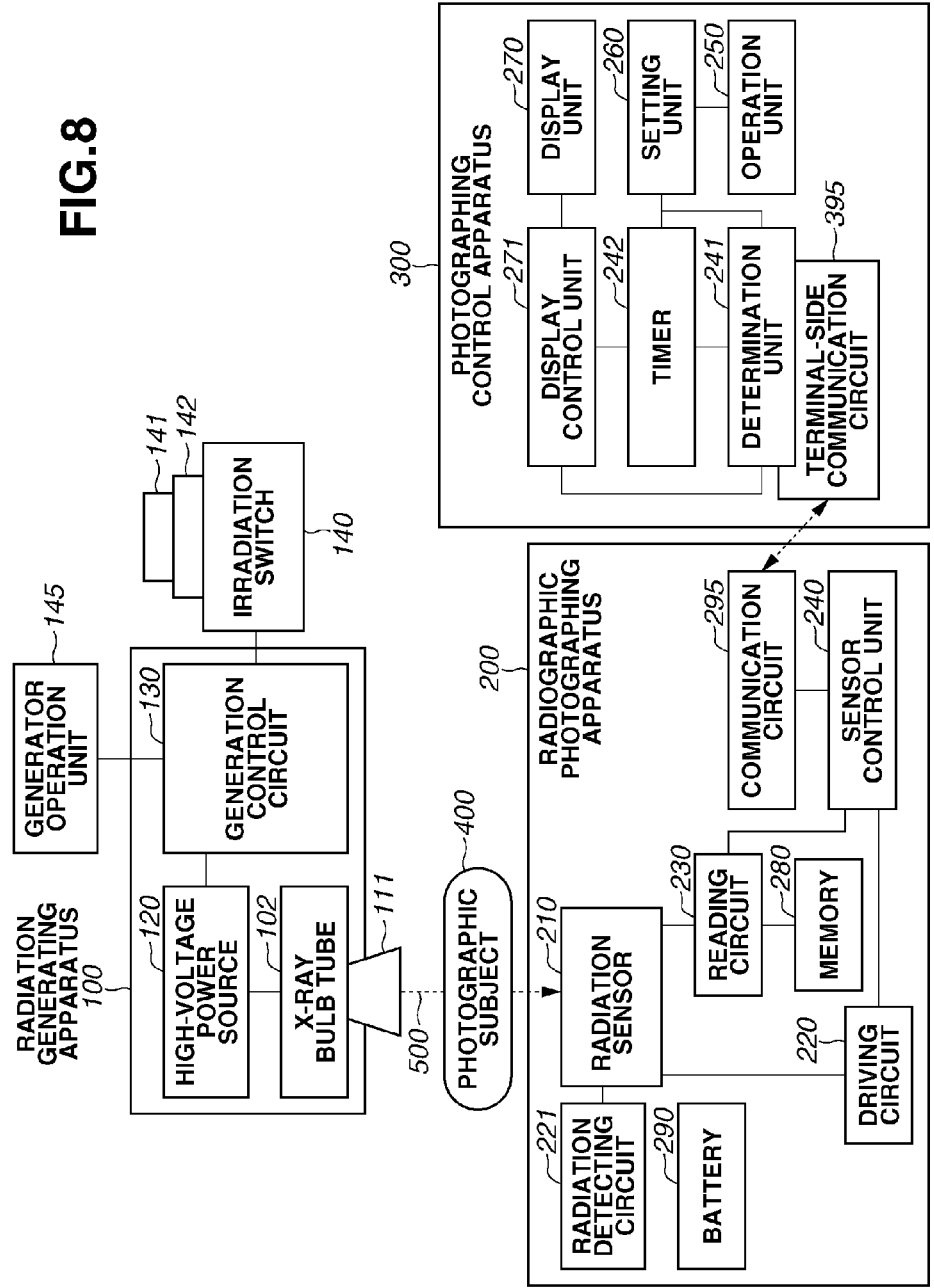
FIG. 8 illustrates a configuration example of a radiographic imaging system that includes an imaging control apparatus that is independent of a radiation sensor according to an exemplary embodiment.

The imaging control apparatus 300 illustrated in FIG. 8 is not only operable as a control apparatus for the radiographic imaging apparatus 200 but also operable as an irradiation condition control apparatus for the radiation generating apparatus 100. The imaging control apparatus 300 can be configured to receive information about the radiographic imaging order from a radiology information system (RIS), which is accessible via an in-hospital network, and transmit an image imaged by the PACS.

The imaging control apparatus 300 includes, for example, a central processing unit (CPU), a random access memory (RAM), a read only memory (ROM), a hard disk drive (HDD), and a communication circuit. A computer program including commands that realize the processing of a flowchart illustrated in FIG. 9 is stored in the ROM or the HDD. The CPU appropriately reads and executes the program to realize the functions of the imaging control apparatus 300. Constituent components of the configuration illustrated in FIG. 8 have functions similar to those of corresponding components, if they are the same in allocated number, unless otherwise mentioned. Therefore, redundant description thereof will be avoided.

In the imaging control apparatus 300, the operation unit 250 and the setting unit 260 are operable to perform various settings for the radiographic imaging apparatus 200 and further operable to control various operational states (e.g., reset, storage of electric charges, and reading operations). The display control unit 271 causes the display unit 270 to display setting values to perform various settings and the state of the radiographic imaging apparatus 200. Further, the display control unit 271 causes the display unit 270 to display an image captured by the radiographic imaging apparatus 200.

The imaging control apparatus 300 can be a dedicated unit. Alternatively, the imaging control apparatus 300 can be a general personal computer or a tablet-type computer on which a dedicated software program is installed. In the latter case, a keyboard or a mouse associated with the computer is usable as the operation unit 250. Alternatively, a unit including dedicated operation buttons can be connected to the operation unit 260. Further, a monitor connected to the computer is usable as the display unit 270. In addition, if the monitor includes a touch panel device, GUI buttons are usable as the operation unit 250.

As mentioned above, providing the imaging control apparatus 300 separated from the radiographic imaging apparatus 200 is useful in that various settings can be performed, for example, a setting can be made when the radiographic imaging apparatus 200 is located beneath a subject, or after completing the imaging preparation. Further, operations become easy.

In the present exemplary embodiment, the imaging control apparatus 300 includes a terminal-side communication circuit 395 that can communicate with a communication circuit 295 of the radiographic imaging apparatus 200. It is useful to use a dedicated interface and protocols for communications. For example, general communication protocols such as Ethernet (registered trademark) can be used. Further, proximity communication protocols such as Bluetooth can be used appropriately. Further, wired communications can be additionally used.

In a case where the imaging control apparatus 300 communicate with the RIS or the PACS, the imaging control apparatus 300 can use the terminal-side communication circuit 395. However, it is useful to provide another communication circuit that can communicate with the RIS or the PACS.

Further, in addition to the terminal-side communication circuit 395, the imaging control apparatus 300 can include a control circuit that can integrally control various units in the apparatus. Unless otherwise mentioned, operations mainly performed by the imaging control apparatus 300 are performed under the control of the control circuit.

The radiographic imaging apparatus 200 includes the communication circuit 295. The communication circuit 295 receives information about imaging mode, accumulation time, and standby time, which have been set by the setting unit 260, from the terminal-side communication circuit 395. Further, the communication circuit 295 transmits radiation image data obtained by the radiographic imaging apparatus 200 to the imaging control apparatus 300, so that the radiation image data can be displayed on the display unit 270.

FIG. 9 is a flowchart illustrating an X-ray imaging operation that can be performed by the radiographic imaging system illustrated in FIG. 8. The flowchart illustrated in FIG. 9 includes operations to be performed by the radiation generating apparatus 100, the radiographic imaging apparatus 200, and the imaging control apparatus 300. Processing contents that are similar to those illustrated in FIG. 5 are basically denoted using the same numbers and redundant description thereof will be avoided.

In step S115, the generation control circuit 130 repetitively performs processing for determining whether the first switch 141 of the irradiation switch 140 of the radiation generating apparatus 100 has been pressed. If it is determined that the first switch 141 has been pressed (YES in step S115), then in step S116, the radiation generating apparatus 100 causes the radiation source 110 to start a rotor-up operation for the bulb tube. In a case where the radiation source 110 uses a transmission-type target (not a rotary anode type target), the radiation generating apparatus 100 starts a predetermined preparatory operation (for example, for a cooling mechanism).

In this case, the rotor-up operation may require several seconds depending on the type of the bulb tube. In a case where the accumulation time is set to be extremely short, it may cause a significant delay if the first switch is pressed after the storage operation is started. In such a case, it is desired that the first switch 141 is pressed while countdown display processing is performed in step S340. Therefore, the display control unit 271 of the imaging control apparatus 300 causes the display unit 270 to display an indication to press the first switch 141 in addition to the countdown display. Therefore, the operator can press the first switch while viewing the display to synchronize the time to generate radioactive rays with the time to transit into the storage mode, while taking the time required for the generation apparatus to complete the preparatory operation into consideration.

In step S300, the imaging control apparatus 300 starts its operation. For example, the imaging control apparatus 300 communicates with the RIS according to an instruction from the operation unit 250 and acquires imaging order information. Subsequently, in step S310, the setting unit 260 of the imaging control apparatus 300 sets a standby time for the storage operation. Then, in step S315, the setting unit 260 sets the accumulation time.

In this case, the standby time is to be set according to situations or the operator. Therefore, the efficiency can be improved if the setting unit 260 is configured to set the standby type and the accumulation time according to the imaging order obtained from the RIS, because it becomes unnecessary to input an operational instruction via the operation unit 250.

For example, in a case where a subject person is required to hold the portable radiographic imaging apparatus 200 to image the leg of the subject person at a free position, it is desired to start the imaging operation immediately after the positioning is once completed. Therefore, the setting unit 260 sets a short standby time. Further, for example, in a case where imaging timing for a lung field needs to be synchronized with the breathing timing of the subject person, the setting unit 260 sets a longer standby time because a significant long time is required to adjust their timings.

If the operator has input setting values, the operator presses the imaging start button (see step S320). An imaging sequence starts in response to the pressing of the imaging start button. In step S230, the imaging control apparatus 300 performs countdown processing for the waiting time having been set. Detailed contents of the above-mentioned processing are similar to those of the processing illustrated in FIG. 5.

If the determination unit 241 determines that the waiting time having been set has elapsed, then in step S330, the imaging control apparatus 300 causes the terminal-side communication circuit 395 to transmit a storage start signal to the radiographic imaging apparatus 200. If the radiographic imaging apparatus 200 receives the storage start signal, then in step S241, the sensor control unit 240 starts storage processing. Subsequently, or substantially simultaneously, in step S235, the sensor control unit 240 causes the communication circuit 295 to transmit a reception notification signal to the imaging control apparatus 300. The reception notification signal notifies that the storage processing has been started in response to the storage start signal. In step S335, the terminal-side communication circuit 395 receives the reception notification signal. Then, in step S350, the display control unit 271 causes the display unit 270 to immediately perform the irradiation feasibility display operation.

The display control unit 271 controls display continuation time (i.e., display period) in such a way as to continue the irradiation feasibility display operation during the period of time obtainable by subtracting the time required to receive the reception notification signal after transmission of the storage start signal, from the accumulation time having been set. The above-mentioned processing can prevent the irradiation feasibility display operation from being performed before actually starting the storage processing and after terminating the storage processing. Therefore, it is feasible to reduce the possibility of ineffectively expose the subject person with radioactive rays at least when the irradiation switch 140 is pressed with reference to the display content.

In the imaging control apparatus 300, the timer 242 and the determination unit 241 monitor the time required until the reception notification signal is received after transmission of the storage start signal. For example, if it is determined that a storage start notification signal has not been received for a predetermined period of time, the imaging control apparatus 300 does not perform the irradiation feasibility display operation. There is a possibility that the storage processing cannot be started if a malfunction occurs in the radiographic imaging apparatus 200, for example, when the imaging control apparatus 300 cannot communicate with the radiographic imaging apparatus 200 due to abnormality of communication. Therefore, the imaging control apparatus 300 does not perform the irradiation feasibility display operation to reduce the possibility of causing an ineffective exposure.

In this case, only when the imaging start button of the operation unit 260 is pressed again, the terminal-side communication circuit 395 transmits the storage start signal. As mentioned above, if the determination unit 241 determines that there is an abnormality in communications, the imaging control apparatus 300 controls transmission timing in such a way as to transmit the storage start signal after waiting a predetermined time shorter than the standby time having been set beforehand.

Further, for example, it is useful to set the standby time to 0 so that the imaging control apparatus 300 can transmit the storage start signal immediately after the imaging start button is pressed. Employing the above-mentioned arrangement is useful in preventing the processing efficiency from decreasing or preventing the burden of the subject person from increasing, in particular, in a case where a long standby time is employed.

Further, the imaging control apparatus 300 can perform processing for shortening the standby time only when the standby time is longer than a predetermined threshold value. Alternatively, the display control unit 271 can cause the display unit 270 to display an operation button and a message that requests an acknowledgment for the operation to shorten the standby time. In this case, the imaging control apparatus 300 can change the standby time according to an operational instruction input via the operation unit 250, so that the operator can start the imaging operation at desired timing.

When the storage processing terminates (see step S260), the radiographic imaging apparatus 200 performs image processing and data transmission processing. The communication circuit 295 transmits the imaged radiation image data to the imaging control apparatus 300. In step S370, the imaging control apparatus 300 performs additional image processing, if necessary, on the transmitted radiation image data and stores the processing radiation image data in the memory. Further, in step S380, the display control unit 271 causes the display unit 270 to display the received image data. If it is determined that the next imaging operation to be continuously performed is scheduled (YES in step S285), the operation returns to step S310 to set the waiting time for the imaging operation again.

If it is determined that the next imaging operation is not performed (NO in step S285), namely when the termination of the imaging operation is instructed, all of the operations of the radiation generating apparatus 100, the radiographic imaging apparatus 200, and the imaging control apparatus 300 is stopped. In a case where the imaging control apparatus 300 is connected to the PACS, the imaging control apparatus 300 transmits one or a plurality of pieces of imaged radiation image data, prior to the stopping of the operation, in addition to subject person information and portion information included in each imaging order together with information about the performed imaging operation.

Screen examples that can be displayed by the display unit 270, while the imaging control apparatus 300 performs the standby and accumulation time setting processing (see steps S310 and S315) and the irradiation feasibility display processing (see step S350), are described in detail below with reference to FIGS. 10A, 10B, and 10C.

Figure 10A:
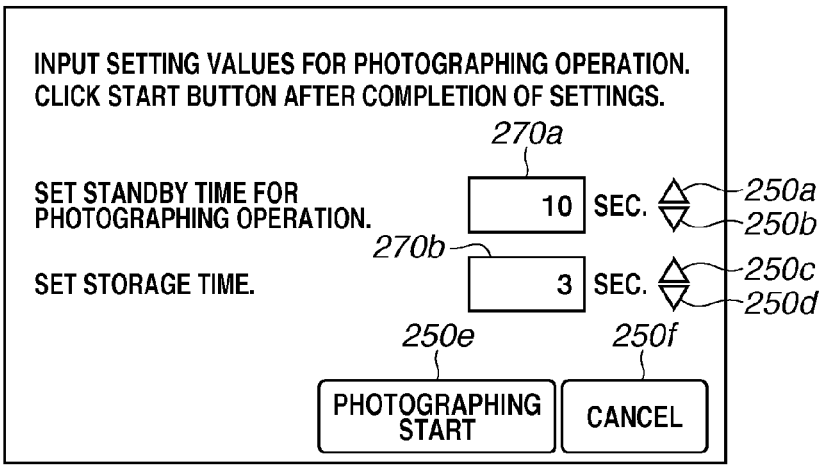
Figure 10B:
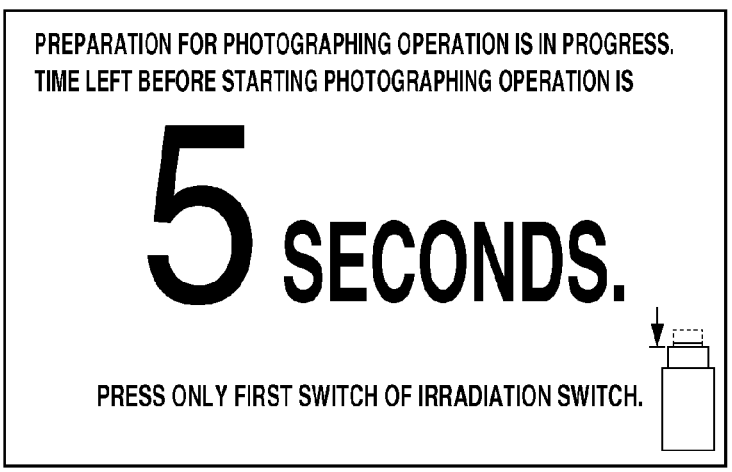

FIG. 10A is an example of the setting screen that can be displayed on the screen of the display unit 270. The screen illustrated in FIG. 10A includes a standby time display field 270a and an accumulation time display field 270b. Further, the screen illustrated in FIG. 10A includes a button 250a and a button 250b. The button 250a is operable to increase the standby time to be displayed in the display field 270a in increments of a predetermined value. The button 250b is operable to decrease the standby time in increments of a predetermined value. The screen illustrated in FIG. 10A further includes a button 250c and a button 250d. The button 250c is operable to increase the accumulation time to be displayed in the display field 270b in increments of a predetermined value. The button 250d is operable to reduce the accumulation time in increments of a predetermined value.

The operator can operate these buttons by pressing the selection buttons of the operation unit 250, similar to a plurality of cursors whose positions are controllable via the operation unit 250. The display control unit 271 controls the display unit 270 to increase or reduce the numerical value displayed in the display field 270a or 270b in response to the manipulation of these buttons.

The screen illustrated in FIG. 10A includes an imaging start button 250e and a cancel button 250f. The imaging start button 250e is operable to start an imaging operation. The cancel button 250f is operable to cancel imaging settings. These buttons 250e and 250f are operable via an operational instruction input via the operation unit 250. More specifically, when the cancel button 250f is pressed, the display control unit 271 terminates the display screen illustrated in FIG. 10A and opens, for example, a new screen indicating information about imaging reservation.

When the operator inputs an operational instruction to select one of a plurality of pieces of imaging reservation information, the display control unit 271 causes the display unit 270 to display the screen illustrated in FIG. 10A again to enable the operator to set standby and accumulation time information that correspond to the selected imaging reservation. As mentioned above, the operator can input the imaging standby time and the accumulation time on the GUI screen via the operation unit 250. A keyboard or another operation unit, such as a speech sound input device, is usable as the operation unit 250.

An example of the countdown display that can be performed by the display unit 270 is described in detail below with reference to FIGS. 10B and 10C. For example, in a case where the display unit 270 is a display device having a large screen sufficient to display a radiation image, the time left before starting the imaging operation can be displayed on the screen of the display device, during the countdown processing, as illustrated in FIG. 10B. The contents of the screen illustrated in FIG. 10B further include a message "imaging preparation is in progress" to inform the current status for the imaging operation to be performed.

Further, for example, additionally performing a countdown operation using speech sounds to be output from a speaker (not illustrated) is useful when the operator moves to a position where the operator cannot view or confirm the screen of the display unit 270. Further, the contents of the screen illustrated in FIG. 10B include an instruction "press only first switch of radiation switch" and a related icon, which can reduce the possibility of causing an ineffective exposure.

Figure 10C:
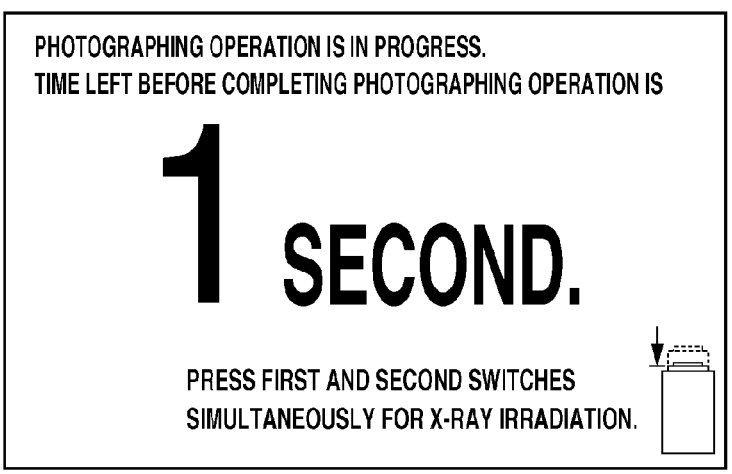

A display screen example illustrated in FIG. 10C includes a message "imaging operation is in progress", which indicates that generation of radioactive rays is permitted in this period. Further, the contents of the screen illustrated in FIG. 10C include an instruction "press first and second switches simultaneously for X-ray irradiation" and a related icon, so that the operator can confirm the time to press the second switch 142.

Further, the contents of the screen illustrated in FIG. 10C include a countdown display indicating the time left before terminating the imaging operation, so that the operator can confirm the remaining irradiation feasible period. For example, in a case where the time left is short as illustrated in FIG. 10C, the operator can determine to interrupt the present irradiation of radioactive rays and press the imaging start button 250e again to restart the storage operation. As a result, it becomes feasible to reduce the possibility of causing an ineffective exposure.

A configuration example of a radiographic imaging system according to another exemplary embodiment is described in detail below with reference to FIG. 11.

Figure 3:
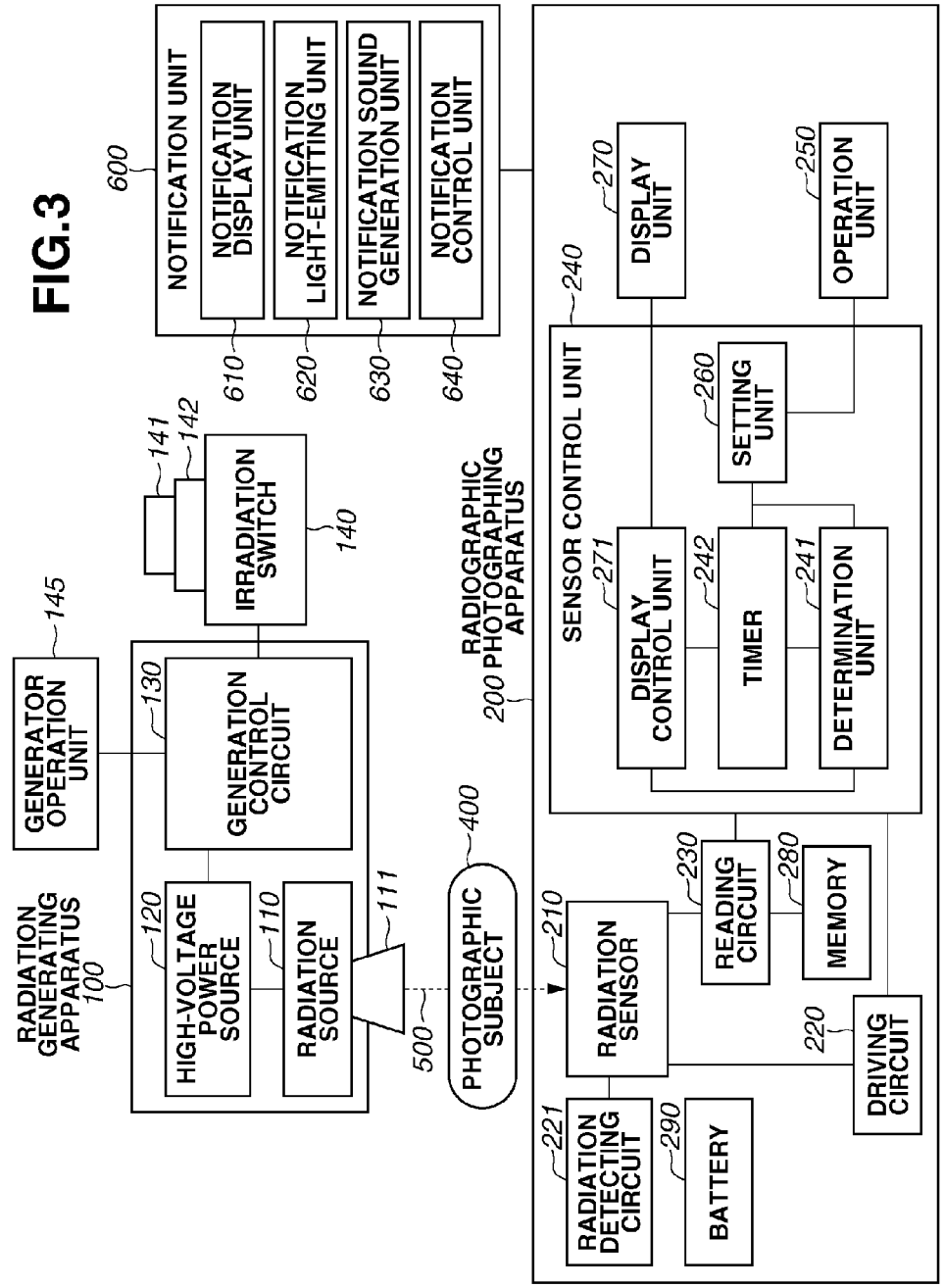
FIG. 3 illustrates a configuration example of radiographic imaging system that includes a portable radiographic imaging apparatus according to an exemplary embodiment.

Similar to the exemplary embodiment illustrated in FIG. 3, the radiographic imaging system illustrated in FIG. 11 includes a sensor control unit 240. The sensor control unit 240 includes a timer 242 and a determination unit 241, which are necessary to perform an operation in the manual synchronization mode. The imaging control apparatus 300 includes a terminal-side determination unit 341, a terminal-side timer 342, a terminal-side operation unit 350, a terminal-side setting unit 360 (time setting unit), a terminal-side display unit 370, and a terminal-side display control unit 371, which are basically similar to the determination unit 241, the timer 242, the operation unit 250, the setting unit 260, the display unit 270, and the display control unit 271 illustrated in FIG. 8. A constituent component, if it is functionally similar to that described in the foregoing embodiment, is denoted by using the same reference numeral. Configuration and processing, if they are not described in the foregoing embodiment, are described in detail below.

The radiographic imaging system illustrated in FIG. 11 includes a notification unit 600 that is connected wirelessly or via a cable to the imaging control apparatus 300. The notification unit 600 is functionally similar to the notification unit 600 illustrated in FIG. 3 and therefore redundant description thereof will be avoided. Thus, even in a case where the operator presses the irradiation switch 140 at a position where the operator cannot view or confirm the screen of the display unit 270 of the imaging control apparatus 300, the operator can appropriately confirm the irradiation timing.

In the radiographic imaging apparatus 200, the sensor control unit 240 does not include the operation unit 250 although it includes the determination unit 241, the timer 242, the setting unit 260, the display unit 270, and the display control unit 271. Therefore, the communication circuit 295 is configured to receive setting information about the standby time and the accumulation time from the imaging control apparatus 300. However, the sensor control unit 240 can include the operation unit 250 to receive operational instructions in various situations.

Further, the radiographic imaging system illustrated in FIG. 11 includes a radiation detecting circuit 221 that is a radiation detection sensor provided as an external unit of the portable radiographic imaging apparatus 200. For example, the radiation detecting circuit 221 is connected to the driving circuit 220 via a cable.

FIG. 12 is a flowchart illustrating an imaging operation that can be performed by the above-mentioned radiographic imaging system.

In the present exemplary embodiment, if the imaging start button of the imaging control unit 300 is pressed (YES in step S320), then in step S330, the terminal-side transmission circuit 395 of the imaging control apparatus 300 transmits a storage start reservation signal to the radiographic imaging apparatus 200. The storage start reservation signal is a signal instructing to perform storage processing for a setting time after the waiting time has elapsed. The terminal-side communication circuit 395 transmits information about the standby time and the accumulation time together with the storage start reservation signal or prior to transmission of the storage start reservation signal. The sensor control unit 240 receives the storage start reservation signal and the standby and accumulation time information via the communication circuit 295. The setting unit 260 stores the standby and accumulation time information in the memory.

If the sensor control unit 240 of the radiographic imaging apparatus 200 confirms the reception of the storage start reservation signal (see step S230), then in step S235, the sensor control unit 240 transmits a reception notification signal to the imaging control apparatus 300. The display control unit 271 starts a countdown display according to the standby time having been set.

If the imaging control apparatus 300 receives the reception notification signal (see step S335), then in step S340, the display control unit 271 starts a countdown display in the imaging control apparatus 300. More specifically, the display control unit 271 causes the display unit 270 to display the time left before starting the imaging operation. In a case where the notification unit 600 is connected to the imaging control apparatus 300, the notification control unit 640 of the notification unit 600 receives a signal notifying the commencement of a standby time clocking operation from the imaging control apparatus 300.

In response to the notification signal, the notification light-emitting unit 620 performs an LED flicker operation. The notification display unit 610 displays a numerical value indicating the time left. The notification sound generation unit 630 performs a notification using speech sounds. The notification to be performed by the notification unit 600 can be appropriately changed according to the time left, based on information output from the terminal-side determination unit 341. Alternatively, the notification control unit 640 can clock the time left and can perform a notification control independent of the imaging control apparatus 300.

In this case, similar to the example illustrated in FIG. 9, if the terminal-side determination unit 341 determines that the period of time from the transmission of the storage start reservation signal (see step S330) to the reception of the reception notification signal (see step S335) has exceeded a predetermined time-out time, more specifically when the reception notification signal cannot be received within a predetermined period of time, the terminal-side display control unit 371 causes the terminal-side display unit 370 to display a message informing abnormality in communications together with a related icon while skipping the countdown operation.

In this case, the cause of the time-out may be a failure in the transmission of the storage start reservation signal or a failure in the reception of the ACK signal. In the case of the failure in the reception of the ACK signal, the radiation sensor 210 may start the storage operation after a predetermined time has elapsed. Therefore, the imaging control apparatus 300 outputs a signal canceling the standby time clocking operation and preventing the transition into the storage state.

If each of the display unit 270 and the terminal-side display unit 370 has started the countdown display operation, then in steps S245 and S345, the sensor control unit 240 and the imaging control apparatus 300 confirm the communication state periodically or randomly. For example, the communication state can be confirmed by transmitting a predetermined command and receiving a reception response. If the reception response cannot be received within a predetermined time-out time, each of the display unit 270 and the terminal-side display unit 370 stops the countdown display operation and displays a message informing the failure in communications.

In the above-mentioned communication state confirmation processing, a transmission source adds time stamp data indicating transmission trial start time to a command to be transmitted to a receiver when they communicate with each other. In this case, it is feasible to measure a communication delay time during the countdown display operation, more specifically, before starting the storage operation. When the above-mentioned processing is performed, it is desired for both apparatuses to perform communication synchronizing processing to adjust their timings before the imaging start button is pressed.

If the display control unit 271 of the radiographic imaging apparatus 200 terminates the countdown display for the standby time having been set, then in step S241, the sensor control unit 240 causes the radiation sensor 210 to start an operation in the storage mode. Substantially simultaneously, in step S245, the sensor control unit 240 causes the communication circuit 295 to transmit a storage start notification signal. If in step S345, the imaging control apparatus 300 receives the storage start notification signal, then in step S350, the terminal-side display unit 370 starts irradiation feasibility display processing. In a case where the notification unit 600 is connected to the imaging control apparatus 300, the notification unit 600 performs similar irradiation feasibility notification processing. The above-mentioned operations are effective in preventing the irradiation feasibility display from being erroneously performed before actually starting the storage processing.

Further, if the storage start notification signal cannot be received within a predetermined time-out time after the termination of the countdown display by the terminal-side display unit 370 or the termination of the notification by the notification unit 600, the imaging control apparatus 300 does not perform the irradiation feasibility display. A setting value of the time-out time substantially limits the period of time from the start of trial transmission of a particular signal to the reception of an ACK signal indicating the reception of the particular signal. If the ACK signal is not received within the time-out time, it is determined that the transmission has failed. The time-out time can be determined based on the range defined by communication protocol standards and user settings.

The irradiation feasibility notification continues during a period of time obtained by subtracting the above-mentioned time-out time from the accumulation time having been set. By performing the above-mentioned operations, it becomes possible to prevent the irradiation feasibility notification from continuing uselessly after the storage processing terminates (see step S260). Further, it becomes feasible to prevent a photographic subject from being unnecessarily exposed to radioactive rays because the radioactive ray irradiation is performed according to the display.

Further, the possibility of being unnecessarily exposed to radioactive rays can be further reduced if the period of time during which the irradiation feasibility notification is performed is set to be equivalent to the time obtained by subtracting the time-out time and the radiation generation time from the accumulation time.

For example, the irradiation time can be acquired by the operator when the operator manipulates the terminal-side operation unit 350 to input information to be set based on either an operational instruction input via the generator operation unit 145 of the radiation generating apparatus 100 or imaging order information acquired from the RIS via a communication circuit of the radiation generating apparatus 100.

The imaging control apparatus 300 transmits the irradiation time to the radiographic imaging apparatus 200 via the terminal-side communication circuit 395. If the imaging order from the RIS includes irradiation conditions, the information received from the RIS can be directly used as irradiation time information. Further, the imaging control apparatus 300 may be able to transmit and receive irradiation conditions to and from the radiation generating apparatus 100 without using any interface dedicated to the synchronized imaging operation. In such a case, the imaging control apparatus 300 uses irradiation conditions obtained from the radiation generating apparatus 100.

The user can synchronize the storage timing with the X-ray irradiation timing by pressing the irradiation switch 140 (see step S120) while the irradiation feasibility display operation is performed.

A imaging control in a imaging operation to be performed in the imaging mode using the radiation detecting circuit 221 is described in detail below with reference to FIG. 13.

First, in steps S100, S200, and S300, an X-ray generation apparatus, an X-ray detection apparatus, and a control unit start their operations. Next, in step S110, the X-ray generation apparatus sets X-ray irradiation conditions (e.g., tube current, tube voltage, and irradiation time). Further, in step S301, the control unit sets various imaging conditions (e.g., entry and confirmation about patient information and entry and confirmation about inspection order). A setting unit or an operation unit provided in the control unit is available to set the imaging conditions.

In the present exemplary embodiment, a general personal computer is usable as the control unit. Further, a keyboard or a mouse associated with the computer can be appropriately used as the setting unit or the operation unit. Alternatively, a dedicated unit including operation buttons can be connected to the computer. Further, a display device associated with the computer is usable as the display unit. When the display device can display GUI buttons, the display device is functionally operable as the setting unit and the operation unit.

Next, in step S305, the control unit selects an imaging mode.

When an imaging mode 1 using the radiation detecting circuit 221 is compared with an imaging mode 2 using the timer 242 (i.e., the manual synchronization mode), the imaging mode 1 is superior to the imaging mode 2 in user-friendliness (e.g., difficulty in imaging timing).

Therefore, in the present exemplary embodiment, the imaging mode is initially fixed to the imaging mode 1 when the operation starts. However, if necessary, the user can change the imaging mode considering irradiation conditions and imaging conditions having been set and physical conditions of a photographic subject (e.g., body shape and portion to be imaged), and other various imaging constraints.

For example, detecting X-rays may be difficult in a case where the dose to be used in the imaging operation is low or the irradiation area is narrow, or in a case where it is required to prevent X-rays from directly entering the radiation sensor 210. In such cases, for example, in response to an operator's instruction input via the operation unit 250 or based on information about imaging conditions, the setting unit 260 automatically selects the imaging mode 2.

Changing the imaging mode is feasible by clicking a GUI button disposed on the screen of the display unit 270. However, the mode change method is not limited to the above-mentioned method. For example, an appropriate method may be selected from a software menu. When each mode tab is selectable, an appropriate method can be selected by switching the tab. Further, it is useful to provide a dedicated mode selection switch on the operation unit of the imaging control apparatus 300 or the radiographic imaging apparatus 200.

However, as described below, the above-mentioned imaging modes are greatly different in operation flow. Therefore, for example, in a case where the selection switch is provided on the radiographic imaging apparatus 200, it is necessary to surely reflect each selected mode to the display content of the operation unit or the display unit. If desired, it may be useful to initially fix the imaging mode to the imaging mode 2 when the operation starts.

If it is determined that the imaging mode is the imaging mode 1, then in step S331, the control unit transmits an irradiation detection start signal to the radiographic imaging apparatus 200. If in step S231 the sensor control unit 240 of the radiographic imaging apparatus 200 receives the irradiation detection start signal, then in step S232, the sensor control unit 240 causes the radiation sensor 210 to immediately start an X-ray irradiation detecting operation. The detecting operation continues until the presence of irradiated X-rays is actually detected or a predetermined time-out time has elapsed.

Further, after starting the irradiation detecting operation, in step S236, the sensor control unit 240 immediately transmits the irradiation detection start signal to the imaging control apparatus 300. If in step S336 the imaging control apparatus 300 receives the irradiation detection start signal, the terminal-side display control unit 371 causes the terminal-side display unit 370 to display a message "the generation of X-rays is feasible." In step S121, the operator confirms the irradiation feasibility display and presses the irradiation switch 140. In step S130, the X-ray generation apparatus generates X-rays.

The irradiation feasibility display operation can be performed by the terminal-side display unit 370 of the imaging control apparatus 300 or can be also performed by the notification unit 600 that is independent of the imaging control apparatus 300. The notification unit 600 is connected to the radiographic imaging apparatus 200 or the imaging control apparatus 300 via a cable or wirelessly. Therefore, the operator can appropriately confirm the feasibility of X-ray irradiation even when the operator is required to press the irradiation switch 140 at a position where the operator cannot view the terminal-side display unit 370 or the display unit 270.

If the X-ray generation apparatus generates X-rays, then in step S237, the radiation detecting circuit 221 performs an X-ray irradiation detection operation. If the radiation detecting circuit 221, or the sensor control unit 240 that has received a signal from the radiation detecting circuit 221, determines that the generation of X-rays has started, the radiographic imaging apparatus 200 immediately starts storing electric charges generated by the entered X-rays.

Then, in step S242, the radiographic imaging apparatus 200 immediately transmits a storage start signal to the imaging control apparatus 300. If the imaging control apparatus 300 receives the storage start signal, the terminal-side display control unit 371 causes the terminal-side display unit 370 to display a message "the generation of X-rays has been detected." The storage operation continues for a predetermined period of time (e.g., one second). The radiographic imaging apparatus 200 can arbitrarily change the accumulation time according to X-ray irradiation conditions. Further, when the radiation detecting circuit 221 or a dedicated sensor detects a termination of the X-ray irradiation, the radiographic imaging apparatus 200 can adjust the accumulation time according to the termination signal.

When the storage processing terminates (see step S260), the radiographic imaging apparatus 200 performs image processing and data transmission processing. The radiographic imaging apparatus 200 transmits the imaged image data to the control unit via the communication circuit 295. In step S370, the control unit performs image processing on the transmitted image data, if necessary, and stores the processed image data. In step S380, the display control unit 271 causes the display unit 270 to display an imaged image.

If it is determined that the imaging operation continues (YES in step S385), the operation returns to step S310 to repeat the setting of imaging conditions. If it is determined that the imaging operation is not continuously performed (YES in step S385), it is controlled to stop the operations of the radiation generating apparatus 100, the radiographic imaging apparatus 200, and the imaging control apparatus 300.

(Acquisition of Correction Data for Calibration)

The radiographic imaging apparatus according to the present exemplary embodiment requires a calibration to correct differences in detection sensitivity between pixels. It is desired to complete the calibration before starting an actual imaging operation. For example, the calibration includes measuring an accurate output value of each pixel under predetermined irradiation conditions and correcting the dispersion in the gain of each pixel and the irradiation irregularity of a used bulb tube. However, to perform the calibration accurately, precise measurement is required to obtain output data from each pixel.

In the present exemplary embodiment, in acquiring the calibration correction data from a white image obtainable when the radiation sensor 210 is uniformly irradiated with radioactive rays, the imaging apparatus performs a white image capturing operation in the imaging mode 2 (i.e., in the manual synchronization mode). The calibration correction data (i.e., sensitivity correction data) obtained from a white image obtained in the imaging mode 2 is used to perform a sensitivity irregularity correction (i.e., a gain correction) for radiographic imaging images obtained in the imaging mode 1 and the imaging mode 2. The sensor control unit 240 of the radiographic imaging apparatus 200 or the image processing circuit of the imaging control apparatus 300 can perform the above-mentioned gain correction.

As mentioned above, in the imaging mode 1 (i.e., in the automatic triggering mode), the radiographic imaging apparatus starts an imaging operation when the presence of X-rays is detected in a state where the radiographic imaging apparatus is irradiated with X-rays. In the present exemplary embodiment, the radiographic imaging apparatus 200 monitors a change in the current flowing through a detector when X-rays reach the radiation sensor 210. If the current change value exceeds a predetermined threshold value, the radiographic imaging apparatus 200 determines that the X-ray irradiation has been started.

The above-mentioned method is desired in that there is not any constraint about irradiation detectable area and in that the detection sensitivity can be enhanced when the generated X-rays are effectively used in the detection. On the other hand, using a part of the generated X-rays for the detection may deteriorate the accuracy of a pixel value at a part of an image if the setting of X-ray irradiation conditions is inappropriate. The area in which the accuracy may deteriorate is variable depending on the X-ray generation timing and the driving timing of the radiographic imaging apparatus. Therefore, if the part of the generated X-rays is used as the calibration correction data, there is a possibility of causing a correction error.

On the other hand, in the imaging mode 2, it is feasible to perform an imaging operation while synchronizing the storage timing with the X-ray irradiation timing. The area in which the pixel value measurement accuracy deteriorates is not basically generated. Therefore, when the above-mentioned detection method is employed, acquiring the calibration correction data in the imaging mode 2 is useful because the correction can be realized appropriately.

As mentioned above, in the manual synchronization mode, the operator can arbitrarily set the standby time (i.e., the period of time from a user instruction to the commencement of storage processing). Therefore, the user can start an imaging operation at desired timing without transmitting and receiving any synchronizing signal to and from the radiation generating apparatus. In addition, the user can easily confirm the time left before starting the storage. It is unnecessary for the operator to carefully check the storage start timing. The possibility that the duration of X-ray irradiation exceeds the storage period can be reduced.

In addition, when the radiographic imaging apparatus is operable in both the manual synchronization mode and the automatic triggering mode, the radiographic imaging apparatus can perform various imaging operations in many imaging conditions without transmitting and receiving any synchronizing signal to and from the radiation generating apparatus. For example, in general imaging conditions, it is desired that the radiographic imaging apparatus selects the automatic triggering mode so that the burden of the operator can be reduced.

On the other hand, when the amount of dose is very small or when the X-ray irradiation time is extremely short, it is desired that the radiographic imaging apparatus selects the manual synchronization mode to surely perform a radiographic imaging operation. When the radiographic imaging apparatus is operable in the above-mentioned synchronization modes 1 and 2, the radiographic imaging apparatus can perform a digital radiographic imaging operation in a wide range of imaging condition even when the radiation generating apparatus does not include any interface circuit capable of inputting and outputting a synchronizing signal.

Further, compared to the automatic triggering mode, the manual synchronization mode is advantageous in that the electric power consumption can be reduced because the detection circuit is not used and no sensor scanning is performed.

When the radiographic imaging apparatus causes the radiation sensor 210 to operate in the above-mentioned manual synchronization mode, the radiographic imaging apparatus supplies electric power to the radiation detecting circuit 221. For example, in a case where the radiographic imaging apparatus performs a radiographic imaging operation with X-rays of an extremely low dose, detecting the start of X-ray irradiation at appropriate timing may be difficult. However, there is no difficulty in detecting the generation of radioactive rays if the timing is not taken into consideration.

Therefore, if the user erroneously presses the irradiation switch 140 before the standby time elapses, or if the irradiation commences wrongly due to a failure even when the radiation sensor 210 is in a imaging preparation state, the radiation detecting circuit 221 detects the irradiation and, for example, the display unit 270 or the notification unit 600 generates a warning based on the detection result. Thus, the operator can easily confirm the failure in the imaging operation at appropriate timing.

In the above-mentioned exemplary embodiments, the radiographic imaging apparatus 200 is configured to capture an X-ray image. However, the present invention is similarly applicable to an imaging operation using α rays, β rays, γ rays, or any other electromagnetic waves.

In the above-mentioned exemplary embodiments, an IP address designating a partner apparatus is transmitted when the communication circuits (e.g., the communication circuit 295 and the terminal-side communication circuit 395) perform data transmission. However, if it is unnecessary to designate a partner apparatus, the broadcasting is usable to transmit IP address information. In this case, for example, it is useful to designate a communication partner apparatus beforehand for each imaging operation and associate the IP address of a transmission source with data to be transmitted and received. The receiver apparatus selectively uses only a signal from the designated apparatus (i.e., a limited part of the received data) in the control.

In the above-mentioned exemplary embodiments, the display that can be realized by the display unit 270 or the terminal-side display 370 and the notification that can be realized by each component of the notification unit 600 may be collectively referred to as "notification."

FIG. 14 illustrates a hardware configuration example of the radiographic imaging apparatus 200 and the imaging control apparatus 300 according to the above-mentioned exemplary embodiment. Constituent components of the configuration illustrated in FIG. 14 have functions similar to those of corresponding components, if they are the same in allocated number. Therefore, redundant description thereof will be avoided.

The sensor control unit 240 includes an FPGA 2401, a RAM 2402, an HDD 2403, an MPU 2404, and a ROM 2405. The FPGA 2401 is configured to control the driving circuit 220 and the reading circuit 230. The MPU 2404 is a circuit that can integrally control operations to be performed by the radiographic imaging apparatus 200. The MPU 2404 executes commands included in a program stored in the ROM 2405 or the HDD 2403 to control each functional component of the radiographic imaging apparatus 200, in such a way as to realize the processing according to the above-mentioned exemplary embodiment.

The RAM 2402 is a work memory operable for the MPU 2404. The HDD 2403 stores an operating system (OS) 2431 and a program 2432 that runs on the OS 2431, in addition to various setting data. The program 2432 is a program that can realize each processing of the flowchart illustrated in FIG. 5, FIG. 9, FIG. 12, or FIG. 13. For example, the functions of the hardware arrangements illustrated in FIGS. 1, 3, 8, and 11 can be realized when the MPU 2404 executes the program 2432.

On the other hand, the imaging control apparatus 300 includes a GPU 3001, a RAM 3002, an HDD 3003, a CPU 3004, and a ROM 3005. The CPU 3004 is a circuit configured to integrally control hardware components of the imaging control apparatus 300 and any other unit connected to the imaging control apparatus 300. To control each component of the imaging control apparatus 300, the CPU 3004 executes commands included in a program stored in the ROM 3005 or the HDD 3003. The RAM 3002 is a work memory operable for the CPU 3004. The HDD 3003 stores an OS 3031 and a program 3032 that runs on the OS 3031, in addition to various setting data. The program 3032 is a program that can realize each processing of the flowchart illustrated in FIG. 9, FIG. 12, or FIG. 13. For example, the functions of the components illustrated in FIG. 3, FIG. 8, and FIG. 11 can be realized when the CPU 3004 executes the program 3032. The GPU 3001 is a circuit dedicated to mainly perform image processing and is configured to process received image data in accordance with an instruction of the CPU 3004.

The MPU 2404 or the CPU 3004, when realizing the functions packaged by the FPGA 2401, prepares a software program corresponding to hardware description languages used in the package of the FPGA 2401 and stores the prepared program, as the program 2432 or 3032, in the HDD 2403 or 3003. The MPU 2404 or the CPU 3004 executes the commands included in the stored program sequentially or in parallel, in such a way as to realize the above-mentioned processing described in the flowchart illustrated in FIG. 5, FIG. 9, or FIG. 12. On the other hand, in a case where a hardware arrangement is employed to realize functions comparable to the programmed functions of the MPU or the CPU, it is useful to generate a program described by using hardware description languages that correspond to the above-mentioned program and obtain configuration data of the FPGA.

A radiographic imaging apparatus according to another exemplary embodiment is described in detail below.

Figure 15:
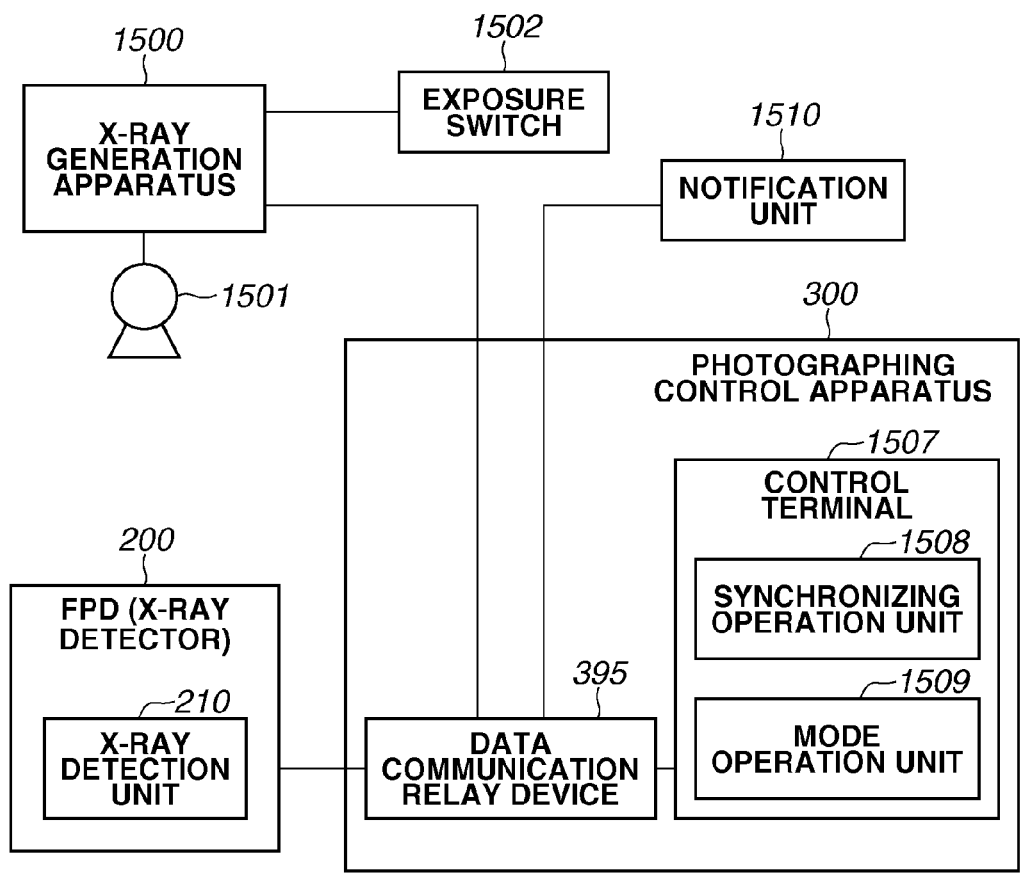
FIG. 15 is a block diagram illustrating a configuration example of an X-ray imaging apparatus.

FIG. 15 illustrates a configuration example of an X-ray imaging apparatus, as an example of the radiographic imaging apparatus that can capture a radiation image with radioactive rays. As illustrated in FIG. 15, the X-ray imaging apparatus includes an X-ray generation apparatus 1500 serving as a radiation source, an exposure switch 1502, an X-ray detector 200 serving as a radiation detector, a imaging control apparatus 300, and a notification unit 1510. The notification unit 1510 serves as a display unit configured to perform a notification (i.e., a display) using light, image, and sound in such a way as to display an operational state of the radiation detector.

The X-ray generation apparatus 1500 includes an X-ray bulb tube 1501 that is operable as an X-ray source and controls an X-ray exposure according to an operation of the exposure switch 1502. The X-ray generation apparatus 1500 and the X-ray detector 200 can communicate with each other to notify their operational states for synchronization in a imaging operation. In the present exemplary embodiment, the X-ray generation apparatus 1500 communicates with the X-ray detector 200 via a data communication relay device (i.e., a terminal-side communication circuit) 395 of the imaging control apparatus 300. Alternatively, the X-ray generation apparatus 1500 and the X-ray detector 200 can be configured to directly communicate with each other.

Further, a communication path between the X-ray generation apparatus 1500 and the exposure switch 1502 and a communication path between the X-ray generation apparatus 1500 and the X-ray detector 200 can be configured as a wired or wireless path. If a wireless communication is employed, the operability can be improved because no communication cable is required. The X-ray generation apparatus 1500 is configured to selectively perform an exposure operation in response to only an operational signal of the exposure switch 1502 or in response to a state signal of the X-ray detector 200 in addition to the operational signal of the exposure switch 1502. As described in detail below, the X-ray generation apparatus 1500 is operable according to a plurality of imaging modes.

The X-ray detector 200 includes a photoelectric conversion element (not illustrated) and acquires an X-ray image when it is exposed to X-rays. The photoelectric conversion element stores electric charges according to the light of a scintillator that emits light when it is exposed to X-rays. However, the photoelectric conversion element can be configured to store electric charges according to the amount of X-rays (namely, directly detect X-rays without using the scintillator).

Further, the X-ray detector 200 can communicate with the X-ray generation apparatus 1500, the notification unit 1510, and a control terminal 1507 via the data communication relay device 395 of the imaging control apparatus 300. Alternatively, the X-ray detector 200 can be configured to directly communicate with the X-ray generation apparatus 1500, the notification unit 1510, and the control terminal 1507, without using the data communication relay device 395. Further, a communication path between two of the X-ray detector 200, the X-ray generation apparatus 1500, the notification unit 1510, and the control terminal 1507 can be configured as a wired or wireless path. If a wireless communication is employed, the operability can be improved because no communication cable is required.

In the above-mentioned configuration, the X-ray detector 200 can receive an X-ray generation preparation completion signal from the X-ray generation apparatus 1500. Further, the X-ray detector 200 can transmit an X-ray acceptable signal to the X-ray generation apparatus 1500. The X-ray detector 200 includes an X-ray detection unit 210, which is usable to determine whether the X-ray detector 200 is irradiated with X-rays.

The exposure switch 1502 is a switch that enables a user to cause the X-ray generation apparatus 1500 to perform an exposure-related operation. The exposure switch 1502 includes a first switch that is operable to cause the X-ray bulb tube 1501 to prepare for the generation of X-rays and a second switch that is operable to permit the exposure. If desired, the exposure switch 1502 can be configured to function as a forcible synchronizing switch so that the control terminal 1507 can be simplified in the number of required functions.

The notification unit 1510 has light and sound generation capability to realize a notification function and a volume adjustment function. In the present exemplary embodiment, the notification form is not limited to light and sound. Another notification forms (e.g., vibration, temperature change, and shape change) and a combination thereof are employable. The volume adjustment function is a function of adjusting the quantity of light (i.e., luminance) and the volume of sounds to be output from the notification unit 1510. The control terminal 1507 of the imaging control apparatus 300 can be configured to control the volume adjustment function.

In the present exemplary embodiment, the notification unit 1510 does not include any notification pattern and performs a notification operation according to an input command signal. However, the notification unit 1510 is not limited to the above-mentioned example and can be configured to store a plurality of notification patterns to perform various patterns of notifications according to commands from the imaging control apparatus 300.

The notification unit 1510 receives signals from the X-ray detector 200 and the control terminal 1507 of the imaging control apparatus 300 via the data communication relay device 395. The notification unit 1510 performs a notification operation according to a received signal. More specifically, the notification unit 1510 generates a startup sound at a volume having been set beforehand when the imaging apparatus starts its operation. Thus, the user can confirm the sound volume having been set. It is feasible to set an appropriate volume according to an operational state of the imaging apparatus.

In addition, the notification unit 1510 transmits and receives communication state confirmation data to and from the control terminal 1507 at predetermined time intervals. In this case, if the notification unit 1510 cannot receive any signal from the control terminal 1507 for a predetermined time, the operational state of the notification unit 1510 is automatically switched into a state in which infeasibility of the exposure is notified. Thus, it is feasible to prevent an error notification from being generated. Thus, in a state where the exposure is infeasible, the notification unit 1510 does not continue to notify that the exposure is feasible.

The imaging control apparatus 300 includes the control terminal 1507 and the data communication relay device 395. The data communication relay device 395 serves as a relay unit when the imaging control apparatus 300 communicates with each of the X-ray generation apparatus 1500, the X-ray detector 200, the notification unit 1510, and the control terminal 1507. As mentioned above, each communication path can be configured as a wired or wireless path. The control terminal 1507 includes a mode operation unit 1509 configured to switch a imaging mode of the X-ray detector 200 and a synchronizing operation unit 1508 configured to forcibly synchronize the X-ray generation apparatus 1500 with the X-ray detector 200.

In the present exemplary embodiment, the X-ray detector 200 can perform the following driving control when the X-ray detector 200 executes a program stored therein. However, the X-ray detector 200 can be configured to operate simply according to an instruction from the control terminal 1507. For example, as described in detail below, in the present exemplary embodiment, the X-ray detector 200 performs execution determination about state transition. However, the imaging control apparatus 300 can be configured to indicate a driving state into which the X-ray detector 200 transits according to the imaging mode.

Similarly, each of the notification unit 1510 and the X-ray generation apparatus 1500 can be configured to operate simply according to an instruction from the control terminal 1507. As mentioned above, an integrated control system can be realized if each of the apparatuses is configured to perform its operation according to an instruction from the control terminal 1507. This is useful to enhance maintainability, and realize weight reduction, downsizing, and cost reduction for the devices other than the imaging control apparatus 300. Further, it is feasible to enhance portability and usability if all communications are wirelessly realized in the present exemplary embodiment.

The X-ray detector 200 is operable in a plurality of driving states under control of the imaging control apparatus 300. More specifically, in a imaging preparation state, the X-ray detector 200 performs initialization processing including a photoelectric conversion element refreshing operation. In a imaging permissible state, the X-ray detector 200 waits for a imaging start instruction without performing the initialization processing. In a imaging in progress state, the X-ray detector 200 captures an image.

Figure 17:
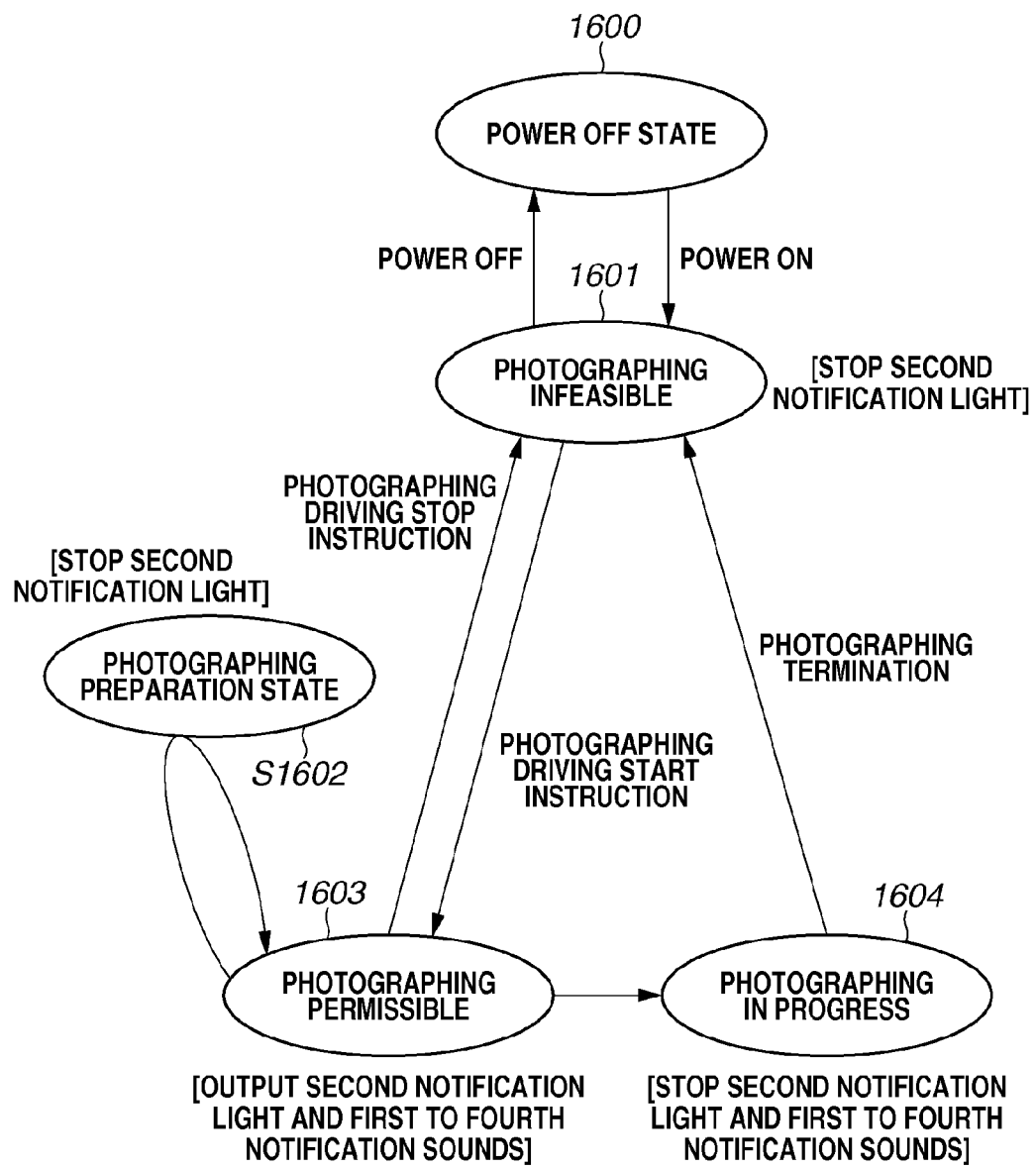
FIG. 17 is a state transition diagram illustrating an example transition of the driving state of the X-ray detector in a second imaging mode.
Figure 18:
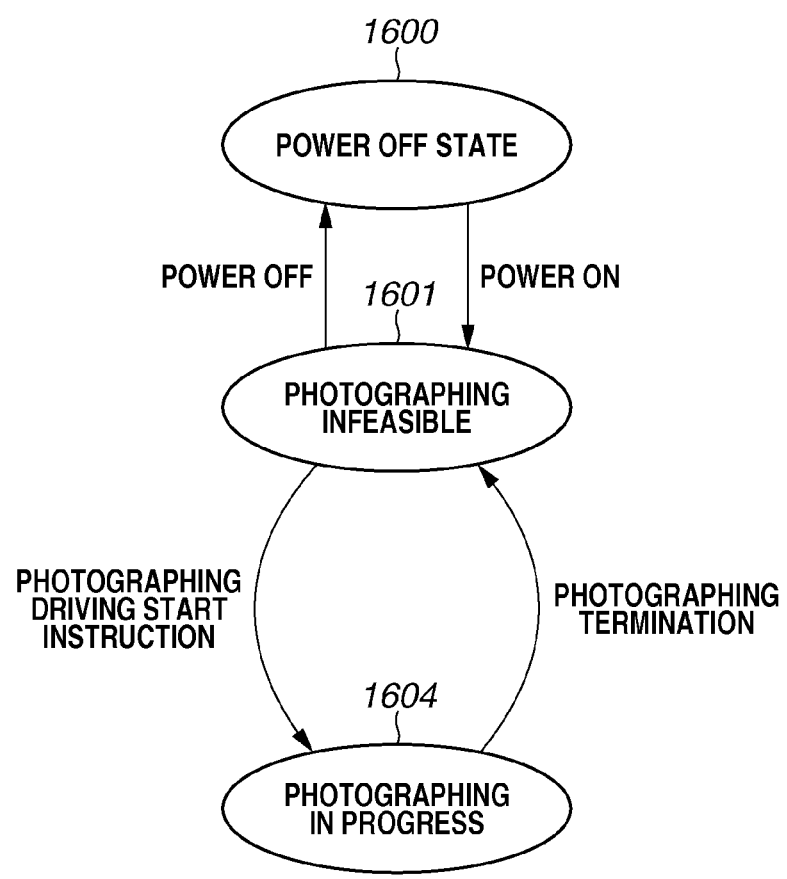
FIG. 18 is a state transition diagram illustrating an example transition of the driving state of the X-ray detector in a third imaging mode.

The driving state of the X-ray detector 200 is described in detail below with reference to FIGS. 16 to 18. Further, the X-ray imaging apparatus according to the present exemplary embodiment is operable in a plurality of imaging modes differentiated in the transition of the driving state of the X-ray detector 200. Respective imaging modes are mutually different in the combination of the driving state and the period in which a user exposure operation can be permitted. The X-ray imaging apparatus according to the present exemplary embodiment is operable in the following three imaging modes. However, the total number of imaging modes differentiated from each other is not limited to the examples but equal to or greater than 2 as described below. Further, the type of each imaging mode can be modified.

In a first imaging mode (i.e., a synchronized imaging mode), the X-ray detector 200 and the X-ray generation apparatus 1500 are synchronized with each other in response to a trigger signal input from the exposure switch 1502 to perform their imaging preparations and set exposure preparation timing in the transition of the driving state.

For example, if the exposure button is pressed in a imaging standby state, the X-ray detector 200 is brought into an X-ray receivable state. The X-ray detector 200 transmits a radiation acceptable signal to the X-ray generation apparatus 1500. The X-ray generation apparatus 1500 performs an X-ray imaging operation to generate X-rays. As mentioned above, in the first imaging mode, if the X-ray detector 200 is operating in the imaging preparation state (i.e., the imaging standby state), the X-ray detector 200 can prepare for a imaging operation to be started when the exposure switch 1502 is pressed.

Accordingly, in the first imaging mode, the notification unit 1510 starts a notification operation when the driving state transits into the imaging preparation state. To notify the feasibility of the imaging operation, the notification operation by the notification unit 1510 continues until the imaging operation actually starts or a signal to stop or cancel the imaging operation is input. As a notification method, lighting/quenching or any other notification is usable if it can clearly express whether the imaging operation is feasible (i.e., whether the driving state of the X-ray detector 200 is in a permission period in which the exposure is permissible).

The above-mentioned first imaging mode is advantageous in that a high-quality image can be acquired stably. Further, the risk of causing an error exposure can be reduced when the X-ray generation apparatus 1500 does not generate any X-rays if no signal is obtained from the X-ray detector 200. The imaging apparatus can perform imaging processing excellent in safety. However, the X-ray generation apparatus 1500 and the X-ray detector 200 are required to communicate with each other for the synchronization.

In a second imaging mode (i.e., a non-synchronized imaging mode), the X-ray detector 200 and the X-ray generation apparatus 1500 are synchronized with each other for a imaging operation when the X-ray detector 200 detects X-rays generated from the X-ray bulb tube 1501. Accordingly, in the second imaging mode, the X-ray generation apparatus 1500 and the X-ray detector 200 are not required to communicate with each other for the synchronization. In other words, no synchronizing signal is required in performing a imaging operation.

In the second imaging mode, the X-ray detector 200 constantly operates in the imaging permissible state (in which initialization processing is prohibited and null reading is continuously performed). The imaging apparatus performs a imaging operation when the X-ray detection unit 210 detects generation of X-rays. Accordingly, X-ray detector 200 is commonly usable for a plurality of different X-ray generation apparatuses. Further, the imaging apparatus does not use any electric signal to perform synchronizing processing. Therefore, using an X-ray generation apparatus dedicated to a film cassette is feasible.

The second imaging mode is characterized in that the imaging apparatus can start a imaging operation substantially anytime because the X-ray detector 200 almost operates in the imaging permissible state, except when the X-ray detector 200 transits into the imaging preparation state to perform a refreshing operation.

However, the way of outputting X-rays is variable depending on the type the X-ray bulb tube 1501. If the way of outputting X-rays is inappropriate, it may be difficult to perform a imaging operation in the second imaging mode that does not require synchronization processing.

In the second imaging mode, the notification unit 1510 notifies exposure permission period, which is a period of time from the transition into the imaging permissible state from a imaging infeasible state, or the imaging preparation state, to the transition into the imaging preparation state or the imaging in progress state. Such an explicit notification enables a user to know the timing at which the user can perform an exposure operation. Further, in the present exemplary embodiment, the period of time during which the radiation sensor 210 operates at the imaging permissible state (i.e., a imaging feasible time) is limited within a predetermined period of time. The notification unit 1510 can perform a notification that enables the user to check the elapsing or remaining imaging feasible time. For example, using a sound or voice generation pattern that varies according to the remaining time is useful to let the user know the elapsed time. Thus, the work efficiency of the user or the risk of causing an error exposure can be further reduced.

In a third imaging mode (i.e., a manually synchronized imaging mode), the X-ray generation apparatus 1500 and a imaging operation of the X-ray detector 200 are synchronized in the following manner. The user manually changes the driving state of the X-ray detector 200 to the imaging in progress state and instructs the X-ray generation apparatus 1500 to cause the X-ray bulb tube 1501 to generate X-rays. Thus, the X-ray detector 200 performs a imaging operation for a period of time having been set according to an external instruction.

The third imaging mode is advantageous in that the X-ray generation apparatus 1500 and the X-ray detector 200 are not required to perform communications for the synchronization in a imaging operation. Thus, the third imaging mode is applicable to an X-ray bulb tube that cannot perform a imaging operation in the second imaging mode. In the third imaging mode, the user forcibly changes the driving state of the X-ray detector 200 to the imaging in progress state (i.e., an X-ray reception state). In this case, the period of time during which the X-ray detector 200 can continuously operate in the imaging in progress state is limited. Therefore, it is necessary to cause the X-ray bulb tube 1501 to generate X-rays in the imaging in progress state.

Accordingly, in the third imaging mode, the notification unit 1510 clearly presents the period of time from the transition into the imaging in progress state, to the termination of the imaging in progress state. Such a notification can prevent the user from performing an erroneous exposure operation. The user can surely perform a imaging operation because the exposure start timing and the exposure feasible period become apparent.

Hereinafter, example transitions of the driving state when the X-ray detector 200 is operable in various imaging modes and notification operations that can be realized by the notification unit 1510 are described in detail below with reference to FIGS. 16 to 19. FIG. 16 illustrates example transitions of the driving state when the X-ray detector 200 is operating in the first imaging mode. FIG. 17 illustrates example transitions of the driving state when the X-ray detector 200 is operating in the second imaging mode. FIG. 18 illustrates example transitions of the driving state when the X-ray detector 200 is operating in the third imaging mode. FIG. 19 illustrates various types of notification operations that can be realized by the notification unit 1510.

Sequential transitions of the driving state when the X-ray detector 200 is operating in the first imaging mode are described in detail below with reference to FIG. 16.

In power OFF state S1600, the power source is in a deactivated state. If the power source starts supplying electric power to the X-ray detector 200, the driving state of the X-ray detector 200 transits into a imaging infeasible state S1601. In the imaging infeasible state S1601, the X-ray detector 200 is not ready to receive X-rays (because of the necessity of dark current refreshment) although the power source is already activated. Therefore, capturing an X-ray image is infeasible in the imaging infeasible state S1601.

Subsequently, the driving state of the X-ray detector 200 transits into a imaging preparation state S1602, in which the X-ray detector 200 can perform a imaging operation. In the imaging preparation state S1602, a dark current removing operation is performed and, by repeating this state, the X-ray detector 200 is constantly maintained in a imaging feasible state.

A imaging permission state 1603 is variable depending on the imaging mode, as described in detail below.

A imaging in progress state 1604 is a state where the X-ray detector 200 can store electric charges when it is irradiated with X-rays after stopping discharging the remaining electric charges and can acquire an X-ray image.

The switching between two imaging modes is feasible when the X-ray detector 200 is operating in the imaging infeasible state S1601.

In the present exemplary embodiment, the notification unit 1510 is controlled in such a way as to notify the user of the good time to press the exposure switch 1502 to cause the X-ray generation apparatus 1500 to start exposure processing, instead of notifying the imaging mode or the operational state of the sensor.

Figure 16:
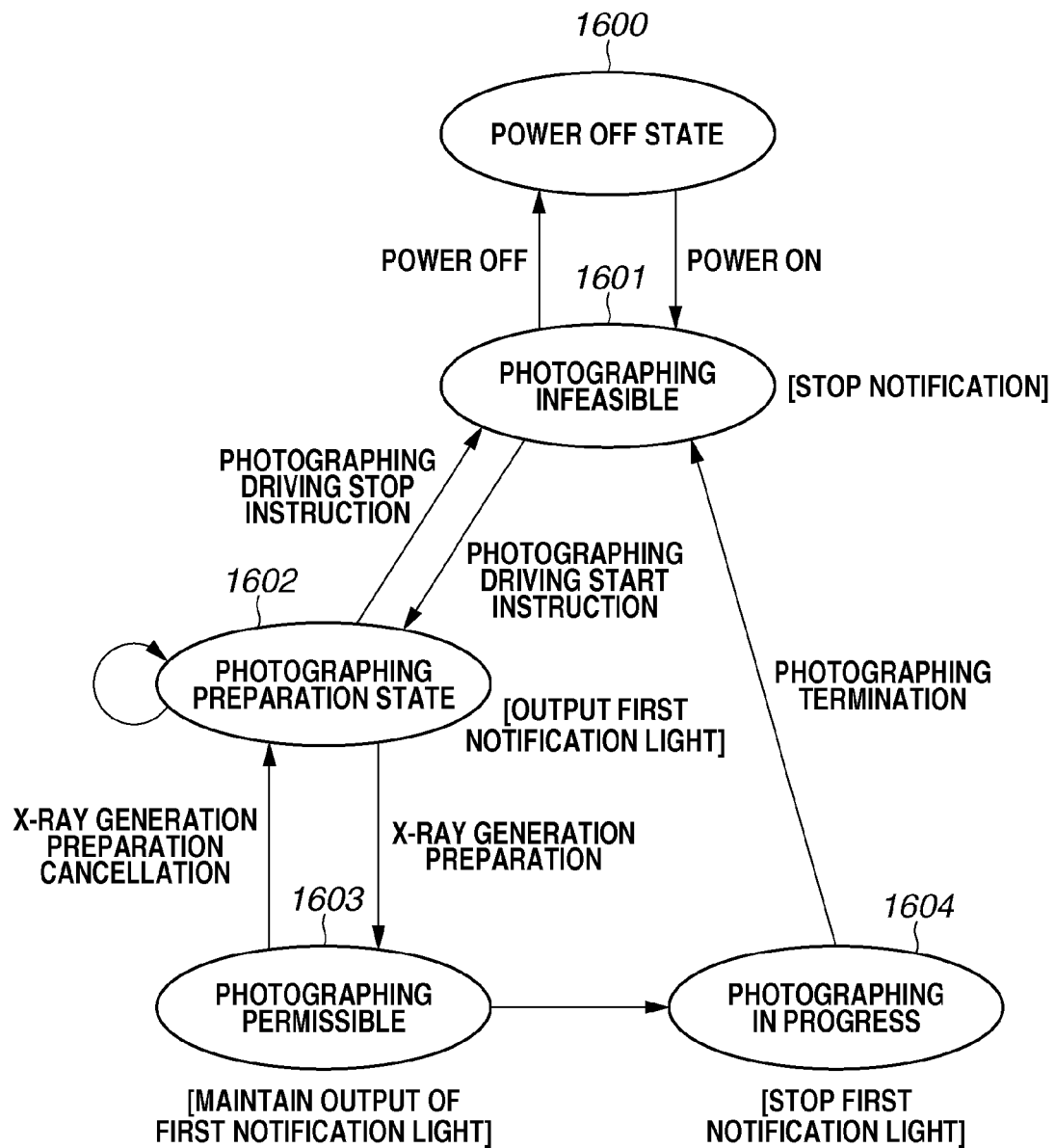
FIG. 16 is a state transition diagram illustrating an example transition of the driving state of an X-ray detector in a first imaging mode.

Operation in First Imaging Mode (See FIG. 16)

As mentioned above, the synchronized imaging operation is performed in the first imaging mode. More specifically, the X-ray generation apparatus 1500 and the X-ray detector 200 synchronize with each other in a imaging operation so that the preparation for the X-ray detector 200 can be synchronized with the exposure timing of the X-ray generation apparatus 1500.

In the power OFF state S1600, the power source is in the deactivated state. If the power source starts supplying electric power to the X-ray detector 200, the driving state of the X-ray detector 200 transits into the imaging infeasible state S1601. In the imaging infeasible state S1601, the X-ray detector 200 is not ready to receive X-rays (because of the necessity of dark current refreshment) although the power source is already activated. Therefore, capturing an X-ray image is infeasible in the imaging infeasible state S1601.

In the imaging infeasible state S1601, the X-ray detector 200 does not start its operation unless a imaging driving start instruction is received from the control terminal 1507. Further, in this state, the X-ray generation apparatus 1500 does not perform an X-ray exposure operation even when a signal is received from the exposure switch 1502. Further, the control terminal 1507 brings the notification unit 1510 into a quenching state (see FIG. 19) to indicate that the imaging operation is infeasible, when the driving state transits into the imaging infeasible state S1601 from the power OFF state S1600, the imaging preparation state S1602, or the imaging in progress state S1604.

The user can recognize that the imaging operation is presently infeasible while checking the quenching state of the notification unit 1510. Further, the user can confirm that the imaging operation is presently infeasible at the control terminal 1507. Further, while the X-ray detector 200 is operating in the imaging infeasible state S1601, the mode operation unit 1509 of the control terminal 1507 can switch the imaging mode between the first, second, and third imaging modes.

If the X-ray detector 200 receives a imaging driving start instruction from the control terminal 1507 in the imaging infeasible state S1601, the driving state of the X-ray detector 200 transits into the imaging preparation state S1602. On the other hand, if the power source stops supplying electric power (if the power source is turned off) in the imaging infeasible state S1601, the driving state of the X-ray detector 200 transits into the power OFF state S1600.

In the imaging preparation state S1602, the X-ray detector 200 periodically performs a refreshing operation to remove electric charges naturally stored. When the driving state transits into the imaging preparation state S1602 from the imaging infeasible state S1601, the notification unit 1510 outputs a first notification light indicating that the present imaging mode is the first imaging mode and the exposure operation is feasible (see FIG. 19). The first notification light enables the user to confirm that the present imaging mode is the first imaging mode and the imaging operation is presently feasible. Further, the user can confirm that the imaging operation is presently feasible at the control terminal 1507.

When the X-ray generation apparatus 1500 receives an input signal from the first switch of the exposure switch 1502, the X-ray generation apparatus 1500 transmits an X-ray generation preparation signal to the X-ray detector 200 and starts an exposure preparation operation for the X-ray bulb tube 1501. Subsequently, if the X-ray generation apparatus 1500 receives an input signal from the second switch of the exposure switch 1502, the X-ray generation apparatus 1500 transmits an X-ray exposure signal to the X-ray detector 200 and generates X-rays according to an exposure permission signal from the X-ray detector 200. However, if no input signal can be received from the first switch of the exposure switch 1502, the X-ray generation apparatus 1500 transmits an X-ray generation preparation cancel signal to the X-ray detector 200.

If the X-ray detector 200 receives a imaging driving stop instruction from the control terminal 1507 in the imaging preparation state S1602, the driving state of the X-ray detector 200 transits into the imaging infeasible state S1601. Further, if the X-ray detector 200 receives an X-ray generation preparation signal from the X-ray generation apparatus 1500 in the imaging preparation state S1602, the driving state of the X-ray detector 200 transits into the imaging permissible state S1603.

If the X-ray detector 200 receives an X-ray exposure signal in the imaging permissible state S1603, the X-ray detector 200 maintains a state where an image capturing operation can be started. In this state, the X-ray detector 200 continuously performs a null reading operation to remove electric charges remaining in the sensor. Further, while the X-ray detector 200 is operating in the imaging permissible state S1603, the control terminal 1507 causes the notification unit 1510 to maintain the first notification light to indicate that the imaging operation is feasible (see FIG. 19). Further, as mentioned above, the user can confirm that the imaging operation is presently feasible at the control terminal 1507.

If the X-ray detector 200 receives the X-ray generation preparation cancel signal from the X-ray generation apparatus 1500 in the imaging permissible state S1603, the driving state of the X-ray detector 200 transits into the imaging preparation state S1602. Further, if the X-ray detector 200 receives the X-ray exposure signal from the X-ray generation apparatus 1500 in the imaging permissible state S1603, the driving state of the X-ray detector 200 transits into the imaging in progress state S1604.

In the imaging in progress state S1604, the X-ray detector 200 performs an X-ray image acquiring operation. In this case, the X-ray detector 200 outputs an exposure permission signal to the X-ray generation apparatus 1500. The X-ray generation apparatus 1500 generates X-rays according to the exposure permission signal. The notification unit 1510 is brought into a quenching state to indicate that the imaging operation is infeasible when the driving state transits from the imaging permissible state S1603 into the imaging in progress state S1604. The control terminal 1507 performs a display indicating that the imaging operation is in progress. If the imaging operation terminates, the control terminal 1507 displays a captured image. If the imaging operation terminates, the driving state of the X-ray detector 200 returns from the imaging in progress state S1604 to the imaging infeasible state S1601. The control terminal 1507 brings the notification unit 1510 into the quenching state.

Operation in Second Imaging Mode

In the second imaging mode, the X-ray generation apparatus 1500 and the X-ray detector 200 are not synchronized. The X-ray detector 200 starts a imaging operation in response to a trigger signal input from the X-ray detection unit 210 when the X-ray detector 200 is irradiated with X-rays. Hereinafter, sequential transitions of the driving state when the X-ray detector 200 is operating in the second imaging mode are described in detail below with reference to FIG. 17.

Transition conditions for the power OFF state S1600 and the imaging infeasible state S1601 are similar to those in the first imaging mode (see FIG. 16). If the X-ray detector 200 receives a imaging driving start instruction from the control terminal 1507 in the imaging infeasible state S1601, the driving state of the X-ray detector 200 transits into the imaging permissible state S1603.

When the X-ray generation apparatus 1500 receives an input signal from the first switch of the exposure switch 1502 in the second imaging mode, the X-ray generation apparatus 1500 start an exposure preparation operation for the X-ray bulb tube 1501. If the X-ray generation apparatus 1500 completes the exposure preparation for the X-ray bulb tube 1501, the X-ray generation apparatus 1500 is brought into a state where an input signal can be received from the second switch of the exposure switch 1502. If the X-ray generation apparatus 1500 receives an input signal from the second switch, the X-ray generation apparatus 1500 causes the X-ray bulb tube 1501 to generate X-rays. If no input signal can be received from the first switch of the exposure switch 1502 before an input signal is received from the second switch of the exposure switch 1502, the X-ray generation apparatus 1500 cancels the exposure preparation for the X-ray bulb tube 1501.

When the driving state transits into the imaging infeasible state S1601 from each the power OFF state S1600, the imaging permissible state S1603, and the imaging in progress state S1604, the control terminal 1507 causes the notification unit 1510 to quench a second notification light as described below (see FIG. 19) to indicate that the imaging operation is infeasible. The user can recognize that the imaging operation is presently infeasible based on the quenching state of the notification light at the notification unit 1510. Further, the user can confirm that the imaging operation is presently infeasible at the control terminal 1507. As mentioned above, in the imaging infeasible state S1601, the mode operation unit 1509 of the control terminal 1507 can switch the mode between the first, second, and third imaging modes.

If the X-ray detector 200 receives a imaging driving start instruction from the control terminal 1507 in the imaging infeasible state S1601, the X-ray detector 200 transits into the imaging permissible state S1603 after completing a refreshing operation for the photoelectric conversion element. On the other hand, if the power source stops supplying electric power to the X-ray detector 200, the driving state of the X-ray detector 200 transits from the imaging infeasible state S1601 to the power OFF state S1600.

In the imaging permissible state S1603, the X-ray detector 200 maintains a state where an image capturing operation can be started in response to a signal input from the X-ray detection unit 210 when the X-ray detector 200 is irradiated with X-rays. In this state, the X-ray detector 200 continuously performs a null reading operation and does not perform the refreshing operation. Further, the control terminal 1507 causes the notification unit 1510 to start outputting the second notification light (i.e., imaging feasible notification, see FIG. 19) when the driving state transits into the imaging permissible state S1603 from the imaging infeasible state S1601 or the imaging preparation state S1602.

Maintaining the imaging permissible state S1603 is limited within a predetermined time. Therefore, the notification unit 1510 generates a warning using first to fourth notification sounds to raise the attention of the user with respect to the time elapse or the time left. The user can confirm that the imaging operation is presently feasible at the control terminal 1507. Further, the user can confirm the remaining time with respect to the imaging permissible state at the control terminal 1507.

If the X-ray detector 200 receives a imaging driving stop instruction from the control terminal 1507 in the imaging permissible state S1603, the driving state of the X-ray detector 200 transits into the imaging infeasible state S1601. Further, if the X-ray detection unit 210 detects X-rays in the imaging permissible state S1603, the driving state of the X-ray detector 200 transits into the imaging in progress state S1604. Further, if a predetermined time elapses in the imaging permissible state S1603 while no X-rays can be detected by the X-ray detection unit 210, a significant amount of electric charges (that causes dark current) will be stored. Therefore, to remove the stored electric charges, the driving state of the X-ray detector 200 periodically transits into the imaging preparation state S1602.

In the imaging preparation state S1602, the X-ray detector 200 performs a refreshing operation one time to remove the stored electric charges and the driving state of the X-ray detector 200 returns to the imaging permissible state S1603. If the driving state transits into the imaging preparation state S1602 from the imaging permissible state S1603, the control terminal 1507 brings the notification unit 1510 into the quenching state to inform the user that the imaging operation is infeasible (see FIG. 19). As mentioned above, the user can confirm the imaging operation is presently infeasible at the control terminal 1507.

If the X-ray detection unit 210 detects X-rays after the X-ray generation apparatus 1500 starts generating X-rays, the driving state of the X-ray detector 200 transits into the imaging in progress state S1604 from the imaging permissible state S1603 and the X-ray detector 200 performs an X-ray image acquiring operation. When the driving state transits from the imaging permissible state S1603 to the imaging in progress state S1604, the control terminal 1507 brings the notification unit 1510 into the quenching state indicating that the imaging operation is in progress.

The control terminal 1507 displays a notification indicating that the imaging operation is in progress and, if the imaging operation terminates, displays a captured image on a display device (not illustrated) thereof. Further, when the X-ray detector 200 terminates the imaging operation, the driving state of the X-ray detector 200 transits into the imaging infeasible state S1601 from the imaging in progress state S1604.

Operation in Third Imaging Mode

As mentioned above, in the third imaging mode, the X-ray generation apparatus 1500 and the X-ray detector 200 are forcibly synchronized based on a manual operation to perform a imaging operation. More specifically, the user performs manual operations to instruct the X-ray detector 200 to start a imaging operation and to instruct the X-ray generation apparatus 1500 to start generating X-rays. Sequential transitions of the driving state when the X-ray detector 200 is operating in the third imaging mode are described in detail below with reference to FIG. 18.

The operations in the imaging infeasible state S1601 are similar to those in the first and second imaging modes. If the X-ray detector 200 receives a imaging driving start instruction from the control terminal 1507 in the imaging infeasible state S1601, the driving state of the X-ray detector 200 transits into the imaging in progress state S1604 after completing the refreshing operation. On the other hand, if the power source stops supplying electric power to the X-ray detector 200, the driving state of the X-ray detector 200 transits into the power OFF state S1600 from the imaging infeasible state S1601.

If the driving state of the X-ray detector 200 transits into the imaging infeasible state S1601 from the power OFF state S1600 or the imaging in progress state S1604, the control terminal 1507 brings the notification unit 1510 into the quenching state to indicate that the imaging operation is infeasible. Thus, the user can recognize that the imaging operation is presently infeasible. Further, the user can confirm that the imaging operation is presently infeasible at the control terminal 1507. Further, in the imaging infeasible state S1601, the mode operation unit 1509 of the control terminal 1507 can switch the mode between the first, second, and third imaging modes.

If the X-ray generation apparatus 1500 receives an input signal from the first switch of the exposure switch 1502, the X-ray generation apparatus 1500 starts an exposure preparation operation for the X-ray bulb tube 1501. When the X-ray generation apparatus 1500 completes the exposure preparation operation for the X-ray bulb tube 1501, the X-ray generation apparatus 1500 starts receiving an input signal to be output from the second switch of the exposure switch 1502. If the X-ray generation apparatus 1500 receives an input signal from the second switch, the X-ray generation apparatus 1500 causes the X-ray bulb tube 1501 to generate X-rays. If no input signal can be received from the first switch before an input signal is received from the second switch, the X-ray generation apparatus 1500 cancels the exposure preparation for the X-ray bulb tube 1501.

While the X-ray detector 200 is operating in the imaging in progress state S1604, the X-ray generation apparatus 1500 generates X-rays in response to a user operation as mentioned above and the X-ray detector 200 acquires an X-ray image. More specifically, an X-ray imaging operation can be performed. The control terminal 1507 displays the captured image based on the imaging in progress display.

If the driving state transits into the imaging in progress state S1604 from the imaging infeasible state S1601, the control terminal 1507 causes the notification unit 1510 to output a third notification light indicating that the imaging operation is feasible. Further, in the third imaging mode, the control terminal 1507 causes the notification unit 1510 to output a fifth notification sound for a period of time during which the X-ray reception is feasible in the imaging in progress state S1604.

If the imaging operation terminates, more specifically, if the X-ray receivable duration passes, the driving state of the X-ray detector 200 transits into the imaging infeasible state S1601 from the imaging in progress state S1604. Further, the control terminal 1507 causes the notification unit 1510 to stop outputting the third notification light and the fifth notification sound to indicate that the imaging operation is infeasible. For example, a timer is usable to check whether a predetermined time has elapsed in determining the termination of the imaging operation in the third imaging mode.

As mentioned above, in the first exemplary embodiment, the first, second, and third notification methods of the notification unit 1510 are allocated to the first, second, and third imaging modes respectively so that the notification method of the notification unit 1510 can be differentiated for each imaging mode. Thus, the user can check the selected imaging mode and the exposure permission timing, while viewing the notification unit 1510, without confirming the control terminal 1507. In particular, in the present exemplary embodiment, the notification unit 1510 is controlled in such a way as to notify the user of the good time to press the exposure switch 1502 to cause the X-ray generation apparatus 1500 to start exposure processing, instead of notifying the imaging mode or the operational state of the sensor. Therefore, the possibility of causing an error exposure operation can be reduced.

Further, when the exposure permission period is limited (see the second imaging mode), the notification unit 1510 performs a notification in such a way as to enable the user to confirm the elapsed time or remaining exposure permission period of the imaging state. For example, in a case where the imaging permissible state S1603 in the second imaging mode can be maintained for ten minutes, the notification unit 1510 can perform notification processing using the first to fourth notification sounds as described below.

First, the notification unit 1510 performs a notification using the first notification sound as time elapsing sound at one-minute intervals.

At the time when five minutes elapse, the notification unit 1510 performs a notification using the second notification sound.

Further, when the remaining time becomes one minute, the notification unit 1510 performs a notification using the third notification sound to let the user know the expiring exposure permission period.

Finally, at the time when the remaining time becomes ten seconds, the notification unit 1510 performs a notification using the fourth notification sound at predetermined short intervals and stops the fourth notification sound when the time is up.

As described above, the exposure permission period is clearly presented in the notification to be performed in the first exemplary embodiment. However, it is also feasible to clearly present an exposure infeasible period (i.e., an impermissible period). Further, the notification unit 1510 can be configured in any way as long as it can notify the user of the above-mentioned permission period and the remaining time thereof. For example, it is useful to select mutually different colors for the first to third notification lights. Further, it is useful to use notification lights that are differentiated in flicker pattern. Further, the flicker pattern of the notification light can be controlled in such a way as to express the remaining time. Further, sequentially quenching a plurality of lamps is effective to express the remaining time.

Further, even in the third imaging mode, if the remaining permission period is detectable based on a timer value of the timer that detects the termination of a imaging operation, the notification unit 1510 can switch the notification form according to the detected remaining time.

As mentioned above, according to the above-mentioned exemplary embodiments, the timing to permit an operation to cause the X-ray generation apparatus 1500 to generate X-rays is clearly presented. Therefore, the user operability can be improved. The risk of causing an erroneous operation can be reduced. Further, the risk of irradiating a patient with X-rays erroneously can be reduced. Further, the separate notification unit 1510 enables the user to confirm exposure timing information. Thus, it becomes unnecessary for the user to check the control terminal 1507 of the imaging control apparatus 300. Therefore, the work efficiency can be improved. Further, the notification unit 1510 differentiates the notification method for each imaging mode. Thus, the user can identify the present imaging mode based on the notification performed by the notification unit 1510. This is effective to prevent the user to perform an erroneous operation.

In the above-mentioned exemplary embodiment, a predetermined time is allocated, as a imaging feasible time in the second imaging mode, so that the driving state periodically transits into the imaging preparation state S1602 from the imaging permissible state S1603. In the second imaging mode according to another exemplary embodiment, the X-ray detector 200 transits into the imaging preparation state S1602 from the imaging permissible state S1603 based on the storage amount of dark current.

Accordingly, the dark current storage amount determines the period of time during which the X-ray detector 200 can operate in the imaging permissible state S1603. If the dark current storage amount reaches a storage amount limit in the imaging permissible state S1603, the driving state of the X-ray detector 200 transits into the imaging preparation state S1602 and discharges the stored electric charges (i.e., dark current). Accordingly, the notification unit 1510 according to the present exemplary embodiment performs a notification informing the amount of dark current stored during a imaging operation.

For example, when the X-ray detector 200 is operating in the imaging permissible state S1603 of the second imaging mode, the notification unit 1510
performs a notification using the first notification sound each time when the dark current storage amount increases by an amount comparable to 10% of the storage amount limit,
performs a notification using the second notification sound when the dark current storage amount reaches 50% of the storage amount limit,
performs a notification using the third notification sound when the dark current storage amount becomes equivalent to 90% of the storage amount limit to let the user know the storable dark current capacity becoming smaller.
performs an intermittent notification using the fourth notification sound when the dark current storage amount becomes equivalent to 95% of the storage amount limit, and stops generating the notification sound when the dark current storage amount reaches the storage amount limit (100%).

The dark current storage amount can be detected, for example,
by reading electric charges stored in a dark current measurement pixel, which is prepared independently of image acquisition pixels, or
by acquiring an estimation value about the time elapsing since the imaging start timing if a data table is prepared with respect to the way of storing electric charges and the stored time.

According to the present exemplary embodiment, when the amount of stored dark current substantially limits the permission period, the notification unit 1510 performs notification processing based on a ratio of the dark current storage amount to the storage amount limit (i.e., the limiting value). Therefore, in addition to the effects described in the first exemplary embodiment, according to the present exemplary embodiment, the imaging feasible time optimum for the X-ray detector 200 can be obtained even when the dark current accumulation time is variable depending on an environmental change.

Therefore, the user can effectively use the imaging feasible time. Further, when the dark current storage amount can be known beforehand, the user can predict the image quality of an X-ray image to be acquired, before starting a imaging operation. Thus, it is feasible to reduce the number of required imaging operations and the times of retrial.

The present invention can be realized by performing the following processing. More specifically, the processing includes supplying a software program that can realize the functions of the above-mentioned exemplary embodiments to a system or an apparatus via a network or an appropriate storage medium and causing a computer (or a CPU or a micro-processing unit (MPU)) of the system or the apparatus to read and execute the program.

Further, the present invention encompasses any exemplary embodiment that is obtainable by appropriately combining the above-mentioned exemplary embodiments.

According to the above-mentioned exemplary embodiments, it is feasible to perform a radiographic imaging operation while taking a momentary situation into consideration in adjusting the imaging timing. Further, according to another exemplary embodiment, it is feasible to notify a user of appropriate exposure instruction timing according to a selected imaging mode. Thus, the burden of the user in an X-ray imaging operation can be reduced. The possibility of causing an error exposure can be reduced. Further, according to another exemplary embodiment, it is feasible to set a standby time before shifting the operation mode to the storage mode. Therefore, it is feasible to cause the radiation sensor to start an operation in the storage state and cause the imaging apparatus to perform a radiographic imaging operation at timing desired for each operator.

[Statement 1]
A radiographic imaging control apparatus, including:
  a setting unit configured to set a standby time before a radiographic imaging operation starts according to an operational instruction input via an operation unit,
  a determination unit configured to determine whether the standby time elapses since a time corresponding to an instruction to start clocking the standby time, after the setting unit completes the setting processing, and
  a control unit configured to cause a radiation sensor to transit into a state where electric charges can be stored if it is determined that the standby time elapses.

[Statement 2]
The control apparatus according to statement 1, further including a display control unit configured to cause a display unit to display a display content indicating a period of time during which generating radioactive rays is prohibited if it is determined that the standby time has not yet elapsed.

[Statement 3]
The control apparatus according to statement 2, wherein the display control unit is configured to display a display content indicating the remaining standby time, as the display content indicating the period of time during which generating radioactive rays is prohibited.

[Statement 4]
The control apparatus according to statement 2 or 3, wherein the display control unit is configured to display a display content indicating that generating radioactive rays is feasible if it is determined that the standby time elapses.

[Statement 5]
The control apparatus according to any one of statements 2 through 4, wherein the setting unit is configured to set a display period of the display content indicating that generating radioactive rays is feasible based on the operational instruction input via the operation unit and a accumulation time of the radiation sensor.

[Statement 6]
The control apparatus according to any one of statements 1 through 5, wherein the control unit is configured to cause the radiation sensor to perform initialization processing for initializing the radiation sensor before it is determined that the standby time elapses.

[Statement 7]

The control apparatus according to any one of statements 1 through 6, wherein the control unit includes a communication circuit to transmit a signal that causes the radiation sensor to transit into a state where electric charges can be stored if it is determined that the standby time elapses.

[Statement 8]

The control apparatus according to statement 6, further including a display control unit configured to cause a display unit to display a display content indicating a period of time during which generating radioactive rays is prohibited if it is determined that the standby time has not yet elapsed, wherein the display control unit is configured to prevent the display unit from displaying the display content indicating that generating radioactive rays is feasible if there is any abnormality in the transmission of the signal that causes the radiation sensor to transit into the state where electric charges can be stored.

[Statement 9]

The control apparatus according to statement 2, wherein the display control unit is configured to display a display content instructing to press a first-stage switch of a radioactive ray radiation switch before it is determined that the standby time elapses.

[Statement 10]

The control apparatus according to any one of statements 1 through 9, wherein the control unit causes the communication circuit to transmit a reservation signal including the standby time and an instruction to cause the radiation sensor to transit into the state where electric charges can be stored after the standby time elapses, according to the standby time clocking start instruction.

[Statement 11]

The control apparatus according to statement 2, wherein if the communication circuit cannot receive a signal indicating that the transmitted reservation signal has been received by a partner apparatus within a predetermined period of time, the display control unit prevents the display unit from displaying the display content indicating the period of time during which generating radioactive rays is prohibited.

[Statement 12]

The control apparatus according to any one of statements 1 through 11, wherein the control unit is configured to cause the radiation sensor to transit into a state where electric charges can be stored in response to a signal from a detection unit configured to detect the start of generation of radioactive rays.

[Statement 13]

The control apparatus according to any one of statements 1 through 12, wherein the control unit is configured to cause the radiation sensor to transit into a state where electric charges can be stored in response to a signal requesting a permission for the generation of radioactive rays received from an interface that can communicate with a radiation generating apparatus.

[Statement 14]

The control apparatus according to any one of statements 1 through 13, further including a setting unit configured to set a first control to cause the radiation sensor to transit into the state where electric charges can be stored if it is determined that the standby time elapses, a second control to cause the radiation sensor to transit into the state where electric charges can be stored in response to a signal from the detection unit configured to detect the start of generation of radioactive rays, or a third control to cause the radiation sensor to transit into the state where electric charges can be stored in response to the signal requesting a permission for the generation of radioactive rays received from the interface that can communicate with the radiation generating apparatus, as a control to be performed by the control unit.

[Statement 15]

The control apparatus according to statement 14, wherein if it is determined that there is a specific error in a state where either the first control or the second control is performed, the setting unit switches the setting to perform the third control.

[Statement 16]

The control apparatus according to statement 14, further including a memory that stores radiation image data obtained according to any one of the first, second, and third controls in association with information indicating the first control, the second control, or the third control that has been performed.

[Statement 17]

A portable radiographic imaging apparatus, including the control apparatus according to any one of statements 1 through 16, the radiation sensor, and a casing accommodating the control apparatus and the radiation sensor.

[Statement 18]

The radiographic imaging apparatus according to statement 17, wherein the operation unit is detachable from the radiographic imaging apparatus and the radiographic imaging apparatus further includes a communication unit configured to communicate with the operation unit.

[Statement 19]

A radiographic imaging apparatus including:
a radiation sensor including a plurality of pixels disposed in a two-dimensional pattern to store electric charges according to reception of radioactive rays,
a setting unit configured to set a standby time before a radiographic imaging operation starts according to an operational instruction input via an operation unit,
a determination unit configured to determine whether the standby time elapses since a time corresponding to an instruction to start clocking the standby time,
a control unit configured to cause a radiographic imaging unit to transit into a storage mode if it is determined that a specific time elapses, and
a reading circuit configured to obtain image data based on the stored electric charges in response to the termination of storage processing.

[Statement 20]

A radiographic imaging control apparatus using a radiation sensor including a plurality of pixels disposed in a two-dimensional pattern to store electric charges according to reception of radioactive rays, the control unit including:
a setting unit configured to set a standby time before a radiographic imaging operation starts according to an operational instruction input via an operation unit,
a determination unit configured to determine whether the standby time elapses since a time corresponding to a predetermined instruction,
a display control unit configured to cause a display unit to display a display content indicating a period of time during which generating radioactive rays is prohibited before it is determined that the standby time elapses,
a transmission unit configured to transmit a signal that causes the radiation sensor to transit into a storage state according to the elapse of the standby time, and a reception unit configured to receive image data obtained when electric charges are stored in the radiation sensor.

[Statement 21]

A radiographic imaging system including:
a radiation sensor including a plurality of pixels disposed in a two-dimensional pattern to store electric charges according to reception of radioactive rays,
a setting unit configured to set a standby time before a radiographic imaging operation starts according to an operational instruction input via an operation unit,
a determination unit configured to determine whether the standby time elapses since a time corresponding to a standby time clocking start instruction,
a control unit configured to cause a radiographic imaging unit to transit into a storage mode if it is determined that a specific time elapses, and
a reading circuit configured to obtain image data based on the stored electric charges in response to the termination of storage processing.

[Statement 22]

A radiographic imaging notification apparatus using a radiation sensor including a plurality of pixels disposed in a two-dimensional pattern to store electric charges according to reception of radioactive rays, the notification apparatus including:
an obtaining unit configured to acquire a first signal indicating that the radiation sensor starts a clocking operation according to a radiographic imaging instruction and a second signal indicating that a specific time elapses since the start of the clocking operation, and
a display control unit configured to cause a display unit to display a display content corresponding to the time left before the specific time elapses after the radiation sensor starts the clocking operation according to the radiographic imaging instruction, and further cause the display unit to display a display content indicating to start the radiation if it is determined that the specific time elapses.

[Statement 23]

A control method including:
setting a standby time before a radiographic imaging operation starts according to an operational instruction input via an operation unit,
instructing to start clocking the standby time,
determining whether the standby time elapses, and
causing a radiation sensor to transit into a state where electric charges can be stored if it is determined that the standby time elapses.

[Statement 24]

A computer-readable storage medium storing commands to cause a computer to execute predetermined processing, the commands including:
computer-executable instructions for setting a standby time before a radiographic imaging operation starts according to an operational instruction input via an operation unit,
computer-executable instructions for determining whether the standby time elapses since a time corresponding to a standby time clocking start instruction, and
computer-executable instructions for causing a radiation sensor to transit into a state where electric charges can be stored if it is determined that the standby time elapses.

[Statement 25]

A computer-readable storage medium storing a program that causes a computer to execute a radiographic imaging control using a radiation sensor including a plurality of pixels disposed in a two-dimensional pattern to store electric charges according to reception of radioactive rays and a reading circuit configured to read an electric signal based on electric charges stored in the radiation sensor and obtain radiation image data, the program including:
computer-executable instructions for setting a standby time before a radiographic imaging operation starts according to an operational instruction input via an operation unit,
computer-executable instructions for determining whether the standby time elapses since a time corresponding to a standby time clocking start instruction,
computer-executable instructions for causing a display unit to display a display content indicating a period of time during which generating radioactive rays is prohibited before it is determined that the standby time elapses, and
computer-executable instructions for causing the radiation sensor to transit into a state where electric charges can be stored if it is determined that the standby time elapses.

[Statement 26]

A computer-readable storage medium storing a program that causes a computer to execute a radiographic imaging control using a radiation sensor including a plurality of pixels disposed in a two-dimensional pattern to store electric charges according to reception of radioactive rays, the program including:
computer-executable instructions for setting a standby time before a radiographic imaging operation starts according to an operational instruction input via an operation unit,
computer-executable instructions for determining whether the standby time elapses since a time corresponding to a predetermined instruction while monitoring a timer,
computer-executable instructions for causing a display unit to display a display content indicating a period of time during which generating radioactive rays is prohibited before it is determined that the standby time elapses, and
computer-executable instructions for transmitting a signal to cause the radiation sensor to transit into a storage state according to the elapse of the standby time, and
computer-executable instructions for receiving image data obtained when the radiation sensor is operating in the storage state.

[Statement 27]

A computer-readable storage medium storing a program that causes a computer to execute a radiographic imaging notification using a radiation sensor including a plurality of pixels disposed in a two-dimensional pattern to store electric charges according to reception of radioactive rays, the program including:
computer-executable instructions for acquiring a first signal indicating that the radiation sensor starts a clocking operation according to a radiographic imaging,
computer-executable instructions for acquiring a second signal indicating that a specific time elapses since the start of the clocking operation,
computer-executable instructions for causing the notification unit to perform a notification according to the time left before the specific time elapses, before the specific time elapses after the radiation sensor starts the clocking operation according to a radiographic imaging instruction, computer-executable instructions for causing the notification unit to perform a notification indicating to start the irradiation if it is determined that the specific time elapses.

[Statement 28]

An X-ray imaging apparatus including:
an X-ray detector configured to detect X-rays generated from an X-ray source and operable in a plurality of driving states, in which the X-ray detector performs photoelectric conversion element initialization processing in a imaging preparation state, waits for a imaging start instruction in a imaging permissible state without performing the initialization processing, and captures an image in a imaging in progress state,
a driving control unit configured to cause the X-ray detector to select a driving state according to a imaging mode selected from a plurality of imaging modes that are differentiated in combination of driving state of the X-ray detector and period of time during which a user exposure operation is permitted, and
a notification unit configured to notify whether the driving state of the X-ray detector is in a permission period in which the exposure is permissible in a transition of the driving state according to the selected imaging mode.

[Statement 29]

The X-ray imaging apparatus according to statement 28, wherein one of the plurality of imaging modes is a first imaging mode to be performed to synchronize the X-ray source with a imaging operation of the X-ray detector using predetermined communications, and the permission period is a period in which the X-ray detector is operating in the imaging preparation state or the imaging permissible state if the selected imaging mode is the first imaging mode.

[Statement 30]

The X-ray imaging apparatus according to statement 28 or 29, wherein one of the plurality of imaging modes is a second imaging mode to be performed to synchronize the X-ray source with a imaging operation of the X-ray detector by detecting X-rays generated from the X-ray source, and the permission period is a period in which the X-ray detector is operating in the imaging permissible state if the selected imaging mode is the second imaging mode.

[Statement 31]

The X-ray imaging apparatus according to any one of statements 28 through 30, wherein one of the plurality of imaging modes is a third imaging mode to be performed to synchronize the X-ray source with a imaging operation of the X-ray detector based on a user instruction to cause the X-ray source to generate X-rays after the X-ray detector transits into the imaging in progress state, and the permission period is a period in which the X-ray detector is operating in the imaging in progress state if the selected imaging mode is the third imaging mode.

[Statement 32]

The X-ray imaging apparatus according to any one of statements 28 through 31, wherein the notification unit is configured to perform a notification indicating whether the driving state is in the permission period and a notification that enables to recognize the selected imaging mode.

[Statement 33]

The X-ray imaging apparatus according to any one of statements 28 through 32, wherein the notification unit is configured to clearly express a period other than the permission period.

[Statement 34]

The X-ray imaging apparatus according to any one of statements 28 through 33, wherein if a predetermined time is set to limit the permission period the notification unit performs a notification based on the remaining time of the permission period.

[Statement 35]

The X-ray imaging apparatus according to any one of statements 28 through 34, wherein if the amount of dark current stored in the permission period is limited the notification unit performs a notification based on a ratio of the amount of stored dark current to a limiting value.

[Statement 36]

The X-ray imaging apparatus according to any one of statements 28 through 35, wherein notification forms for the notification unit is any one of light, sound, and vibration or a combination thereof.

[Statement 37]

A radiographic imaging control apparatus including:
a communication unit configured to communicate with a radiation detection apparatus,
a display control unit configured to cause a display unit to display a state of the radiation detection apparatus, and
a selection unit configured to select either a first imaging mode to be performed to synchronize a radiation source with an operation of the radiation detection apparatus using predetermined communications or a second imaging mode to be performed to cause the radiation detection apparatus to perform a imaging operation in response to a detection of radioactive rays generated from the radiation source,
wherein if the first imaging mode is selected the display control unit causes the display unit to display at least a period in which generation of radioactive rays becomes feasible, and if the second imaging mode is selected the display control unit causes the display unit to differentiate a display content for a period in which a radiation image can be acquired based on detected radioactive rays from a display content for another period.

[Statement 38]

The radiographic imaging control apparatus according to statement 37, wherein the selection unit is configured to select one of a plurality of imaging modes including the first imaging mode, the second imaging mode, and a third imaging mode in which the radiation detection apparatus performs a imaging operation according to the elapse of a setting time since an external instruction, and if the third imaging mode is selected, the display control unit causes the display unit to differentiate a display content for a period in which the radiation detection apparatus is performing the imaging operation from a display content for another period.

[Statement 39]

A method for controlling an X-ray imaging apparatus including an X-ray detector configured to detect X-rays generated from an X-ray source and operable in a plurality of driving states in which the X-ray detector performs photoelectric conversion element initialization processing in a imaging preparation state, waits for a imaging start instruction in a imaging permissible state without performing the initialization processing, and captures an image in a imaging in progress state, the method including:
causing a driving control unit to select a driving state of the X-ray detector according to a imaging mode selected from a plurality of imaging modes that are differentiated in combination of driving state of the X-ray detector and period of time during which a user exposure operation is permitted, and
causing a notification unit to notify whether the driving state of the X-ray detector is in a permission period in which the exposure is permissible in a transition of the driving state according to the selected imaging mode.

Other Embodiments

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-044404 filed Mar. 6, 2013, No. 2013-044405 filed Mar. 6, 2013, and No. 2013-044722 filed Mar. 6, 2013, which are hereby incorporated by reference herein in their entirety.

What is claimed is:

1. A radiographic imaging control apparatus, comprising:
a processor configured to function as:
a control unit configured to perform a first control to cause a radiation sensor to transit into a storage state, where electric charges can be stored, in response to a determination that a predetermined time elapses since a predetermined instruction is input, and to perform a second control to cause the radiation sensor to transit into the storage in response to a signal from a detecting circuit, of the radiation sensor, configured to detect a start of a generation of radioactive rays;
a setting unit configured to set either the first control or the second control as a control to be performed; and
an obtaining unit configured to obtain radiation image data from the radiation sensor that has transited into the storage state based on the control set by the setting unit.

2. The control apparatus according to claim 1, wherein if it is determined that there is a specific error in a state where either the first control or the second control is performed, the setting unit designates a third control to be performed.

3. The radiographic imaging control apparatus according to claim 1, wherein the control unit is configured to perform a third control to cause the radiation sensor (a) to transit into the storage state in response to a first signal received from an interface that can communicate with a radiation generating apparatus, and (b) to transmit a second signal, which causes the radiation generating apparatus to generate radioactive rays, via the interface in response to transition into the storage state, and
wherein the setting unit is configured to set one of the first, second, and third controls as a control to be performed.

4. The control apparatus according to claim 1, further comprising:
a notification control unit configured to cause a notification unit to generate a warning if the detection unit outputs a signal indicating the detection of the started generation of radioactive rays before the predetermined standby time elapses, in a state where the first control is set to be performed.

5. The control apparatus according to claim 3, further comprising:
a memory configured to store radiation image data obtained according to any one of the first, second, and third controls in association with information indicating the one of the first control, the second control, or the third control that has been performed.

6. The control apparatus according to claim 1, further comprising:
a time setting unit configured to set the standby time before a radiographic imaging operation starts according to an operational instruction input via an operation unit;
a determination unit configured to determine whether the standby time elapses since a time corresponding to the standby time clocking start instruction; and
a display control unit configured to cause a display unit to display a display content indicating a period of time during which generating radioactive rays is prohibited before it is determined that the standby time elapses,
wherein the control unit is configured to perform the first control to cause the radiation sensor to transit into the state where electric charges can be stored if it is determined that the standby time elapses.

7. The control apparatus according to claim 6, wherein the display control unit is configured to display a display content indicating a remainder of the standby time, as the display content indicating the period of time during which generating radioactive rays is prohibited.

8. The control apparatus according to claim 6, wherein the display control unit is configured to display a display content indicating that generating radioactive rays is feasible if it is determined that the standby time elapses.

9. The control apparatus according to claim 1, wherein the control unit is configured to cause the radiation sensor to perform initialization processing for initializing the radiation sensor before it is determined that the predetermined time elapses since the predetermined instruction is input.

10. A radiographic imaging control apparatus, comprising:
a processor configured to function as:
a control unit configured to perform a first control to cause a radiation sensor to transit into a storage state, where electric charges can be stored, in response to a determination that a predetermined time elapses since a predetermined instruction is input, and to perform a third control to cause the radiation sensor (a) to transit into the storage state in response to a first signal received from an interface that can communicate with a radiation generating apparatus and (b) to transmit a second signal, which causes the radiation generating apparatus to generate radioactive rays, via the interface in response to transition into the storage state;

a setting unit configured to set either the first control or the third control as a control to be performed; and an obtaining unit configured to obtain radiation image data from the radiation sensor that has transited into the storage state based on the control set by the setting unit.

11. The radiographic imaging control apparatus according to claim 1, wherein the setting unit is configured to set the control to be performed based on at least one of an operational instruction input via an operation unit and an imaging condition.

12. The control apparatus according to claim 1, wherein, when a first radiographic imaging operation is performed based on the first control, the setting unit sets a third control for a second radiographic imaging operation to be performed after the first radiographic imaging operation is terminated.

13. The control apparatus according to claim 1, wherein the display control unit is configured to cause the display unit to display a button that enables a user to switch between a setting to perform the first control and a setting to perform the third control.

14. The control apparatus according to claim 1, further comprising:

a correction unit configured to correct the sensitivity of image data captured in the second control based on image data captured in the first control.

15. A portable radiographic imaging apparatus comprising:

the control apparatus according to claim 1;

the radiation sensor, and a casing accommodating the control apparatus and the radiation sensor.

16. A radiographic imaging system comprising:

the control apparatus according to claim 1; and a portable radiographic imaging apparatus that includes the radiation sensor and a casing accommodating the radiation sensor.

17. The radiographic imaging system according to claim 16, wherein:

a communication circuit capable of performing wireless communications is provided in each of the control apparatus and the radiographic imaging apparatus.

18. A radiographic imaging control method, comprising:

detecting a start of generation of radioactive rays by using a detecting circuit of a radiation sensor configured to detect the start of generation of radioactive rays;

setting a control to be performed between a first control to cause the radiation sensor to transit into a storage state, where electric charges can be stored, in response to a determination that a predetermined time elapses since a predetermined instruction is input, and a second control to cause the radiation sensor to transit into the storage state in response to a signal received from the detection circuit;

performing the control set by the setting step; and obtaining radiation image data from the radiation sensor that has transited into the storage state based on the performed control.

19. A radiographic imaging control method, comprising:

setting a control to be performed between a first control to cause a radiation sensor to transit into a storage state, where electric charges can be stored, in response to a determination that a predetermined time elapses since a predetermined instruction is input, and a third control to cause the radiation sensor (a) to transit into the storage state in response to a first signal received from an interface that can communicate with a radiation generating apparatus and (b) to transmit a second signal, which causes the radiation generating apparatus to generate radioactive rays, via the interface in response to transition into the storage state, performing the control set by the setting step; and obtaining radiation image data from the radiation sensor that has transited into the storage state based on the performed control.

20. A non-transitory computer-readable storage medium storing a program including commands that cause a computer to implement the control method according to claim 18.

21. A non-transitory computer-readable storage medium storing a program including commands that cause a computer to implement the control method according to claim 19.

22. The control apparatus according to claim 1, wherein the predetermined instruction is an instruction for starting an imaging operation to obtain the radiation image data.

23. The control apparatus according to claim 10, wherein the predetermined instruction is an instruction for starting an imaging operation to obtain the radiation image data.

24. A radiographic imaging system comprising:

a processor configured to function as:

a setting unit configured to set control to be performed between a first control to cause a radiation sensor to transit into a storage state, where electric charges can be stored, in response to a determination that a predetermined time elapses since a predetermined instruction is input, and a second control to cause the radiation sensor to transit into the storage state in response to a signal from a detecting circuit, of the radiation sensor, configured to detect start of a generation of radioactive rays, wherein the image sensor is configured to transit into the storage state based on the control set by the setting unit and to store electric charges to generate radiation image data.

25. A radiographic imaging system comprising:

a processor configured to function as:

a setting unit configured to set a control to be performed between a first control to cause a radiation sensor to transit into a storage state, where electric charges can be stored, in response to a determination that a predetermined time elapses since a predetermined instruction is input, and a third control to cause the radiation sensor (a) to transit into the storage state in response to a first signal received from an interface that can communicate with a radiation generating apparatus and (b) to transmit a second signal, which causes the radiation generating apparatus to generate radioactive rays, via the interface in response to transition into the storage state, wherein the image sensor is configured to transit into the storage state based on the control set by the setting unit and to store electric charges to generate radiation image data.

* * * * *